(12) United States Patent
Szymkowski

(10) Patent No.: US 7,141,365 B2
(45) Date of Patent: Nov. 28, 2006

(54) METHODS FOR DIAGNOSING A MUCIN PRODUCTION ASSOCIATED DISEASE CONDITION

(75) Inventor: David Edmund Szymkowski, Mountain View, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 1054 days.

(21) Appl. No.: 09/861,038

(22) Filed: May 18, 2001

(65) Prior Publication Data

US 2004/0203144 A1 Oct. 14, 2004

(51) Int. Cl.
*C12Q 1/68* (2006.01)
*C07H 21/02* (2006.01)

(52) U.S. Cl. .......................................... 435/6; 536/23.5
(58) Field of Classification Search ..................... None
See application file for complete search history.

(56) References Cited

U.S. PATENT DOCUMENTS 6,309,857 B1  10/2001  Pauli et al.

FOREIGN PATENT DOCUMENTS

| WO | WO 99/44620 | 9/1999 |
| WO | WO 99/47674 | 9/1999 |
| WO | WO 00/73438 | 12/2000 |

OTHER PUBLICATIONS

Kirkham et al, 2002. Biochem J. 361, 537-546.*
Haynes et al. 1998. Electrophoresis. 19: 1862-1871.*
Gygi et al. 1999. Mol Cell Biol. 19: 1720-1730.*
Lian et al. 2001. Blood. 98: 513-524.*
Fessler et al. 2002. J Biol Chem. 277: 31291-31302.*
Chen et al. 2002. Molecular and Cellular Proteomics. 1: 304-313.*
Lichtinghagen et al. 2002. European Urology. 42: 398-406.*
Khartinov. 2004. Swiss Med Weekly. 134: 175-192.*
Gruber et al. 1999. Am J Physiol. 276: C1261-C1270.*
Bustin et al. 2001. DNA Cell Biol. 20(6): 331-8.*
Genbank Accession No. AX054697, deposited Jan. 13, 2001.
Genbank Accession No. Z24653, deposited Nov. 29, 1994.
Genbank Accession No. AF043977, deposited Jun. 23, 1999.
Genbank Accession No. AB026833, deposited May 26, 1999.
Genbank Accession No. F127980, deposited Aug. 11, 1999.
Genbank Accession No. AA726662, deposited Jan. 2, 1998.
Nakanishi et al. (2001) "Role of gob-5 in mucus overproduction and airway hyperresponsiveness in asthma." *Proc. Natl. Acad. Sci. USA*, vol. 98(9):5175-5180.
Achim D. Gruber, et al., "Molecular Cloning And Transmembrane Structure OF hCLCA2 from Human Lung, Trachea, And Mammary Gland," American Physiological Society, 1999, pp. 0363-6143, vol. 99.
Atsushi Nakanishi, et al., "Role of gob-5 in Mucus Overproduction and Airway Hyperresponsiveness in Asthma," PNAS, Apr. 24, 2001, pp. 5157-5180, vol. 98, No. 9.
Bendicht U. Pauli, et al., "Molecular Characteristics and Functional Diversity of CLCA Family Members," Clinical and Experimental Pharmacology and Physiology, 2000, pp. 901-905, vol. 27.
Fuller, Catherine M. et al., "Ca2+-activated Cl- channels: A newly emerging anion transport family." News in Physiological Sciences, vol. 15, Aug. 2000, pp. 165-171.
Elble, Randolph C. et al., "Molecular and functional characterization of a murine calcium-activated chloride channel expressed in smooth muscle." Journal of Biological Chemistry, vol. 277, No. 21, May 24, 2002, pp. 18586-18591.

* cited by examiner

*Primary Examiner*—Gary B. Nickol
*Assistant Examiner*—Zachary C. Howard
(74) *Attorney, Agent, or Firm*—David J. Chang

(57) ABSTRACT

Methods and compositions for modulating mucin secretion by respiratory system cells are provided. In the subject methods, an effective amount of an hCLCA2 (or homolog thereof) modulatory agent is contacted with the cell to modulate mucin secretion, e.g., decrease or increase mucin secretion, by the cell. The subject methods find use in a variety of different applications, including the treatment of disease conditions associated with respiratory system mucin secretion, e.g., mucin hyper- or hyposecretion. Also provided are methods of screening for respiratory system mucin secretion modulatory agents. Finally, mCLCA4 and non-human homologs thereof, as well as nucleic acid compositions encoding the same, are provided.

2 Claims, 35 Drawing Sheets

Nucleotide sequence of novel mCLCA4

```
ID    mCLCA4   standard; DNA; 2549 BP.
DE    mCLCA4, novel RBS gene (2549 nt) DS 5/10/01
SQ    Sequence 2549 BP; 769 A; 539 C; 572 G; 669 T; 0 other;
SEQ0  Length: 2549   May 10, 2001   23:47   Type: N   Check: 5895   ..
         GCACGAGCTT TGAGGTGGTT GAGGAGCGGA ATGGAAGAGC TGACGGCTCT
         GTCCTGATAT TAGTGACCAG TGGAGCAGAT GAACACATTG CCAACTGCCT
         GCTCACCTCG ATGAACAGTG GATCCACCAT TCACTCCATG GCCCTGGGTT
         CCTCTGCAGC CAGAAAGTG GGGGAATTAT CACGTCTTAC AGGAGGTCTA
         AAGTTCTTCA TTCCAGATAA ATTTACTTCT AATGGAATGA CTGAAGCTTT
         CGTTCGAATC TCTTCTGGAA CAGGAGACAT TTTCCAGCAA AGCTTACAGG
         TTGAGAGCGT GTGCGAAACT GTGCAACCCC AGCACCAGCT GGCGGATACT
         ATGACTGTGG ATAGCGCCGT GGGCAATGAC ACACTTTTC TAGTCACGTG
         GCAGACTGGT GGCCCCCCTG AGATTGCATT ATTGGATCCT AGCGGAAGAA
         AATACAACAC TGGTGACTTT ATCATCAACC TGGCCTTTCG GACGCCAGC
         CTTAAGATTC CAGGGACAGC TAAGCATGGG CACTGGACTT ACACGCTGAA
         CAACACCCAC CATTCTCCCC AAGCTCTGAA AGTGACAGTG GCCTCTCGTG
         CCTCCAGCCT GGCCATGTCC CCAGCCACTC TGGAAGCCTT TGTGGAAAGA
         GACAGCACCT ATTTTCCTCA GCCAGTGATC ATTTATGCGA ATGTGAGGAA
         AGGTCTGCAT CCCATTCTCA ATGCCACCGT GGTGGCGACA GTGGAACCAG
         AGGCTGGAGA TCCCGTTGTA CTGCAACTTT TGGATGGCGG AGCAGGTGCA
         GATGTTATAA GAAATGATGG GATTTACTCC AGATAATATT CAAATGAATG
         CTCCCAAAAA CTTGGGCCAC AGACCTGTGA GGAGAGGTG GGGCTTCAGT
         CGAGTGAGCT CGGGAGGCTC CTTCTCCGTG CTGGGAGTCC CAGACGGCCC
         CCACCCTGAC ATGTTTCCAC CGTGCAAAAT TACTGACCTG GAAGCCATGA
         AAGTGGAAGA CGACGTCGTC CTCTCTTGGA CGGCACCTGG GGAAGACTTC
         GATCAGGGGC AAACTACAAG CTATGAAATA GAATGAGCA GAAGCCTATG
         GAACATTCGG GATGACTTTG ACAATGCCAT CTTGGTGAAT TCGTCAGAGC
         TAGTTCCTCA GCATGCTGGC ACCAGGGAGA CATTTACATT CTCACCCAAG
         CTTGTCACCC ATGAACTTGA TCATGAACTT GCTGAAGATG CACAAGAACC
         CTACATAGTG TATGTGGCCC TGAGAGCCAT GGATAGAAGC TCCCTCAGGT
         CAGCTGTGTC AAACATTGCC CTGGTATCAA TGTCTCTTCC TCCAAACTCT
         TCTCCTGTAG TGAGCAGAGA TGATCTGATC CTGAAAGGAG TTTTAACAAC
         AGTAGGTTTG ATAGCAATCC TTTGCCTTAT TATGGTTGTA GCACACTGTA
         TTTTTAACAG GAAAAAGAGA CCATCAAGAA AAGAGAATGA GACAAAATTT
         CTATGAACAA GCAGGCACAG TATCTTCCTT CTTAGGTAGG ATGGACATGA
         CCTTTACATC CACAAAATAA AATGTGAACA AAATCAAAAT AGTCTCGACA
         TGGGGACTTT TACATAATGC AAAAATGCCC TCCCCCCCCC CCAAAAAAAA
         CCCACCAACT TTTAACTCAT TTTGGGAAAG GGTTAGAAAA CAGTGTAAGG
         TTCCAGTTAT GGAAAAATAA TAAAATATAT TGCTCAAGGT AATGGCTTGA
         AAGGCAAAGG AAGAACAAAA TCAAATCGAG TCAAGAAAAG CTTGTTTTAT
         TGAAGTTCAG GTTGGGGGAA GTTCTGGGTA CAGAAAAGAA TGTTGGGTCT
         TAGTTAGACA GTGTAACTAT CTGTATGATG CAAACATGTT ACTTTGATGA
         ATTTCTCATC TCTGCTTATC TGTGCAGAGA AGGACACATG TTTATACTGA
         CAACCAAGCT GCTTTATAGA AGAGGCCATA CTACAGGGTT CTTTATATCT
         TGTCCTTTGG TTAAATTCAC TGTGGCTCAC AAGACACCAC TAAAGTTCAG
         ATAGGACTTT TCTCACCATG AGAGGAGACC TTAGAATGCA ATTGTTGTCC
         TTGTCCCTTG GATACTGATC TGTAGCAGAG GTCACCGGAG TTTACTGTTT
         GTAAGACGTT AGTGCCATTG AAGCAGCTTT CTAAGTTATT GGCTTGGAAG
         TATTGAATGA AAATGGTTAC GGCTCCCATG AGGCTTTACA GGTAAAAGAC
         ATTATGCTGA ATAATTTTA ATATATACAC CATATAGTTT TATTCCATCT
         CAAATAAGAA GTCATGGAAA CAATTAGCAA ATTCTGCCCC GGTTTAATAA
         GTACATGCAA TTCTTTTCTT CATCAAGGAC ACAGAGAAGA CAGCAGAGAA
         AATGTGGAAA TAAAAATCAT CTAATGCTAC TTCTTCCTTT TAAAAAATGT
         TATTTAATAA TATTATGTCA TTTCTAAATT CAAGAACTTA AAGGTTTATT
         GAATAAATAT TATGTTACAG AAAAAAAAAA AAAAAAACTC GAGGGGGGG (SEQ ID NO:01)
```

FIG. 1A

Alignment of novel mCLCA4 vs. known hCLCA2 (AF034977)

Novel mouse CLCA4 sequence contains 134 nt deletion (GGTATTTTTT
CTCCTTTGCT GCAAATGGTA GATATAGCTT GAAAGTGCAT GTCAATCACT CTCCCAGCAT
AAGCACCCCA GCCCACTCTA TTCCAGGGAG TCATGCTATG TATGTACCAG GTTACACAGC
AAAC relative to human CLCA2

GAP of: SEQ0.seq   check: 5895   from: 1  to: 2549

Novel mouse CLCA4
ID   SEQ0     standard; DNA; 2549 BP.
DE   mCLCA4, novel RBS gene (2549 nt) DS 5/10/01
SQ   Sequence 2549 BP; 769 A; 539 C; 572 G; 669 T; 0 other;

to: AF043977   check: 4566   from: 1  to: 2970

Human CLCA2
ID   AF043977   standard; RNA; HUM; 2970 BP.
AC   AF043977;
SV   AF043977.1
DT   29-JUN-1999 (Rel. 60, Created)
DT   29-JUN-1999 (Rel. 60, Last updated, Version 1) . . .

```
          Gap Weight:       50      Average Match:   10.000
       Length Weight:        3      Average Mismatch: 0.000

Quality:    11319             Length:     3983
               Ratio:    4.441               Gaps:        2
   Percent Similarity:  77.018   Percent Identity:   77.018

Match display thresholds for the alignment(s):
                    | = IDENTITY
                    : = 5
                    . = 1 mCLCA4 x AF043977        May 10, 2001 23:47  ..
 m4 = mCLCA4, h2 = hCLCA2

.         .         .         .         .
    1 ..........................................GCA 3
m4

CACCACTGTATCAGCTAAAACAGACATCAGCATTTGTTCAGGGCTTAAGA
h2

.         .         .         .         .
           CGAGCTTTGAGGTGGTTGAGGAGCGGAATGGAAGAGCTGACGGCTCTGTC
m4
           |  ||||||||||||  | |  ||||||||  |||| |  ||||||||
           AAGGATTTGAGGTGGTTGAAAAACTGAATGGAAAGCTTATGGCTCTGTG
h2
```

FIG. 1B

```
m4  CTGATATTAGTGACCAGTGGAGCAGATGAACACATTGCCAACTGCCTGCT
    |||||||||||||||| |||| ||| | |   ||| ||| ||| | |
h2  ATGATATTAGTGACCAGCGGAGATGATAAGCTTCTTGGCAATTGCTTACC m4  CACCTCGATGAACAGTGGATCCACCATTCACTCCATGGCCCTGGGTTCCT
    |||   | | | |||||| || || ||||||||||| |||||||||||| |
h2  CACTGTGCTCAGCAGTGGTTCAACAATTCACTCCATTGCCCTGGGTTCAT m4  CTGCAGCCAGAAAAGTGGGGGAATTATCACGTCTTACAGGAGGTCTAAAG
    |||||||   |||   ||| ||||||||||||||||||||||||| |||||
h2  CTGCAGCCCCAAATCTGGAGGAATTATCACGTCTTACAGGAGGTTTAAAG m4  TTCTTCATTCCAGATAAATTTACTTCTAATGGAATGACTGAAGCTTTCGT
    |||||  |||||||||| ||  | || ||| | |||| ||| ||||||
h2  TTCTTTGTTCCAGATATATCAAACTCCAATAGCATGATTGATGCTTTCAG m4  TCGAATCTCTTCTGGAACAGGAGACATTTTCCAGCAAAGCTTACAGGTTG
    |  ||||  || |||||||| ||||||||||||||||||    |  |||  |||  |||
h2  TAGAATTTCCTCTGGAACTGGAGACATTTTCCAGCAACATATTCAGCTTG m4  AGAGCGTGTGCGAAACTGTGCAACCCCAGCACCAGCTGGCGGATACTATG
    | ||       |  ||||| |||  ||||  || || ||  ||     | || ||
h2  AAAGTACAGGTGAAAATGTCAAACCTCACCATCAATTGAAAAACACAGTG m4  ACTGTGGATAGCGCCGTGGGCAATGACACACTTTTTCTAGTCACGTGGCA
    |||||||||  |  ||||||||| |||||||| | ||||||||| ||||||||||
h2  ACTGTGGATAATACTGTGGGCAACGACACTATGTTTCTAGTTACGTGGCA m4  GACTGGTGGCCCCCCTGAGATTGCATTATTGGATCCTAGCGGAAGAAAAT
    | |  ||||  || |||||||||  ||||||  |||||| ||| ||||||
h2  GGCCAGTGGTCCTCCTGAGATTATATTATTTGATCCTGATGGACGAAAAT m4  L ACAACACTGGTGACTTTATCATCAACCTGGCCTTTCGGACAGCCAGCCTT
    || ||||   | | ||||||||| || ||  |  |||||||||||| || |||
h2  L ACTACACAAATAATTTTATCACCAATCTAACTTTTCGGACAGCTAGTCTT
```

FIG. 1B (CONT.)

```
h2          AAGATTCCAGGGACAGCTAAGCATGGGCACTGGACTTACACGCTGAACAA
m4          ||||||||| |||||||||| |||||||||||||||||| ||||||||
            TGGATTCCAGGAACAGCTAAGCCTGGGCACTGGACTTACACCCTGAACAA
h2 h2          CACCCACCATTCTCCCCAAGCTCTGAAAGTGACAGTGGCCTCTCGTGCCT
m4          ||||| ||||||| ||||| |||||||||||||||| ||||||| ||||
            TACCCATCATTCTCTGCAAGCCCTGAAAGTGACAGTGACCTCTCGCGCCT
h2 h2          CCAGCCTGGCCATGTCCCCAGCCACTCTGGAAGCCTTTGTGGAAAGAGAC
m4          ||| | || || |||||||||| |||||||||||||||||||||||||
            CCAACTCAGCTGTGCCCCCAGCCACTGTGGAAGCCTTTGTGGAAAGAGAC
h2 h2          AGCACCTATTTTCCTCAGCCAGTGATCATTTATGCGAATGTGAGGAAAGG
m4          ||| | |||||||||| || ||||| |||||||| ||||||| | ||
            AGCCTCCATTTTCCTCATCCTGTGATGATTTATGCCAATGTGAAACAGGG
h2 h2          TCTGCATCCCATTCTCAATGCCACCGTGGTGGCGACAGTGGAACCAGAGG
m4            | |||||||||| |||||||| ||    || ||||| || ||||||
            ATTTTATCCCATTCTTAATGCCACTGTCACTGCCACAGTTGAGCCAGAGA
h2 h2          CTGGAGATCCCGTTGTACTGCAACTTTTGGATGGCGGAGCAGGTGCAGAT
m4          |||||||||| ||| ||| ||| ||  | |||| |||||||||| |||
            CTGGAGATCCTGTTACGCTGAGACTCCTTGATGATGGAGCAGGTGCTGAT
h2 h2          GTTATAAGAAATGATGGGATTTACTCCA......................
m4          ||||||| |||||||||| ||||||| |
            GTTATAAAAAATGATGGAATTTACTCGAGGTATTTTTTCTCCTTTGCTGC
h2 nt2129-2262 (134nt, 44.7 aa) deleted in m4 compared to h2 h2          ...........GATAATATTCAAATGAATGCTCCCAAAAACTTGGGCCA
m4          | |||||||||| |||||||||||| | || | |
            TACACAGCAAACGGTAATATTCAGATGAATGCTCCAAGGAAATCAGTAGG
```

FIG. 1B (CONT.)

```
h2  CAGACCTGTGAAGGAG...AGGTGGGGCTTCAGTCGAGTGAGCTCGGGAG
    ||||  || | ||||||    | |||||||||| || ||||| |||||  ||||
m4  CAGAAATGAGGAGGAGCGAAAGTGGGGCTTTAGCCGAGTCAGCTCAGGAG h2  GCTCCTTCTCCGTGCTGGGAGTCCCAGACGGCCCCCACCCTGACATGTTT
    ||||||| || |||||||||| ||||    |||||||||||||| |||||
m4  GCTCCTTTTCAGTGCTGGGAGTTCCAGCTGGCCCCCACCCTGATGTGTTT h2  CCACCGTGCAAAATTACTGACCTGGAAGCCATGAAAGTGGAAGACGACGT
    ||||| |||||||||| ||||||||||| |||| ||||| || ||  |
m4  CCACCATGCAAAATTATTGACCTGGAAGCTGTAAAAGTAGAAGAGGAATT h2  CGTCCTCTCTTGGACGGCACCTGGGGAAGACTTCGATCAGGGGCAAACTA
       ||| ||||||||| |||||||| |||||||| |||||||| ||  |||
m4  GACCCTATCTTGGACAGCACCTGGAGAAGACTTTGATCAGGGCCAGGCTA h2  CAAGCTATGAAATAAGAATGAGCAGAAGCCTATGGAACATTCGGGATGAC
    ||||||||||||||||||||||| | ||| ||| ||| || | ||||||
m4  CAAGCTATGAAATAAGAATGAGTAAAAGTCTACAGAATATCCAAGATGAC h2  TTTGACAATGCCATCTTGGTGAATTCGTCAGAGCTAGTTCCTCAGCATGC
    ||| |||||||| || || || ||| | ||| ||| |  ||||||||| ||
m4  TTTAACAATGCTATTTTAGTAAATACATCAAAGCGAAATCCTCAGCAAGC h2  TGGCACCAGGGAGACATTTACATTCTCACCCAAGCTTGTCACCCATGAAC
    ||||| |||||||| ||||||| ||||||||||  || ||  ||| || ||
m4  TGGCATCAGGGAGATATTTACGTTCTCACCCCAGATTTCCACGAATGGAC h2  TTGATCATGAACTTGCTGAAGATGCACAAGAACCCTACATAGTGTATGTG
    ||| ||| | |   || ||| |||| ||| | ||| | | |||||
m4  CTGAACATCAGCCAAATGGAGAAACACATGAAAGCCACAGAATTTATGTT h2  GCCCTGAGAGCCATGGATAGAAGCTCCCTCAGGTCAGCTGTGTCAAACAT
```

FIG. 1B (CONT.)

```
        | |   |    ||||  ||||||||| |  ||||| |    ||| ||||| || |||||
        GCAATACGAGCAATGGATAGGAACTCCTTACAGTCTGCTGTATCTAACAT
h2

TGCCCTGGTATCAATGTCTCTTCCTCCAAACTCTTCTCCTGTAGTGAGCA
m4

||||| ||    |   ||| | |||| || || |||  |||||||    ||
        TGCCCAGGCGCCTCTGTTTATTCCCCCAATTCTGATCCTGTACCTGCCA
h2

GAGATGATCTGATCCTGAAAGGAGTTTTAACAACAGTAGGTTTGATAGCA
m4

||||| ||||  ||  |||||||||||||||||| || |  ||||||||| |
        GAGATTATCTTATATTGAAAGGAGTTTTAACAGCAATGGGTTTGATAGGA
h2

ATCCTTTGCCTTATTATGGTTGTAGCACACTGTATTTTTAACAGGAAAAA
m4

|||  ||||||||||||   |||||  ||||     || ||| | |||||||||
        ATCATTTGCCTTATTATAGTTGTGACACATCATACTTTAAGCAGGAAAAA
h2

GAGACCATCAAGAAAAGAGAATGAGACAAAATTTCTATGAACAAGCAGGC
m4

|||| ||    |   ||||||||||||  |||||||||   ||| || || |  | |
        GAGAGCAGACAAGAAAGAGAATGGAACAAAATTATTATAAATAAATATCC
h2

ACAGTATCTTCCTTCTTAGGTAGGATGGACATGACCTTTACATCCACAAA
m4

|  ||| ||||||||||| |
        AAAGTGTCTTCCTTCTCAAA.............................
h2
``` h2=SEQ ID NO:03
m4=SEQ ID NO:01

FIG. 1B (CONT.)

Predicted protein sequence of novel mCLCA4

Novel mCLCA4 predicted protein sequence:

TSFEVVEERNGRADGSVLILVTSGADEHIANCLLTSMNSGSTIHSMALGS

SAARKVGELSRLTGGLKFFIPDKFTSNGMTEAFVRISSGTGDIFQQSLQV

ESVCETVQPQHQLADTMTVDSAVGNDTLFLVTWQTGGPPEIALLDPSGRK

YNTGDFIINLAFRTASLKIPGTAKHGHWTYTLNNTHHSPQALKVTVASRA

SSLAMSPATLEAFVERDSTYFPQPVIIYANVRKGLHPILNATVVATVEPE

AGDPVVLQLLDGGAGADVIRNDGIYSRNIQMNAPKNLGHRPVKERWGFSR

VSSGGSFSVLGVPDGPHPDMFPPCKITDLEAMKVEDDVVLSWTAPGEDFD

QGQTTSYEIRMSRSLWNIRDDFDNAILVNSSELVPQHAGTRETFTFSPKL

VTHELDHELAEDAQEPYIVYVALRAMDRSSLRSAVSNIALVSMSLPPNSS

PVVSRDDLILKGVLTTVGLIAILCLIMVVAHCIFNRKKRPSRKENETKFL (SEQ ID NO:02)

FIG. 1C

Alignment of novel mCLCA4 protein to known hCLCA2 (AF034977)

Gap of adjusted mCLCA4, eliminating stop codon formed by deletion vs. hCLCA2:

GAP of: mCLCA4   check: 109   from: 1   to: 500

ID    mCLCA4    standard; PRT; 500 AA.
DE    mCLCA4 adjusted to eliminate stop codon (500 aa)
SQ    Sequence 500 AA;

to: hCLCA2    check: 4489   from: 1   to: 943

ID    hCLCA2    standard; PRT; 943 AA.
DE    hCLCA2 aa (943aa)
SQ    Sequence 943 AA;

Symbol comparison table:
/SOFT/bi/apps/gcg102/gcgcore/data/rundata/blosum62.cmp
CompCheck: 1102

```
        Gap Weight:        8       Average Match:     2.778
     Length Weight:        2       Average Mismatch: -2.248

Quality:     1695              Length:      943
             Ratio:    3.390                Gaps:        2
Percent Similarity:   75.200    Percent Identity:   69.800
```

Match display thresholds for the alignment(s):
                | = IDENTITY
                : = 2
                . = 1 m4 = mCLCA4, h2 = hCLCA2

```
      1 ................................................TSF        m4
                                                         |
         IASFDSKGEIRAQLHQINSNDDRKLLVSYLPTTVSAKTDISICSGLKKGF         h2

EVVEERNGRADGSVLILVTSGADEHIANCLLTSMNSGSTIHSMALGSSAA         m4
         ||||. ||:| |||:||||| |.: ||| | :.||||||||.|||||||
         EVVEKLNGKAYGSVMILVTSGDDKLLGNCLPTVLSSGSTIHSIALGSSAA         h2

RKVGELSRLTGGLKFFIPDKFTSNGMTEAFVRISSGTGDIFQQSLQVESV         m4
         . ||||||||||||:|| || | :|| ||||||||||||| :|.||
         PNLEELSRLTGGLKFFVPDISNSNSMIDAFSRISSGTGDIFQQHIQLEST         h2
```

FIG. 1D

```
CETVQPQHQLADTMTVDSAVGNDTLFLVTWQTGGPPEIALLDPSGRKYNT          m4
| |·| ||| ·|·|||· |||||:|||||| ||||| | || |||| |
GENVKPHHQLKNTVTVDNTVGNDTMFLVTWQASGPPEIILFDPDGRKYYT          h2

GDFIINLAFRTASLKIPGTAKHGHWTYTLNNTHHSPQALKVTVASRASSL          m4
·|| || |||||| |||||| |||||||||||||| |||||||| ||||·
NNFITNLTFRTASLWIPGTAKPGHWTYTLNNTHHSLQALKVTVTSRASNS          h2

AMSPATLEAFVERDSTYFPQPVIIYANVRKGLHPILNATVVATVEPEAGD          m4
|· |||·|||||||||| :|| ||·|||||:·| :|||||||| |||||| ||
AVPPATVEAFVERDSLHFPHPVMIYANVKQGFYPILNATVTATVEPETGD          h2

PVVLQLLDGGAGADVIRNDGIYSR..........................         m4
|| |·||| |||||||:||||||||
PVTLRLLDDGAGADVIKNDGIYSRYFFSFAANGRYSLKVHVNHSPSISTP          h2

....................NIQMNAP.KNLGHRPVKERWGFSRVSSGGSF         m4
                    ||||||| |··|   ·:||||||||||||
AHSIPGSHAMYVPGYTANGNIQMNAPRKSVGRNEEERKWGFSRVSSGGSF          h2

SVLGVPDGPHPDMFPPCKITDLEAMKVEDDVVLSWTAPGEDFDQGQTTSY          m4
|||||| |||||·|||||| ||||·|||::· |||||||||||||| |||
SVLGVPAGPHPDVFPPCKIIDLEAVKVEEELTLSWTAPGEDFDQGQATSY          h2

EIRMSRSLWNIRDDFDNAILVNSSELVPQHAGTRETFTFSPKLVTHELDH          m4
|||||:|| ||·|||·||||||·|· || || || |||||·: |·  :|
EIRMSKSLQNIQDDFNNAILVNTSKRNPQQAGIREIFTFSPQISTNGPEH          h2

ELAEDAQEPYIVYVALRAMDRSSLRSAVSNIALVSMSLPPNSSPVVSRDD          m4
: : | : :|||:|||||·||·||||||||  :  :|||| || ·||
QPNGETHESHRIYVAIRAMDRNSLQSAVSNIAQAPLFIPPNSDPVPARDY          h2

LILKGVLTTVGLIAILCLIMVVAHCIFNRKKRPSRKENETKFL  500           m4
||||||||·|||  |:|||·|| |   ·|||| :||| || |
LILKGVLTAMGLIGIICLIIVVTHHTLSRKKRADKKENGTKLL  943           h2
``` m4=SEQ ID NO:02
h2=SEQ ID NO:04

FIG. 1D (CONT.)

| Gene name | GenBank Accession # | Forward Primer | Reverse Primer | Taqman Probe |
|---|---|---|---|---|
| hGAPDH | M33197 | GTTCGACAGTCAGCCGCATC | GGAATTTGCCATGGGTGGA | ACCAGGCGCCCAATACGACCAA |
| hMUC1 | AF084521 | GCCAGGATCTGTGGTGGTACA | CTCCACGTCGTGGACATTGA | GGCACATCACTCACGCTGACGTCTGA |
| hMUC2 | L21998 | CCCAACTTTGATGCCAGCATT | CAGCATCCATTGGGCATGA | TGTGATGGAGCCCGGATGCA |
| hMUC4 | AJ010901 | CGAAAACAGCCCACTGATGTC | TGGAGGCCTGAGTTGGAATT | AGGGCGATACCTCTCCCACACTGGC |
| hMUC5AC | U06711 | TACTCGCTCGAGGGCAACA | TGCAGTGCAGGGTCACATTC | CCAGGAGCTGCGGACCTCGC |
| hMUC5B | Z72496 | GTGTGGGTGGTCTCTGGAGTAGA | AAATCCACAGCTACCAGCTTTACA | TGGACCGTCCCAGCAACAGACCA |
| hMUC6 | HSU97698 | CCACTTCTCGCCTCCATCCA | GGCCTTGAGCGTTGTTGGT | TCAACGCCAACAGGCACCGTTC |
| hCLCA1 | AF039400 | GCAAGGTGGCTTTGTAGTGGA | AGACTGTATTTCCAAGTGCCAACC | ACACCAAAATGCCTACCTCCAAATCCC |
| hCLCA2 | AF043977 | GAGGCCGAGTGTTTGTCAT | CCATTTATGTAGAAAGGTTTGTCATG | TGGGCCCACCTCCGTTGGG |
| hCLCA3 | AF043976 | CCTGAAGTCACAGATGATGTGGAA | AGGCACTCCTGATACAGTAAACGA | CAGACGACTTCAGCAGACTCACCTCTGG |
| hCLCA4 | AF127035 | GAATCAAGCAGCAAAACATTTCC | GTGGCAGTACTATCAAAGTGAACCA | CCCAGGATCCATTTTCAACAGTCTGCAG |
| mGAPDH | M32599 | GTCCCGTAGACAAGATGGTGAAG | GTGACCAGGCGCCCAAT | CGGTGTGAACGGATTTGGCCG |
| mMUC1 | M84683 | CCAGGACTTCTGCTGGTAGGCTGTT | GGGCTTCACCAGGCTTACG | ATGCCCTTTGTCAAGCGCCTCAACT |
| mMUC2 | AF080584 | GCTGGCTTCGCCAATACCT | GGTCATCTAGCCAGTCCAGCTT | AGGCCCAATCAAGCTGCCACGA |
| mMUC5AC | L42292 | TCTACCACTGCCACCTGTCACT | CCAGGTCTCTCTCTCAGTCTTG | CGGGATCGGTGCAATGTGTTTCC |
| mCLCA1 (possibly cross reacts with hCLCA2) | AF047838 | CCCTAGCCGGATGATTGTGT | TGACATTGGCTCCCAGAACA | CGCAGGGTCAGCCAAGGATTTT |
| mCLCA3 | AB017156 | CCACTTCAACACACCTCACTCCAA | CAAACTCAAAGATTTCCTCAGA | AACACTACCGGTCTTATCCCAAAGAGGC |
| mCLCA4 | AA726662 (468 nt EST only) (Full-length mCLCA4 is novel Roche gene) | AGTGACCAGTGGAGCAGATGAA | GGGCCATGGAGTGAATGG | CCAACTGCCTGCTCACCTCGATGA |

All sequences 5'-3' (h, human; m, mouse gene).

FIG. 2

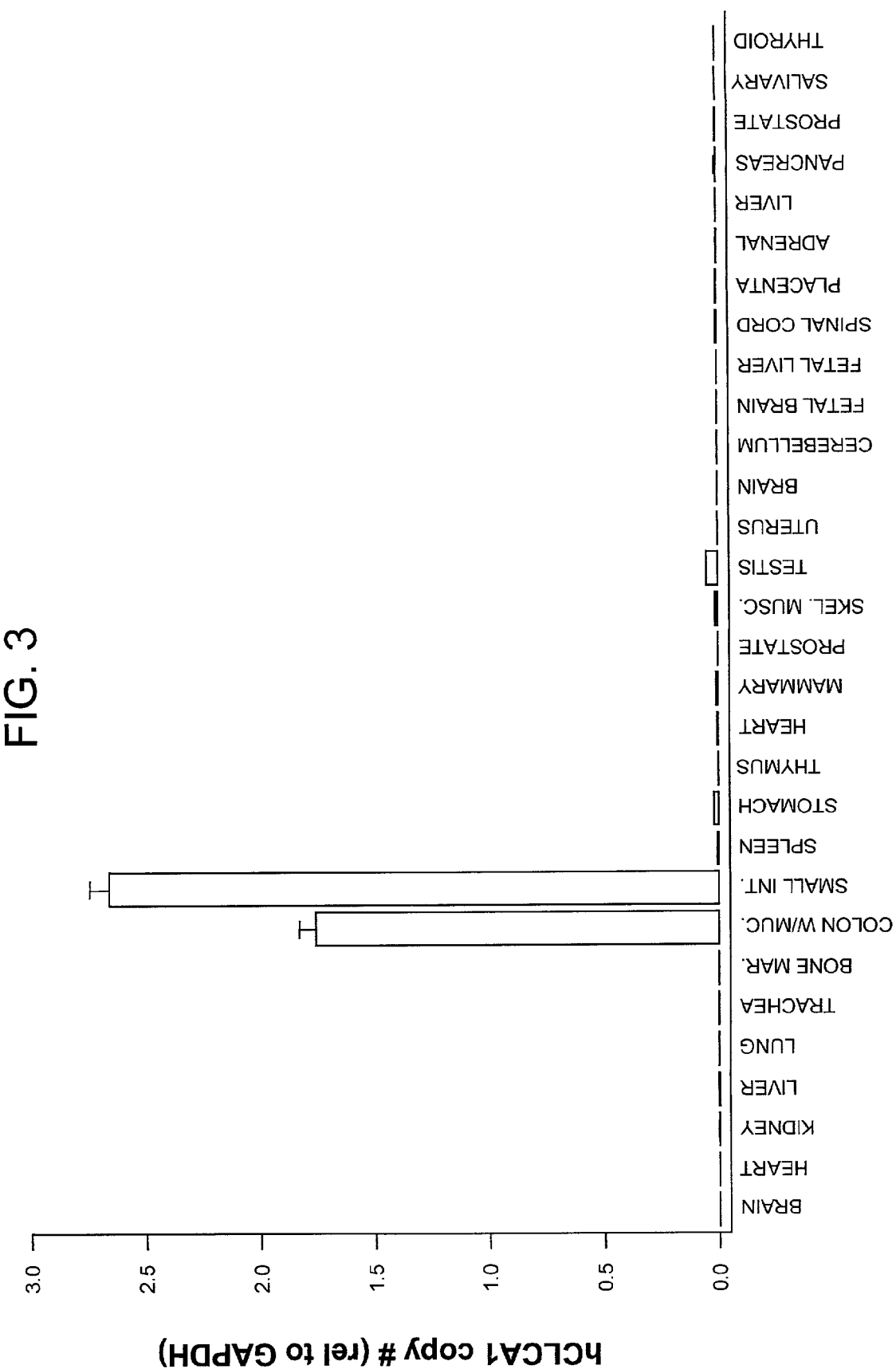

3 bronchi × 4 pts antisense probe

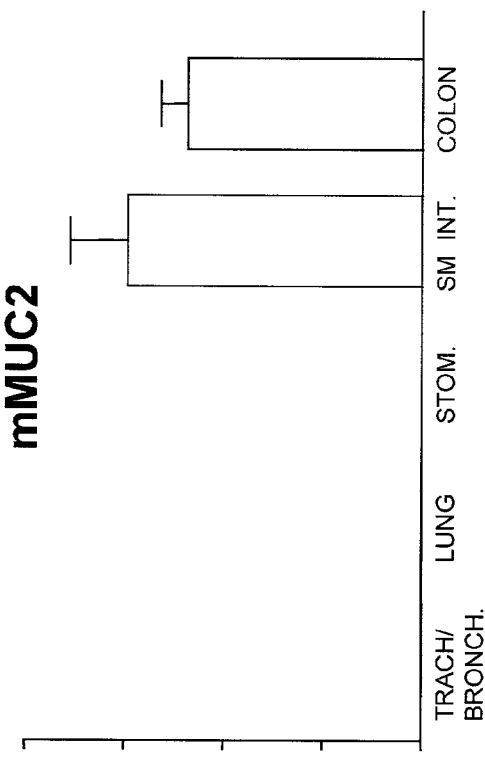
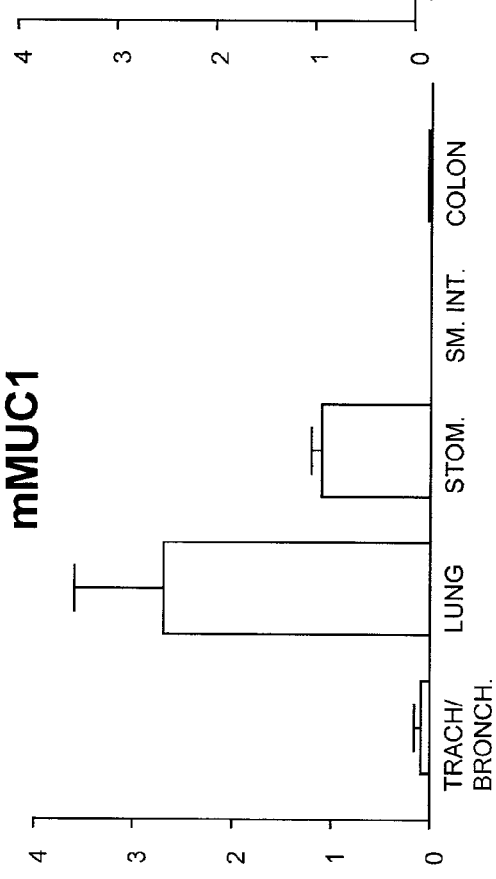
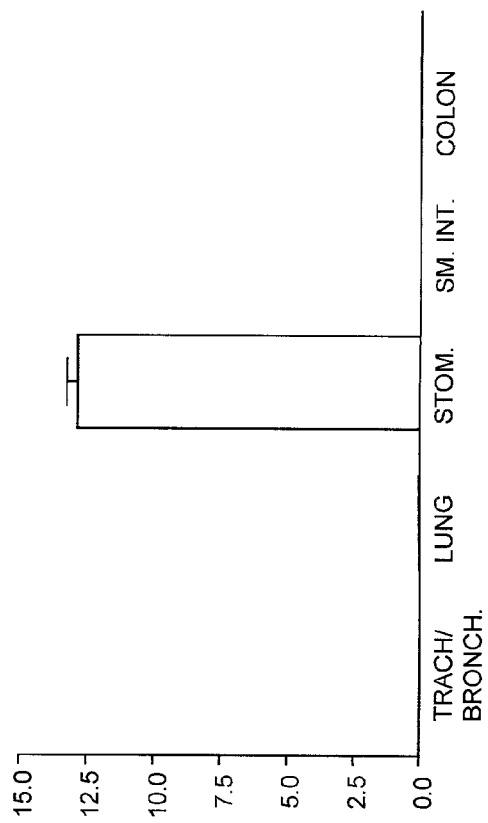
FIG. 26

METHODS FOR DIAGNOSING A MUCIN PRODUCTION ASSOCIATED DISEASE CONDITION

FIELD OF THE INVENTION

The field of this invention is mucin secretion and diseases associated therewith, particularly respiratory system mucin secretion and diseases associated therewith.

BACKGROUND OF THE INVENTION

Mucus is a thin film of protective viscoelastic liquid which lines the airways, gastrointestinal tract, and other organs containing mucus membranes. Mucus is an aqueous solution in which the major component is a glycoconjugate, known as mucin. Mucin secretion may be constitutive, regulated, or may occur in response to external stimuli, e.g., irritants.

In the lungs, improper or inappropriate mucus or mucin secretion, e.g., mucus hypersecretion, can result in severe medical conditions such as chronic bronchitis (CB), asthma, chronic obstructive pulmonary disease (COPD), and bronchiectasis. Patients suffering from cystic fibrosis (CF) will manifest pulmonary disorders associated with mucus hypersecretion, and may also have gastrointestinal complications.

Chloride channels, widely distributed throughout various tissues, play roles as diverse as maintaining membrane potential in muscles to movement of Cl⁻ for fluid and electrolyte transport in epithelial tissues. Several studies have suggested that a calcium activated secretory pathway for Cl⁻ may play a role in modulating the disease severity in various tissues of CF patients. (See, Anderson and Welsh (1991) *Proc. Natl. Acad. Sci.* 88:6003–6007; Knowles, et al. (1991) *N. Engl. J. Med.* 325:533–538; Mason, et al. (1991) *Br. J. Pharmacol.* 103:1649–1656; Wagner, et al. (1991) *Nature* 349:793–796; and Willumsen and Boucher (1989) *Am. J. Physiol.* 256(Cell Physiol. 25):C226–C235.)

A new family of proteins has recently been discovered that mediates a $Ca^{2+}$-activated Cl⁻ conductance in a variety of tissues. Members of this family that have been identified include: bovine lung endothelial cell adhesion molecule, Lu-ECAM-1 (Elble, et al. (1997) *J. Biol. Chem.* 272:27853–27861); bovine $Ca^{2+}$-activated Cl⁻, CaCC or bCLCA1 (Cunningham, et al. (1995) *J. Biol. Chem.* 270:31016–31026); murine CLCA1, mCLCA1 (Gandhi, et al. (1998) *J. Biol. Chem.* 273:32096–32101); human CLCA1, hCLCA1 (Gruber, et al. (1998) *Genomics* 54:200–214); murine Gob-5, mGob-5 (Komiya, et al. (1999) *Biochem. Biophys. Res. Comm.* 255:347–351; and human CLCA2, hCLCA2 (Gruber, et al. (1999) *Am. J. Physiol.* 276(*Cell Physiol.* 45):C1261–C1270.) Recently, Holroyd, et al., PCT publication No. WO 99/44620, described mouse and human channels that are induced by IL-9. Collectively, these channels are referred to as Calcium-activated Chloride Channels (CLCA).

It has been reported that the stimulation of chloride secretion results in the secretion of mucin from goblet cells in the intestinal epithelium. (Halm, et al. (1995) *Am. J. Physiol.* 269:929–942.) The murine Gob-5 gene, mGob-5, has been shown, through in situ hybridization, to be expressed in the mucus-secreting cells of the stomach, small intestine, colon, and uterus, along with slight expression in the trachea. (Komiya, et al. supra.) Similarly it was suggested that human CLCA1, the human homolog of mGob-5, may also have a role in mucus secretion. See e.g., Nakanishi et al., Proc. Nat'l Acad. Sci. USA (Apr. 24, 2001) 98:5175–5180.

To date, however, a definitive chloride channel target for regulating mucin secretion has yet to be identified, particularly with respect to mucin secretion by cells of the respiratory system. As such, there is a continued need for the identification of a specific chloride channel target that can be used to modulate mucin secretion by respiratory system cells.

Relevant Literature

Publications disclosing hCLCA2 include: WO 00/73438; WO99/47674; and WO99/44620; as well as Genbank accession nos. AX054697; Z24653; AF043977; AB026833; AF127980; AA726662. See also Nakanishi et al., Proc Natl Acad Sci USA 2001 Apr. 24;98(9):5175–80.

SUMMARY OF THE INVENTION

Methods and compositions for modulating mucin secretion by respiratory system cells are provided. In the subject methods, an effective amount of an hCLCA2 (or homolog thereof) modulatory agent is contacted with the cell to modulate mucin secretion, e.g., decrease or increase mucin secretion, by the cell. The subject methods find use in a variety of different applications, including the treatment of disease conditions associated with respiratory system mucin secretion, e.g., hyper- or hypo-mucin secretion. Also provided are methods of screening for respiratory system mucin secretion modulatory agents. Finally, mCLCA4 and non-human homologs thereof, as well as nucleic acid compositions encoding the same, are provided.

BRIEF DESCRIPTION OF THE FIGURES

FIG. 1A provides the nucleotide sequence of at least a portion of mCLCA4; FIG. 1B provides an alignment comparison of the nucleotide sequence for mCLCA4 and nucleotide sequence for hCLCA2; FIG. 1C provides the amino acid sequence encoded by SEQ ID NO:01 of FIG. 1A; FIG. 1D provides an alignment comparison of the protein sequence for mCLCA4 and protein sequence for hCLCA2.

FIG. 2 provides a table of the primers used in the TaqMan™ assay employed in the experimental section, infra.

FIG. 3 provides an expression profile for hCLCA1 in normal human tissues.

FIG. 26 provides a graphical representation of mouse mucin (mMUC 1, 2, 5AC) gene expression in normal mouse mucosal tissues.

DESCRIPTION OF THE SPECIFIC EMBODIMENTS

Figure 4:
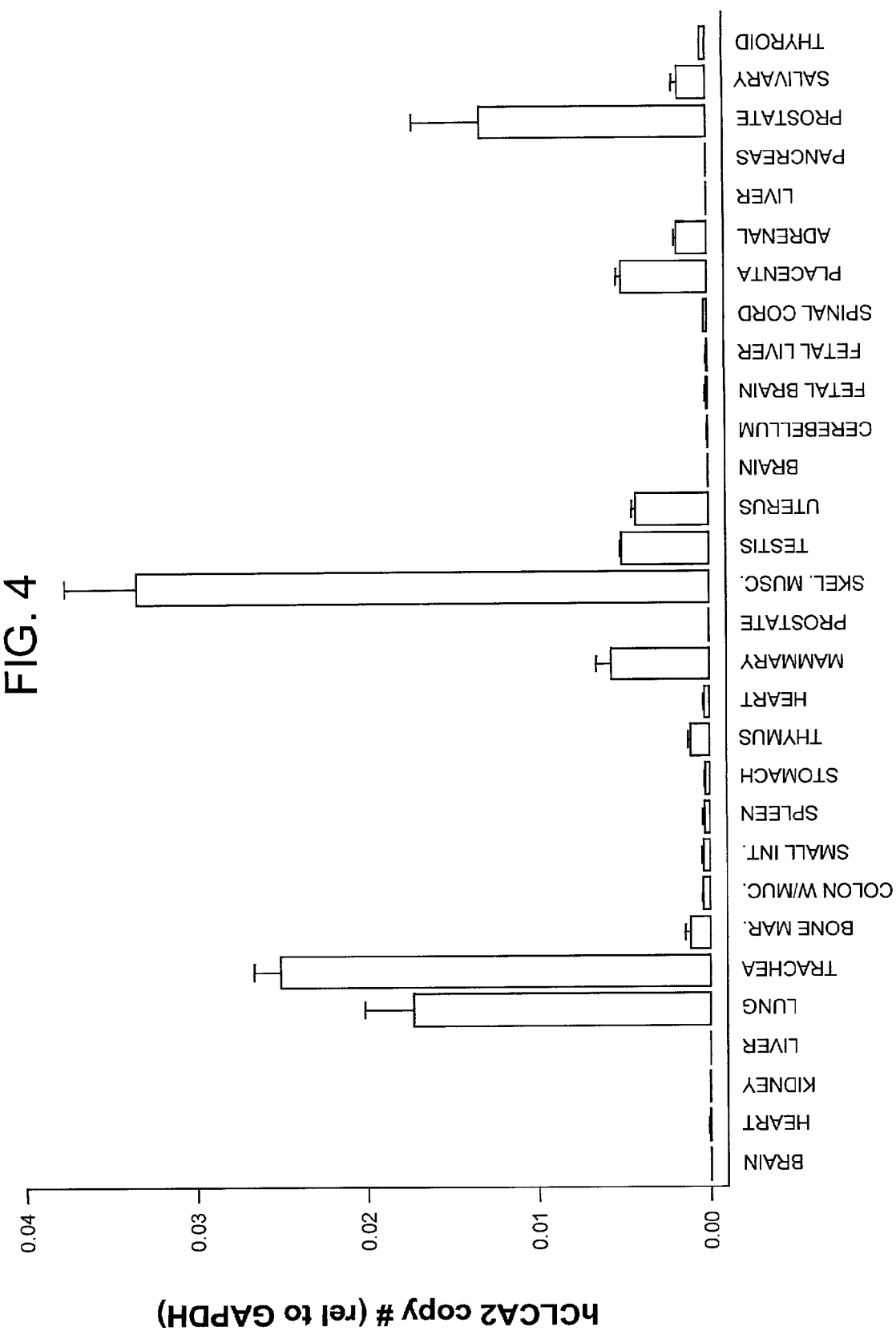
FIG. 4 provides an expression profile for hCLCA2 in normal human tissues.

Methods and compositions for modulating mucin secretion by respiratory system cells are provided. In the subject methods, an effective amount of an hCLCA2 (or homolog thereof) modulatory agent is contacted with the cell to modulate mucin secretion, e.g., decrease or increase mucin secretion, by the cell. The subject methods find use in a variety of different applications, including the treatment of disease conditions associated with respiratory system mucin secretion, e.g., hyper- or hypo-mucin secretion. Also provided are methods of screening for respiratory system mucin secretion modulatory agents. Finally, mCLCA4 and non-human homologs thereof, as well as nucleic acid compositions encoding the same, are provided. In further describing the subject invention, the subject methods will be described first, followed by a description of the subject mCLCA4 and non-human homologs thereof.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Methods

As summarized above, the subject invention provides a method of modulating mucin secretion by a respiratory system cell. By respiratory system cell is meant a cell of the respiratory system of a breathing organism, and in many embodiments a mammalian organism. Respiratory cells of interest are cells of the respiratory system, where respiratory system includes the lungs and airways associated therewith, including the trachea and bronchi, etc. Of particular interest are mucin secreting respiratory system cells, particularly cells which secrete mucins that form mucus, which cells include goblet cells, gland cells, and the like, of the respiratory system. In certain embodiments, the target cells are human cells that secrete human mucins, particularly gel forming human mucins, including but not limited to: hMUC2, hMUC4, hMUC5AC, hMUC5B, and hMUC6; where particular human mucins of interest include: hMUC4, hMUC5AC, hMUC5B, etc. In certain embodiments, the target cells are mouse cells that secrete mouse mucins, particularly gel forming mouse mucins, including but not limited to: mMUC5AC, mMUC5B and the like, where specific mucins of interest include mMUC5AC, etc.

As the subject methods are methods of modulating mucin secretion in target cells, they are methods of changing the mucin secretion of target cells, i.e., the amount of mucin secreted by target cells. As such, in certain embodiments the methods are methods of increasing or enhancing mucin secretion by target cells. In other embodiments, the methods are methods of decreasing or inhibiting mucin secretion by target cells.

In practicing the subject methods, the target respiratory system cell(s) is contacted with an amount of a CLCA2 modulatory agent effective to modulate, e.g., enhance or decrease, mucin secretion by the target cell. By CLCA2 modulatory agent is meant an agent that alters the activity of a CLCA2 protein of the target cell. Target CLCA2 proteins are hCLCA2 and homologs thereof, particularly functional homologs thereof, e.g., mCLCA4, etc. By functional homolog thereof is meant that the homolog has substantially the same mucin secretion modulatory activity, particularly respiratory system cell mucin secretion modulatory activity, as hCLCA2. In many embodiments, the subject homologs are proteins whose amino acid sequence is at least about 55%, usually at least about 75% and more usually at least about 90% identical and/or at least about 60% similar, usually at least about 75% and more usually at least about 90% similar over at least a substantial portion of its length, e.g., at least about 50%, usually at least about 75% and more usually at least about 90%, and often at least about 95% and higher, with the amino acid sequence of hCLCA2, and in many embodiments with the sequence of hCLCA2 as reported in Genbank Accession Nos. AX054697, AF043977, AB026833, AF127980 and Z24653. Unless noted otherwise, sequence identity and similarity is determined using Genetics Computer Group (GCG) GAP alignment program (parameters: Gap Weight 8, Length Weight: 2). (GAP was originally written for GCG Version 1.0 by Paul Haeberli from a careful reading of the Needleman and Wunsch (J. Mol. Biol. 48; 443–453 (1970)) and the Smith and Waterman (Adv. Appl. Math. 2; 482–489 (1981)) papers. Specific agents of interest include, but are not limited to: hCLCA2 modulatory agents and mCLCA4 modulatory agents.

Depending on the desired modulation, the modulatory agents may be agents that enhance the target CLCA2 activity or inhibit the target CLCA2 activity. By target CLCA2 activity is meant activity that affects mucin secretion, e.g., results in enhanced or inhibited mucin secretion.

A wide variety of different types of agents may be employed in the subject methods, including, but not limited to: small organic molecules, nucleic acids, proteins, etc. As such, naturally occurring or synthetic small molecule compounds of interest include numerous chemical classes, though typically they are organic molecules, preferably small organic compounds having a molecular weight of more than 50 and less than about 2,500 daltons. In certain embodiments the agents comprise functional groups necessary for structural interaction with proteins, particularly hydrogen bonding, and typically include at least an amine, carbonyl, hydroxyl or carboxyl group, preferably at least two of the functional chemical groups. The agents often comprise cyclical carbon or heterocyclic structures and/or aromatic or polyaromatic structures substituted with one or more of the above functional groups. Agents are also found among biomolecules including peptides, saccharides, fatty acids, steroids, purines, pyrimidines, derivatives, structural analogs or combinations thereof.

Also of interest as active agents are antibodies that modulate, e.g., inhibit, the target CLCA2 activity in the host. Suitable antibodies are obtained by immunizing a host animal with peptides comprising all or a portion of the target protein, e.g. a CLCA2 protein, such as hCLCA2, mCLCA4, etc. Suitable host animals include mouse, rat sheep, goat, hamster, rabbit, etc. The origin of the protein immunogen may be mouse, human, rat, monkey, etc. The host animal will generally be a different species than the immunogen, e.g. human CLCA2 used to immunize mice, etc.

The immunogen may comprise the complete protein, or fragments and derivatives thereof. Preferred immunogens comprise all or a part of a CLCA2, where these residues contain the post-translation modifications, such as glycosylation, found on the native target protein. Immunogens comprising the extracellular domain are produced in a variety of ways known in the art, e.g. expression of cloned genes using conventional recombinant methods, isolation from HEC, etc.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using CLCA2 bound to an insoluble support, protein A sepharose, etc.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')₂ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

In yet other embodiments of the invention, the active agent is an agent that modulates, and generally decreases or down regulates, the expression of the gene encoding the target protein in the host. For example, antisense molecules can be used to down-regulate expression of the target CLCA2, e.g., hCLCA2, mCLCA4 etc., in cells. The antisense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH₂-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43–56.

In certain embodiments, the agent is an agent that inhibits the target CLCA2 activity, thereby inhibiting or reducing mucin secretion by the target cell. In these embodiments, the agents are generally CLCA2 antagonists. An agent is considered to be a CLCA2 antagonist if it affects CLCA2 activity in a manner that results in a decrease in mucin secretion by at least about 5%, usually by at least about 10% and more usually by at least about 25%, as compared to a control (e.g. a target cell that has not been contacted with the antagonist). Antagonists of interest include a wide variety of agents, including, but not limited to: small organic molecules, nucleic acids, proteins, etc., where specific types of antagonist agents include those selected from the different types of candidate agents described in greater detail supra and infra with respect to screening assays. Specific inhibitory agents of interest include, but are not limited to: known calcium activated chloride channel (CLCA) inhibitors, such as diisothiocyanatostilbene disulphonic acid (DIDS); dithiothreitol (DTT); niflumic acid (NFA); tamoxifen and the like, (see e.g., Am J Physiol 1999 June;276(6 Pt 1):C1261–70; J Biol Chem 1998 Nov. 27; 273(48):32096–101; and Pflugers Arch 1998 May; 435(6):796–803); etc. The agent may be selective for chloride channels, selective for calcium activated chloride channels, selective for specific calcium activated chloride channels, e.g., hCLCA2 or homologs thereof, such as mCLCA4, as may be desired. Agents selective for specific calcium activated chloride channels may be readily identified using the screening assays described supra.

In certain embodiments, the agent is an agent that enhances the target CLCA2 activity, thereby enhancing or increasing mucin secretion by the target cell. In these embodiments, the agents are generally CLCA2 agonists. An agent is considered to be a CLCA2 agonist if it affects CLCA2 activity in a manner that results in an increase in mucin secretion by at least about 5%, usually by at least about 10% and more usually by at least about 25%, as compared to a control (e.g. a target cell that has not been contacted with the antagonist). Agonists of interest include a wide variety of agents, including, but not limited to: small organic molecules, nucleic acids, proteins, etc., where specific types of agonist agents include those selected from the different types of candidate agents described in greater detail supra and infra with respect to screening assays.

As mentioned above, the amount of agent that is contacted with the cell is an amount that is effective to cause the desired modulation, e.g., increase or decrease, of mucin secretion from the cell. The amount of change may vary, but is generally at least about 5%, usually at least about 10% and more usually at least about 25% in magnitude. Depending on the nature of the specific modulatory agent, the effective amount may vary, but can be readily determined empirically by those of skill in the art. In many embodiments, the effective amount typically ranges from about 1–500 mg daily, preferably from about 1–100 mg daily, and most preferably from about 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved.

The target cell with which the CLCA2 modulatory agent is contacted during practice of the subject methods may be in an in vitro or in vivo environment, i.e., it may be part of an in vitro or in vivo system. Examples of in vitro environments include cell cultures, etc., while examples of in vivo environments include living organisms, e.g., mammals such as humans, mice, etc.

The CLCA2 modulatory agent is contacted with the target cell(s) using any convenient protocol. The particular protocol employed necessarily depends on the nature of the agent and the environment of the target cell, e.g., whether the target cell is present in an in vitro or in vivo system. For in vitro systems, the modulatory agent is introduced into the in vitro environment of the target cell such that the desired contact occurs, e.g., a composition of the modulatory agent such as an aqueous composition is introduced into a cell culture medium of the target cells, e.g., is pipetted or otherwise dispensed into the culture medium.

Where the target cell(s) is present in an in vivo environment or system, e.g., the target cells are present in a living organism (for example the target cells are goblet cells of the respiratory system such as the tracheal epithelium), contact is generally achieved via administration of the modulatory agent to the host in which the target cell or cells are found. In the subject methods, the modulatory agent may be administered to the host using any convenient means capable of resulting in the desired modulation of CLCA2 activity, e.g., desired reduction or increase in hCLCA2 or mCLCA4 affected mucin secretion. Thus, the agent can be incorporated into a variety of formulations for therapeutic administration. More particularly, the agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may also be used for intramuscular administration, as described by Furth et al. (1992), Anal Biochem 205:365–368. The DNA may be coated onto gold microparticles, and delivered intradermally by a particle bombardment device, or "gene gun" as described in the literature (see, for example, Tang et al. (1992), Nature 356:152–154), where gold microprojectiles are coated with the therapeutic DNA, then bombarded into skin cells.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Other suitable pharmaceutical carriers and their formulations are described in Martin (ed.) (1995) Remington: The Science and Practice of Pharmacy, 19th ed., Mack Publishing Company, Easton, Pa.

In general, the modulators are administered in a therapeutically effective amount by any of the accepted modes of administration for agents that serve similar utilities, where representative modes are described above. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able to ascertain a therapeutically effective amount of the compounds of the present invention for a given disease. For example frequency of dosing can be 1, 2, 3, or multiple times per day.

Methods of Treating Disease Conditions

The subject methods find use in, among other applications, the treatment of disease conditions associated with respiratory system cell mucin secretion, including respiratory system cell mucin hypersecretion and respiratory system cell mucin hyposecretion. Disease conditions associated with mucin hypersecretion in the respiratory system which are amenable to treatment with the subject methods include, but are not limited to: chronic bronchitis; asthma; COPD; bronchiectasis; and inappropriate mucus secretion resulting from cystic fibrosis; and the like. Disease conditions associated with mucin hyposecretion include, but are not limited to: keratoconjunctivitis sicca (KCS or dry eye), 'Sjogren's Syndrome', general dry mouth (a common side effect with anticholinergic drugs); stripping of mucosa associated with ulcerative colitis and Crohn's disease; and the like.

By treatment is meant at least an amelioration of the symptoms associated with the mucin secretion associated pathological condition afflicting the host, where amelioration is used in a broad sense to refer to at least a reduction in the magnitude of a parameter, e.g. symptom, associated with the pathological condition being treated, such as excess mucus, insufficient mucus, etc. As such, treatment also includes situations where the pathological condition, or at least symptoms associated therewith, is completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Screening Assays

Also provided are screening assays for agents having CLCA2 modulatory activity, i.e., for determining whether a candidate agent has CLCA2 modulatory activity or identifying the CLCA2 modulatory activity of a candidate agent.

A variety of methods are provided for determining whether a compound can modulate the activity of the target CLCA2. In many embodiments, the methods include contacting CLCA2 (or functional homologs thereof, such as mCLCA4 described infra) or fragments thereof, with the candidate compound under suitable conditions and subsequently determining if the compound modulates the activity of the target CLCA2 or functional homolog thereof. The candidate compound can be a candidate agonist or antagonist of CLCA2 activity. CLCA2, functional homologs or fragments thereof can be expressed on a cell or tissue, endogenously or recombinantly, or immobilized by attachment to a solid substrate, e.g., nitrocellulose or nylon membrane, glass, beads, etc.

Transcription based assays that identify signals that modulate the activity of cell surface proteins, e.g., receptors, ion channels, etc., may be used to screen candidate compounds for their ability to stimulate reporter gene product expression and their potential to stimulate the expression of CLCA2 or the functional homolog thereof, e.g., mCLCA4.

One method for identifying compounds that stimulate CLCA2 promoter-controlled reporter gene expression comprises introducing into a cell a DNA construct that comprises a CLCA2 promoter operably linked to a reporter gene, mixing a test compound with the cell and measuring the level of expression of reporter gene product. A change in the level of expression of the reporter gene product indicates that the compound is capable of modulating the level of CLCA2 expression, or expression of the functional homolog thereof being studied, e.g., mCLCA4. The reporter gene construct is preferably stably integrated into the chromosomal DNA of the cell, but is also functional for the purposes disclosed herein in the form of an extrachromosomal element. The cell may be a eukaryotic cell, or any cell that contains the elements needed to express a structural gene under the regulatory influence of a mammalian gene promoter.

Other transcription based assays are well known in the art. (See, e.g., Zlokarnik, et al. (1998) Science 279:84–88; Siverman, supra; and Gonzalez and Negulescu, (1998) Curr.

Opin. Biotechnol. 9:624–631.) These transcription based assays assess the intracellular transduction of an extracellular signal using recombinant cells that are modified by introduction of a reporter gene under the control of a regulatable promoter. In order to express a biologically active CLCA2, the nucleotide sequences encoding CLCA2 or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding CLCA2 and appropriate transcriptional and translational control elements. These methods include in vitro recombinant DNA techniques, synthetic techniques, and in vivo genetic recombination. (See, e.g., Sambrook, J. et al. (1989) Molecular Cloning, A Laboratory Manual, Cold Spring Harbor Press, Plainview, N.Y.; and Ausubel, F. M. et al. (1989) Current Protocols in Molecular Biology, John Wiley & Sons, New York, N.Y.)

A variety of expression vector/host systems may be utilized to contain and express sequences encoding CLCA2 or the functional homolog thereof, e.g., mCLCA4. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus) or with bacterial expression vectors (e.g., Ti or pBR322 plasmids); or animal cell systems. The invention is not limited by the host cell employed.

A two-hybrid system-based approach can also be employed for compound screening, small molecule identification, and drug discovery. The underlying premise of the two-hybrid system, originally described in yeast by Fields and Song (1989) Nature 340:245–246, provides a connection between a productive protein-protein or protein-compound interaction pair of interest and a measurable phenotypic change in yeast. A reporter cassette containing an up-stream activation sequence which is recognized by a DNA binding domain, is operationally linked to a reporter gene, which when expressed under the correct conditions will generate a phenotypic change. The original two-hybrid system has recently been modified for applicability in high-throughput compound screening. (See, e.g., Ho et al. (1996) Nature 382:822–826; Licitra and Liu (1996) Proc. Natl. Acad. Sci. USA 93:12817–12821; and Young et al. (1998) Nature Biotech. 16:946–950.)

Assays for identifying compounds that modulate ion channel activity are practiced by measuring the ion channel activity when a cell expressing the ion channel of interest, or fragments thereof, is exposed to a solution containing the test compound and an ion channel selective ion, and comparing the measured ion channel activity to the native ion channel activity of the same cell or a substantially identical control cell in a solution not containing the test compound. Methods for practicing such assays are known to those of skill in the art. (See, e.g., Mishina et al. (1985) Nature 313:364–369; and Noda, et al. Nature 322:836–828.)

Ion channel activity can be measured using methods such as electrophysiology (two electrode voltage clamp or single electrode whole cell patch clamp), guanidinium ion flux assays, toxin-binding assays, and Fluorometric Imaging Plate Reader (FLIPR) assays. (See, e.g., Sullivan, et al. (1999) Methods Mol. Biol. 114:125–133; Siegel and Isacoff (1997) Neuron 19:1–20; and Lopatin, et al. (1998) Trends Pharmacol. Sci. 19:395–398.) An "inhibitor" is defined generally as a compound, at a given concentration, that results in greater than 50% decrease in ion channel activity, preferably greater than 70% decrease in ion channel activity, more preferably greater than 90% decrease in ion channel activity.

The binding or interaction of the compound with a target, or fragments thereof, can be measured directly by using radioactively labeled compound of interest (see, e.g., Wainscott et al. (1993) Mol. Pharmacol. 43:419–426; and Loric, et al. (1992) FEBS Lett. 312:203–207) or by the second messenger effect resulting from the interaction or binding of the candidate compound. (See, e.g., Lazereno and Birdsall (1993) Br. J. Pharmacol. 109:1120–1127.) Modulation in target signaling or activity can be measured with a detectable assay, e.g., the FLIPR assay. (See, e.g., Coward, P. (1999) Anal. Biochem. 270:242–248; Sittampalam, supra; and Gonzalez and Negulescu, supra.) Activation of certain receptors, in particular, GPCRs, can be measured using a $^{35}$S-GTPγS binding assay. (See, e.g., Lazareno (1999) Methods Mol. Biol. 106:231–245.)

Alternatively, the candidate compounds can be subjected to competition screening assays, in which a known ligand, preferably labeled with an analytically detectable reagent, most preferably radioactivity, is introduced with the drug to be tested and the capacity of the compound to inhibit or enhance the binding of the labeled ligand is measured. Compounds are screened for their increased affinity and selectivity for the specific receptor or fragments thereof.

In many embodiments, the screening assays are specifically directed to the identification of agents that modulate the CLCA2, e.g., hCLCA2 or mCLCA4, activity that affects mucin secretion, particularly in the respiratory system. In these embodiments of the screening assays, the following steps are practiced: (a) contacting a CLCA2/mucin secretion model with a candidate compound; (b) observing the effect of the candidate compound on mucin secretion; and (c) deriving the candidate compound's mucin secretion modulatory activity from the observed effect.

The CLCA2/mucin secretion model may be in an in vivo or in vitro model. In vitro models of interest include, but are not limited to: cell cultures in which the cells, e.g., goblet cells, comprise both CLCA2 (or homolog thereof, e.g., mCLCA4) and mucin production/secretion elements, e.g., such that the cells secrete mucin as a function of CLCA2 activity. A representative in vitro CLCA2/mucin secretion model is the 'air-liquid interface' (ALI) system described in the Experimental Section, infra. In vivo models of interest include, but are not limited to, non-human animal models of CLCA2/mucin secretion, such as a mouse model having altered expression of the mouse homolog of hCLCA2, i.e., mCLCA4, a mouse transgenic animal of hCLCA2, etc.

Mucin secretion following candidate agent contact may be evaluated either directly or indirectly. Direct evaluation includes measuring the amount of mucin secretion from the cells of the model and comparing the amount to a control, e.g., the amount of mucin produced from an identical system that was not contacted with the candidate agent. Indirect evaluation includes measuring the expression level of one or more mucin genes, particularly mucin genes that produce mucus (e.g., gel forming mucins) upon secretion into extracellular space (e.g., hMUC5AC, hMUC5B and mMUC5AC, following contact with the candidate agent, and relating the observed expression level to the level of mucin secretion. Methods of measuring transcription level are well known to those of skill in the art, as reviewed above.

The observed mucin secretion is then used to derive the CLCA2 modulatory activity of the candidate agent, particularly the respiratory system cell CLCA2/mucin secretion modulatory activity of the candidate agent.

Diagnostics and Kits

The present invention contemplates the use of CLCA2 polynucleotides, polypeptides, and antibodies in a variety of diagnostic methods kits, particularly methods of diagnosing disease associated with respiratory system abnormal mucin secretion, such as the diseases described above which are associated with respiratory system mucin hypo- and hyper-secretion. Typically the kit will have a compartment containing either a defined CLCA2 polypeptide, polynucleotide, or a reagent which recognizes one or the other, e.g., antigen fragments or antibodies. Additionally the kit will include the reagents needed to carry out the assay in a separate compartment as well as instructions for use and proper disposal.

A variety of protocols including ELISA, RIA, and FACS for measuring CLCA2 are known in the art and provide a basis for diagnosing altered or abnormal levels of CLCA2 expression. These techniques can also be used to monitor the efficacy of therapeutic intervention on the expression of CLCA2. For example, an effective therapeutic compound will either inhibit expression of CLCA2 or induce expression of CLCA2. As noted above, a change in the expression level of CLCA2 causes a change in mucus secretion.

Normal or standard values for CLCA2 expression are established by combining body fluids or cell extracts taken from normal mammalian subjects, preferably human, with antibody to CLCA2 under conditions suitable for complex formation. The amount of standard complex formation may be quantified by various methods, but preferably by photometric means. Quantities of CLCA2 expressed in control and disease samples from biopsied tissues are compared with the standard values. Deviation between standard and subject values establishes the parameters for diagnosing disease. This method can also be employed to monitor CLCA2 expression during treatment of a subject with at least one CLCA2 modulator, in order to evaluate the progress of therapeutic treatment.

In another embodiment of the invention, the polynucleotides encoding CLCA2 may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of CLCA2 may be correlated with disease. The diagnostic assay may be used to distinguish between absence, presence, and excess expression of CLCA2, and to monitor regulation of CLCA2 levels during therapeutic intervention, as noted above.

In one aspect, hybridization with PCR probes which are capable of detecting polynucleotide sequences, including genomic sequences, encoding CLCA2 or closely related molecules, may be used to identify nucleic acid sequences which encode CLCA2. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding CLCA2 alleles, or related sequences.

Probes may also be used for the detection of related sequences, and should preferably contain at least 50% of the nucleotides from any of the CLCA2 encoding sequences. The hybridization probes of the subject invention may be DNA or RNA, including genomic sequence including promoter, enhancer elements, and introns of the naturally occurring CLCA2.

Means for producing specific hybridization probes for DNAs encoding CLCA2 include the cloning of nucleic acid sequences encoding CLCA2 or CLCA2 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}P$ or $^{35}S$, or enzymatic labels, such as alkaline phosphatase coupled to the probe via avidin/biotin coupling systems, and the like.

Polynucleotide sequences encoding CLCA2 may be used for the diagnosis of conditions or disorders that are associated with expression of CLCA2, e.g., disease states associated with mucus secretion disorders, particularly mucus secretion disorders of the respiratory system.

In order to provide a basis for the diagnosis of disease associated with expression of CLCA2, a normal or standard profile for expression is established. This may be accomplished by combining body fluids or cell extracts taken from normal subjects, either animal or human, with a polynucleotide sequence, or a fragment thereof, which encodes CLCA2, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from subjects who are symptomatic for disease. Deviation between standard and subject values is used to establish the presence of disease.

Once a disease is established and a treatment protocol is initiated, hybridization assays may be repeated on a regular basis to evaluate whether the level of expression of CLCA2 in the subject begins to approximate that which is observed in the normal subject. The results obtained from successive assays may be used to show the efficacy of treatment over a period ranging from several hours to several days to several months.

Additional diagnostic uses for oligonucleotides designed from the sequences encoding CLCA2 may involve the use of PCR. Such oligomers may be chemically synthesized, generated enzymatically, or produced in vitro. Oligomers will preferably consist of two nucleotide sequences, one with sense orientation (5' to 3') and another with antisense (3' to 5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of CLCA2 include radiolabeling or biotinylating nucleotides, coamplification of a control nucleic acid, and standard curves onto which the experimental results are interpolated. (See, e.g., Melby, P. C. et al. (1993) J. Immunol. Methods, 159:235–244; and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences that encode CLCA2 may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructs, or single chromosome cDNA libraries. (See, e.g., Price, C. M. (1993) Blood Rev. 7:127–134, and Trask, B. J. (1991) Trends Genet. 7:149–154.)

Fluorescent in situ hybridization (FISH) may be correlated with other physical chromosome mapping techniques and genetic map data. (See, e.g., Verma et al. (1988) Human Chromosomes: A Manual of Basic Techniques, Pergamon Press, New York, N.Y.) Examples of genetic map data can be found in various scientific journals or at Online Mendelian Inheritance in Man (OMIM). Correlation between the location of the gene encoding CLCA2 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region (see, e.g., Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In addition, the subject nucleic acid sequences find use in 'Single Nucleotide Polymorphism' (SNP) analysis to confirm an association of hCLCA2 and other CLCAs with human hypersecretory diseases. For a description of the SNP approach, see: Riley J H, Allan C J, Lai E, Roses A. Pharmacogenomics 2000 February; 1(1):39–47. 'The use of single nucleotide polymorphisms in the isolation of common disease genes' and Schork N J, Fallin D, Lanchbury J S., Clin Genet 2000 October; 58(4):250–64. "Single nucleotide polymorphisms and the future of genetic epidemiology."

Nonhuman Homologs of CLCA2

Also provided by the subject invention are nonhuman homologs of hCLCA2, as well as nucleic acid compositions encoding the same and related inventions.

Polypeptide Compositions

Nonhuman homologs of hCLCA2, as well as polypeptide compositions related thereto, are provided. The term polypeptide composition as used herein refers to both the full length protein, as well as portions or fragments thereof. A specific nonhuman hCLCA2 homolog of interest is mCLCA4. mCLCA4 includes an amino acid sequence as shown in FIG. 1C and identified as SEQ ID NO:02. FIG. 1D shows a comparison of the predicted protein sequence for the novel mouse ion channel mCLCA4 with the predicted protein sequence of the known human homolog hCLCA2.

Also provided by the subject invention are related polypeptide compositions. The term polypeptide composition as used herein refers to both the full length proteins as well as portions or fragments thereof. Also included in this term are variations of the naturally occurring proteins, where such variations are homologous or substantially similar to the naturally occurring protein, be the naturally occurring protein the mouse protein, or protein from some other species which naturally expresses a nonhuman homolog of hCLCA2, usually a mammalian species. A candidate homologous protein is substantially similar to the mCLCA4 protein of the subject invention, and therefore is an mCLCA4 homolog or non-human homolog of hCLCA2 of the subject invention, if the candidate protein has a sequence that has at least about 35%, usually at least about 45% and more usually at least about 60% sequence identity with mCLCA4, as determined using MegAlign, DNAstar (1998) clustal algorithm as described in D. G. Higgins and P. M. Sharp, "Fast and Sensitive multiple Sequence Alignments on a Microcomputer," (1989) CABIOS, 5: 151–153. (Parameters used are ktuple 1, gap penalty 3, window, 5 and diagonals saved 5). In the following description of the subject invention, the term "nonhuman hCLCA2 homolog" is used to refer not only to mCLCA4, but also to homologs thereof expressed in non-human species, e.g. rat and other mammalian species.

Also provided are proteins that are substantially identical to the disclosed proteins, where by substantially identical is meant that the protein has an amino acid sequence identity to the sequence of one of the disclosed proteins of at least about 60%, usually at least about 65% and more usually at least about 70%. In many preferred embodiments, the sequence identity is at least about 90%, usually at least about 95% and more usually at least about 99% over the entire length of the protein.

The nonhuman hCLCA2 homologs of this invention are chloride channels, preferably chloride channels that affect mucin secretion, and more preferably chloride channels that affect mucin secretion in respiratory system cells.

In addition to the proteins described above, homologs or proteins (or fragments thereof) from other species, i.e. other animal species, are also provided, where such homologs or proteins may be from a variety of different types of species, usually mammals, e.g. rodents, such as mice, rats; domestic animals, e.g. horse, cow, dog, cat; and humans. By homolog is meant a protein having at least about 35%, usually at least about 40% and more usually at least about 60% amino acid sequence identity with mCLCA4 as identified above (i.e. with a protein having the amino acid sequence of SEQ ID NO:02), where sequence identity is determined as described supra.

The proteins of the subject invention are present in a non-naturally occurring environment, e.g. they are separated from their naturally occurring environment. In certain embodiments, the subject proteins are present in a composition that is enriched for the subject protein as compared to its naturally occurring environment. For example, purified protein is provided, where by purified is meant that the protein is present in a composition that is substantially free of non-CLCA2 proteins, where by substantially free is meant that less than 90%, usually less than 60% and more usually less than 50% of the composition is made up of non-CLCA2 proteins. The proteins of the subject invention may also be present as an isolate, by which is meant that the protein is substantially free of other proteins and other naturally occurring biologic molecules, such as oligosaccharides, polynucleotides and fragments thereof, and the like, where the term "substantially free" in this instance means that less than 70%, usually less than 60% and more usually less than 50% of the composition containing the isolated protein is some other naturally occurring biological molecule. In certain embodiments, the proteins are present in substantially pure form, where by "substantially pure form" is meant at least 95%, usually at least 97% and more usually at least 99% pure.

In addition to the naturally occurring proteins, polypeptides which vary from the naturally occurring proteins are also provided, e.g. mCLCA4 polypeptides. By mCLCA4 polypeptide is meant an amino acid sequence encoded by an open reading frame (ORF) of the gene encoding the mCLCA4, described in greater detail below, including the full length protein and fragments thereof, particularly biologically active fragments and/or fragments corresponding to functional domains, and the like; and including fusions of the subject polypeptides to other proteins or parts thereof. Fragments of interest will typically be at least about 10 aa in length, usually at least about 50 aa in length, and may be as long as 300 aa in length or longer, but will usually not exceed about 1000 aa in length, where the fragment will have a stretch of amino acids that is identical to the subject protein of at least about 10 aa, and usually at least about 15 aa, and in many embodiments at least about 50 aa in length. In certain embodiments, the fragments preferably include at least a substantial portion of the wild type protein mCLCA4 protein, where by substantial amount is meant at least 50%, usually at least 60% and more usually at least 70% of the length of the mCLCA4 protein, wherein in many embodiments the percentage may be much higher, e.g. 75, 80, 85, 90 or 95% or higher, e.g. 99%.

The subject proteins and polypeptides may be obtained from naturally occurring sources or synthetically produced. For example, the proteins may be derived from biological sources which express the proteins, such as respiratory cells, e.g., goblet cells, and the like. The subject proteins may also be derived from synthetic means, e.g. by expressing a recombinant gene encoding protein of interest in a suitable host, as described in greater detail below. Any convenient protein purification procedures may be employed, where suitable protein purification methodologies are described in Guide to Protein Purification, (Deuthser ed.) (Academic Press, 1990). For example, a lysate may prepared from the original source, e.g. goblet cells or the expression host, and purified using HPLC, exclusion chromatography, gel electrophoresis, affinity chromatography, and the like.

Nucleic Acid Compositions

Also provided are nucleic acid compositions encoding mCLCA4 proteins or fragments thereof, as well as the mCLCA4 homologs of the present invention. By nucleic acid composition is meant a composition comprising a sequence of DNA having an open reading frame that encodes a mCLCA4 polypeptide of the subject invention, i.e. an mCLCA4 gene, and is capable, under appropriate conditions, of being expressed as mCLCA4. Also encompassed in this term are nucleic acids that are homologous or substantially similar or identical to the nucleic acids encoding mCLCA4 proteins. Thus, the subject invention provides genes encoding the mCLCA4 proteins of the subject invention and homologs thereof. The mCLCA4 coding sequence includes the sequence shown in FIG. 1A, where the nucleic acid sequence shown in FIG. 1A is identified as SEQ ID NO:01, infra.

The source of homologous genes may be any species, e.g., primate species; rodents, such as rats and mice, canines, felines, bovines, ovines, equines, yeast, nematodes, etc. Between mammalian species, e.g., mouse and rats, homologs typically have substantial sequence similarity, e.g. at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403–10 (using default settings, i.e. parameters w=4 and T=17). The sequences provided herein are essential for recognizing mCLCA4 related and homologous proteins, and the nucleic acids encoding the same, in database searches. Of particular interest in certain embodiments are nucleic acids of substantially the same length (e.g., at least 50%, often at least 75% and more often at least 90% of the same length) as the nucleic acid identified as SEQ ID NO:01, and have sequence identity to one of these sequences of at least about 90%, usually at least about 95% and more usually at least about 99% over the entire length of the nucleic acid.

Nucleic acids encoding the proteins and polypeptides of the subject invention may be cDNA or genomic DNA or a fragment thereof. The term "CLCA4 gene" shall be intended to mean the open reading frame encoding the specific proteins and polypeptides, and introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding an MPTS protein.

A genomic sequence of interest comprises the nucleic acid present between the initiation codon and the stop codon, as defined in the listed sequences, including all of the introns that are normally present in a native chromosome. It may further include 5' and 3' un-translated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject mCLCA4 protein. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt.

The subject genes are isolated and obtained in substantial purity, generally as other than an intact chromosome. Usually, the DNA will be obtained substantially free of other nucleic acid sequences that do not include an mCLCA4 gene sequence or fragment thereof, generally being at least about 50%, usually at least about 90% pure and are typically "recombinant", i.e. flanked by one or more nucleotides with which it is not normally associated on a naturally occurring chromosome.

Preparation of mCLCA4 Polypeptides

In addition to the plurality of uses described in greater detail in following sections, the subject nucleic acid compositions find use in the preparation of all or a portion of the mCLCA4 polypeptides, as described above. The provided polynucleotide (e.g., a polynucleotide having a sequence of SEQ ID NO:01), the corresponding cDNA, or the full-length gene is used to express a partial or complete gene product. Constructs of polynucleotides having a sequence of SEQ ID NO: 01 can be generated synthetically. Alternatively, single-step assembly of a gene and entire plasmid from large numbers of oligodeoxyribonucleotides is described by, e.g., Stemmer et al., *Gene (Amsterdam)* (1995) 164(1):49–53. In this method, assembly PCR (the synthesis of long DNA sequences from large numbers of oligodeoxyribonucleotides (oligos)) is described. The method is derived from DNA shuffling (Stemmer, *Nature* (1994) 370:389–391), and does not rely on DNA ligase, but instead relies on DNA polymerase to build increasingly longer DNA fragments during the assembly process. Appropriate polynucleotide constructs are purified using standard recombinant DNA techniques as described in, for example, Sambrook et al., *Molecular Cloning: A Laboratory Manual, 2nd Ed.*, (1989) Cold Spring Harbor Press, Cold Spring Harbor, N.Y., and under current regulations described in United States Dept. of HHS, National Institute of Health (NIH) Guidelines for Recombinant DNA Research.

Polynucleotide molecules comprising a polynucleotide sequence provided herein are propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. The gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, an mCLCA4 encoding polynucleotide, e.g. as set forth in SEQ ID NO: 01, is linked to a regulatory sequence as appropriate to obtain the desired expression properties. These can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject MPTS gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

The mCLCA4 proteins and polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, HEK 293, CHO, *Xenopus Oocytes*, etc., may be used as the expression host cells. In some situations, it is desirable to express the gene in eukaryotic cells, where the expressed protein will benefit from native folding and post-translational modifications. Small peptides can also be synthesized in the laboratory. Polypeptides that are subsets of the complete protein sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433;

DeBoer et al., *Proc. Natl. Acad. Sci. (USA)* (1983) 80:21–25; and Siebenlist et al., *Cell* (1980) 20:269.

Yeast. Expression systems in yeast include those described in Hinnen et al., *Proc. Natl. Acad. Sci. (USA)* (1978) 75:1929; Ito et al., *J. Bacteriol* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154:737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284–289; Tilburn et al., *Gene* (1983) 26:205–221; Yelton et al., *Proc. Natl. Acad. Sci. (USA)* (1984) 81:1470–1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765–776; Miller et al., *Ann. Rev. Microbiol.* (1988) 42:177; Carbonell et al., *Gene* (1988) 73:409; Maeda et al., *Nature* (1985) 315:592–594; Lebacq-Verheyden et al., *Mol. Cell. Biol.* (1988) 8:3129; Smith et al., *Proc. Natl. Acad Sci. (USA)* (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47–55, Miller et al., *Generic Engineering* (1986) 8:277–279, and Maeda et al., *Nature* (1985) 315:592–594.

Mammalian Cells. Mammalian expression is accomplished as described in Dijkema et al., *EMBO J.* (1985) 4:761, Gorman et al., *Proc. Natl. Acad. Sci. (USA)* (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE Pat. No. 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated in the cell to which the gene is native. For example, an endogenous gene of a cell can be regulated by an exogenous regulatory sequence as disclosed in U.S. Pat. No. 5,641,670.

Uses of the Subject Polypeptide and Nucleic Acid Compositions

The subject polypeptide and nucleic acid compositions find use in a variety of different applications. General applications of interest include: the identification of mCLCA4 homologs; as a source of novel promoter elements; the identification of mCLCA4 expression regulatory factors; as probes and primers in hybridization applications, e.g. PCR; the identification of expression patterns in biological specimens; the preparation of cell or animal models for mCLCA4 function; the preparation of in vitro models for mCLCA4 function; etc.

Homologs of the subject genes are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions. Other stringent hybridization conditions are known in the art and may also be employed to identify nucleic acids of this particular embodiment of the invention.

Nucleic acids having a region of substantial identity to the provided sequences, e.g. allelic variants, genetically altered versions of the gene, etc., bind to the provided sequences under stringent hybridization conditions. By using probes, particularly labeled probes of DNA sequences, one can isolate homologous or related genes.

The sequence of the 5' flanking region may be utilized for promoter elements, including enhancer binding sites, that provide for developmental regulation in tissues where the subject mCLCA4 gene is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995), *Mol. Med.* 1:194–205; Mortlock et al. (1996), *Genome Res.* 6:327–33; and Joulin and Richard-Foy (1995), *Eur. J. Biochem.* 232: 620–626.

The regulatory sequences may be used to identify cis acting sequences required for transcriptional or translational regulation of mCLCA4 gene expression, especially in different tissues or stages of development, and to identify cis acting sequences and trans-acting factors that regulate or mediate mCLCA4 gene expression. Such transcription or translational control regions may be operably linked to an mCLCA4 gene in order to promote expression of wild type or altered mCLCA4 or other proteins of interest in cultured cells, or in embryonic, fetal or adult tissues, and for gene therapy.

Small DNA fragments are useful as primers for PCR, hybridization screening probes, etc. Larger DNA fragments, i.e. greater than 100 nt are useful for production of the encoded polypeptide, as described in the previous section. For use in geometric amplification reactions, such as geometric PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of mCLCA4 gene expression in the sample.

The sequence of an mCLCA4 gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993), *Biotechniques* 14:22; Barany (1985), *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al., *Molecular Cloning: A Laboratory Manual*, CSH Press 1989, pp. 15.3–15.108; Weiner et al. (1993), *Gene* 126:35–41; Sayers et al. (1992), *Biotechniques* 13:592–6; Jones and Winistorfer (1992), *Biotechniques* 12:528–30; Barton et al. (1990), *Nucleic Acids Res* 18:7349–55; Marotti and Tomich (1989), *Gene Anal. Tech.* 6:67–70; and Zhu (1989), *Anal Biochem* 177:120–4. Such mutated genes may be used to study structure-function relationships of an MPTS protein, or to alter properties of the protein that affect its function or regulation.

The subject nucleic acids can be used to generate transgenic, non-human animals or site specific gene modifications in cell lines. Transgenic animals may be made through homologous recombination, where the endogenous locus is altered. Alternatively, a nucleic acid construct is randomly integrated into the genome. Vectors for stable integration include plasmids, retroviruses and other animal viruses, YACs, and the like.

The modified cells or animals are useful in the study of mCLCA4 function and regulation. Of interest is the use of the subject genes to construct transgenic animal models of mCLCA4/hCLCA2 related disease conditions, including mucin secretion related disease conditions, e.g. disease conditions associated with mucin secretion in the respiratory system, such as the hypo and hyper secretion diseases discussed supra. Thus, transgenic animal models of the subject invention include models where the endogenous mCLCA4 gene expression profile is modulated or altered, e.g., knockouts in which expression of endogenous mCLCA4 is at least reduced if not eliminated, modifications where expression of mCLCA4 is enhanced, etc. One may also provide for expression of the gene or variants thereof in cells or tissues where it is not normally expressed, at levels not normally present in such cells or tissues.

DNA constructs for homologous recombination will comprise at least a portion of the mCLCA4 gene of the subject invention, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on aggrecanase activity.

mCLCA4 Antibodies

Also provided are antibodies that bind to mCLCA4 proteins and homologs thereof. Suitable antibodies are obtained by immunizing a host animal with peptides comprising all or a portion of the mCLCA4. Suitable host animals include rat, sheep, goat, hamster, rabbit, etc. The origin of the protein immunogen may be mouse, rat, monkey etc. The host animal will generally be a different species than the immunogen, e.g. mCLCA4 used to immunize rabbit, etc.

The immunogen may comprise the complete protein, or fragments and derivatives thereof. Preferred immunogens comprise all or a part of mCLCA4, where these residues contain the post-translation modifications, such as glycosylation, found on the native target protein. Immunogens comprising the extracellular domain are produced in a variety of ways known in the art, e.g. expression of cloned genes using conventional recombinant methods, isolation from HEC, etc.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using MPTS bound to an insoluble support, protein A sepharose, etc.

The antibody may be produced as a single chain, instead of the normal multimeric structure. Single chain antibodies are described in Jost et al. (1994) J.B.C. 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

The following examples are offered by way of illustration and not by way of limitation.

Experimental

EXAMPLE 1

Expression of all Known Human CLCAs and Mucins in Normal Tissues, Including Normal Lung To determine if there is another functional homolog of mCLCA3 in humans, a quantitative 'real-time' RT-PCR (Taqman™) assay was developed for all known human CLCAs (CLCA1, 2, 3, 4). The protocol for this assay is described in the user manual for the Taqman Gold RT-PCR kit, sold by Perkin Elmer Biosystems. Using literature sequences as references, standard curves of each cloned gene were created to allow us to accurately quantify both relative and absolute levels of CLCA gene expression (mRNA levels) in our normal human tissues. See Table I appearing in FIG. 2 for a description of all qRT-PCR primers and Taqman probes for each human and mouse gene evaluated. We obtained tissues from a commercial supplier (Clontech); these were typically pooled samples taken from trauma victims (i.e., car accidents) who were presumed healthy at the time of death. For results, see hCLCA1, FIG. 3; hCLCA2, FIG. 4; hCLCA3, FIG. 5; hCLCA4, FIG. 6.

Figure 7:
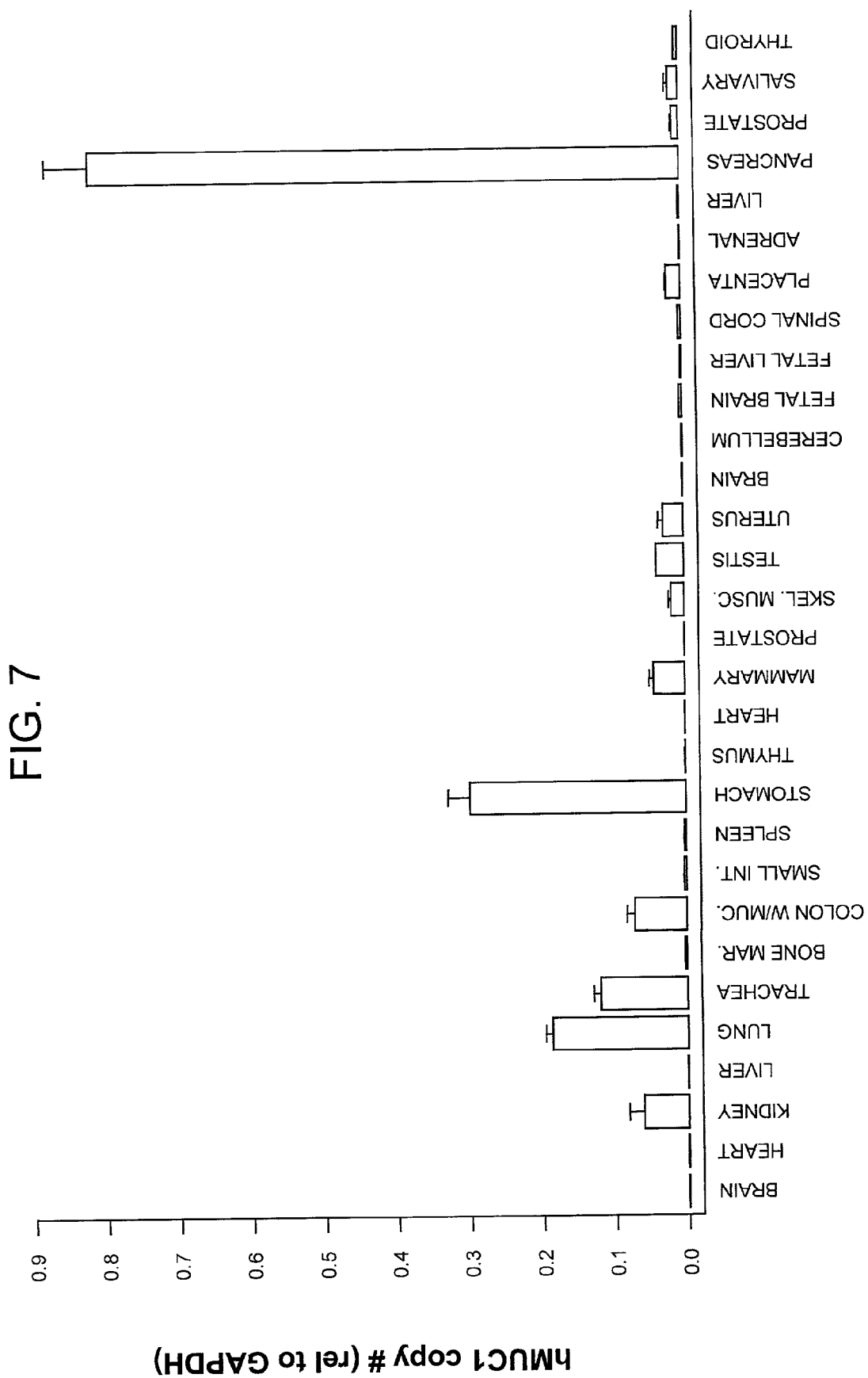
FIG. 7 provides an expression profile for hMUC1 in normal human tissues.
Figure 8:
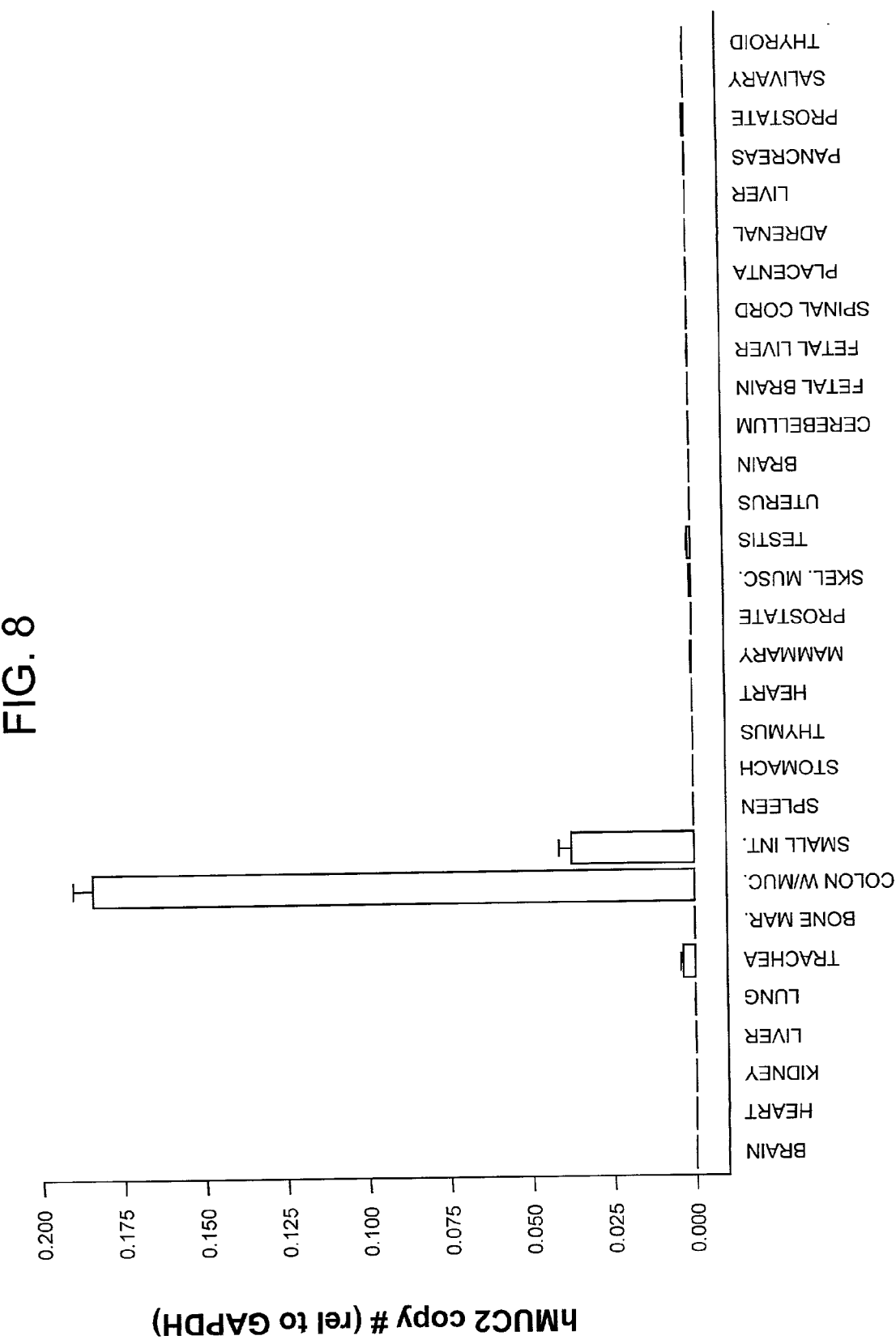
FIG. 8 provides an expression profile for hMUC2 in normal human tissues.

We also developed qRT-PCR expression assays for the known human mucins speculated to be involved in hypersecretory diseases. We evaluated hMUC1 (FIG. 7) as a control mucin (non-gel-forming and nonsecreted), which is not thought to be involved in producing mucus. In contrast, hMUC2, hMUC4, hMUC5AC, hMUC5B, and hMUC6 are all thought to be large gel-forming secreted mucins with a putative role in mucus production in various mucosal tissues. Therefore, we evaluated expression of these six mucins in the same panel of normal tissues used above for hCLCA1 (see FIGS. 8, 9, 10, 11, 12).

Figure 9:
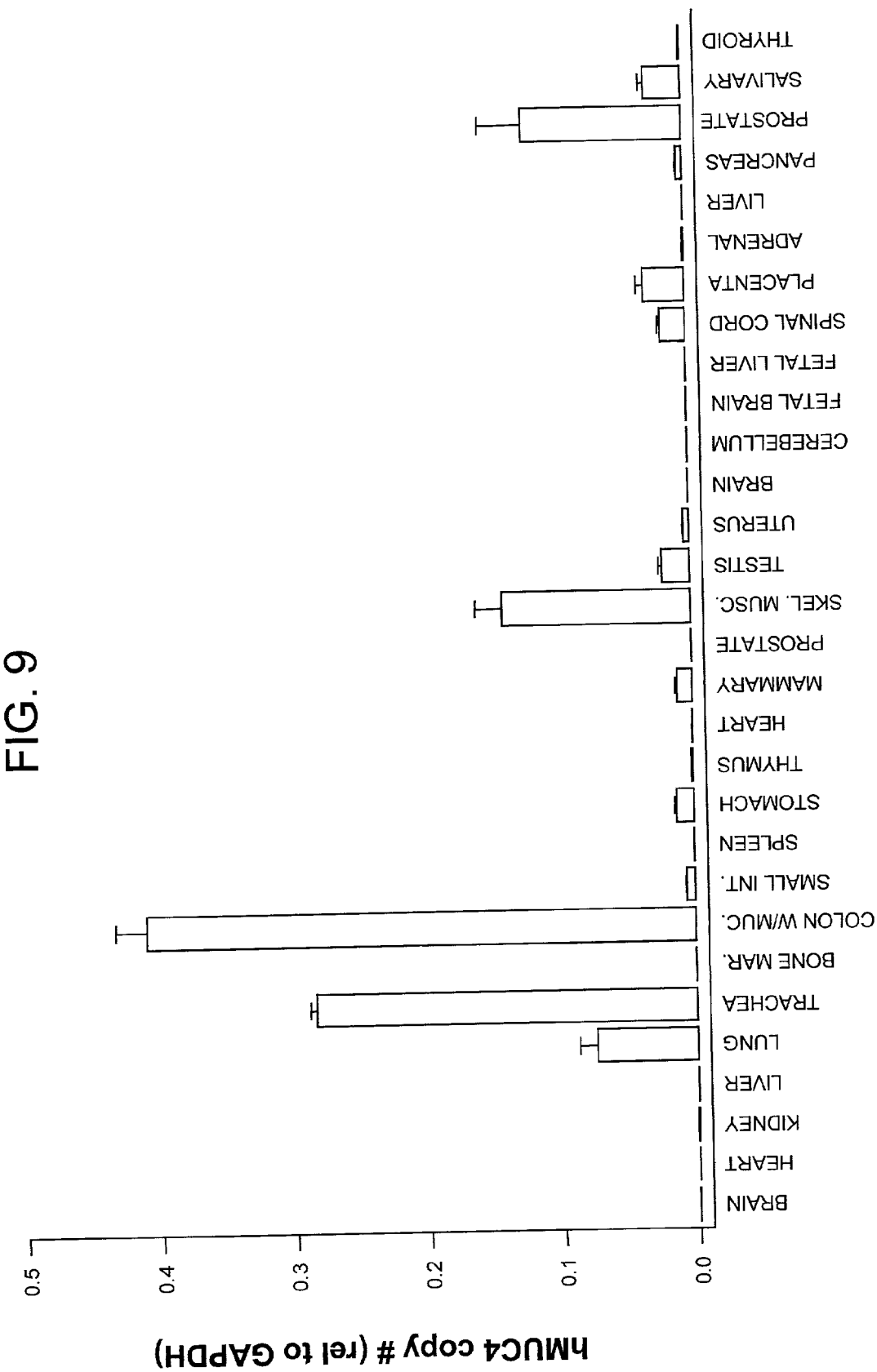
FIG. 9 provides an expression profile for hMUC4 in normal human tissues.
Figure 10:
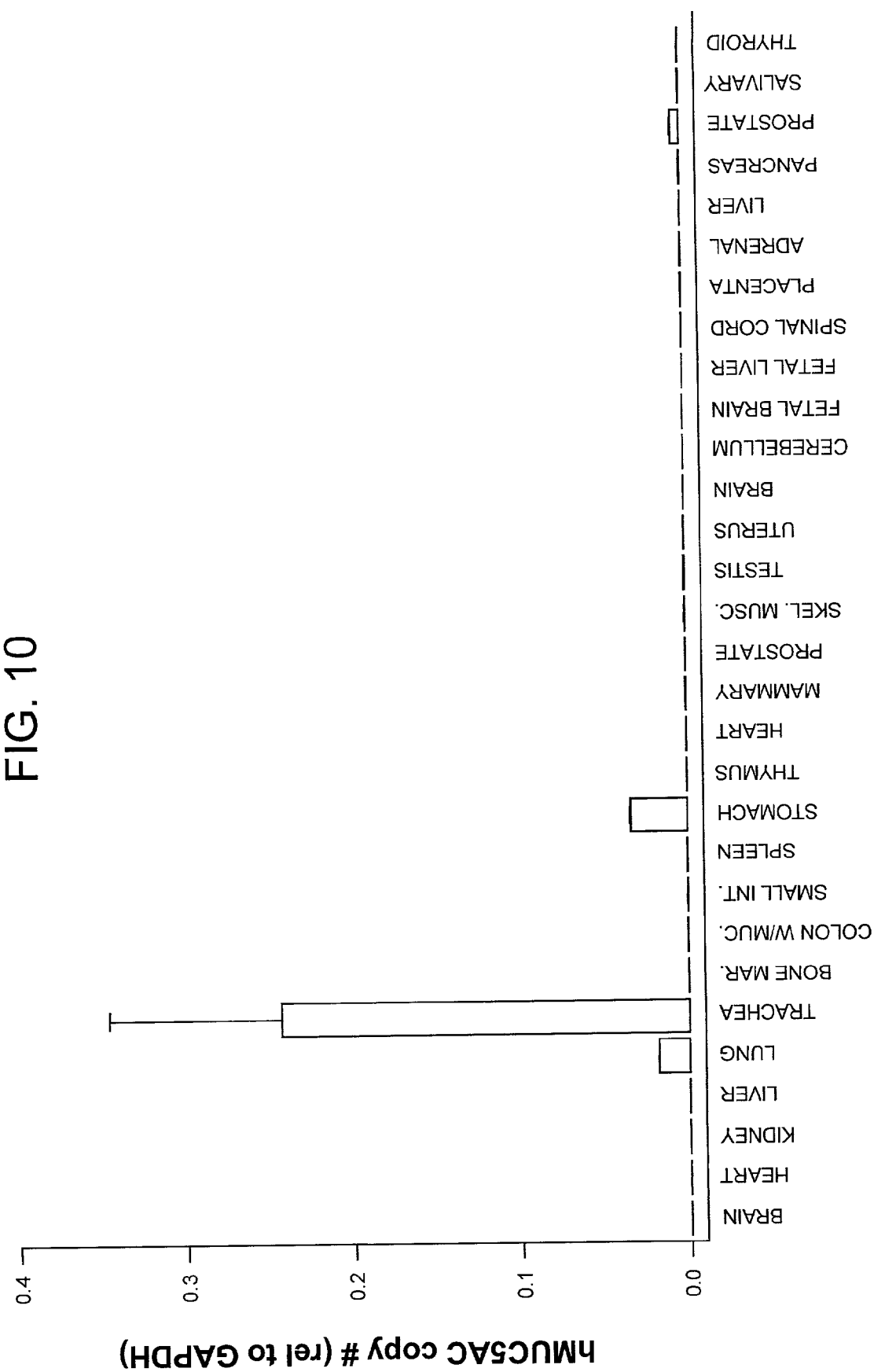
FIG. 10 provides an expression profile for hMUC5AC in normal human tissues.
Figure 11:
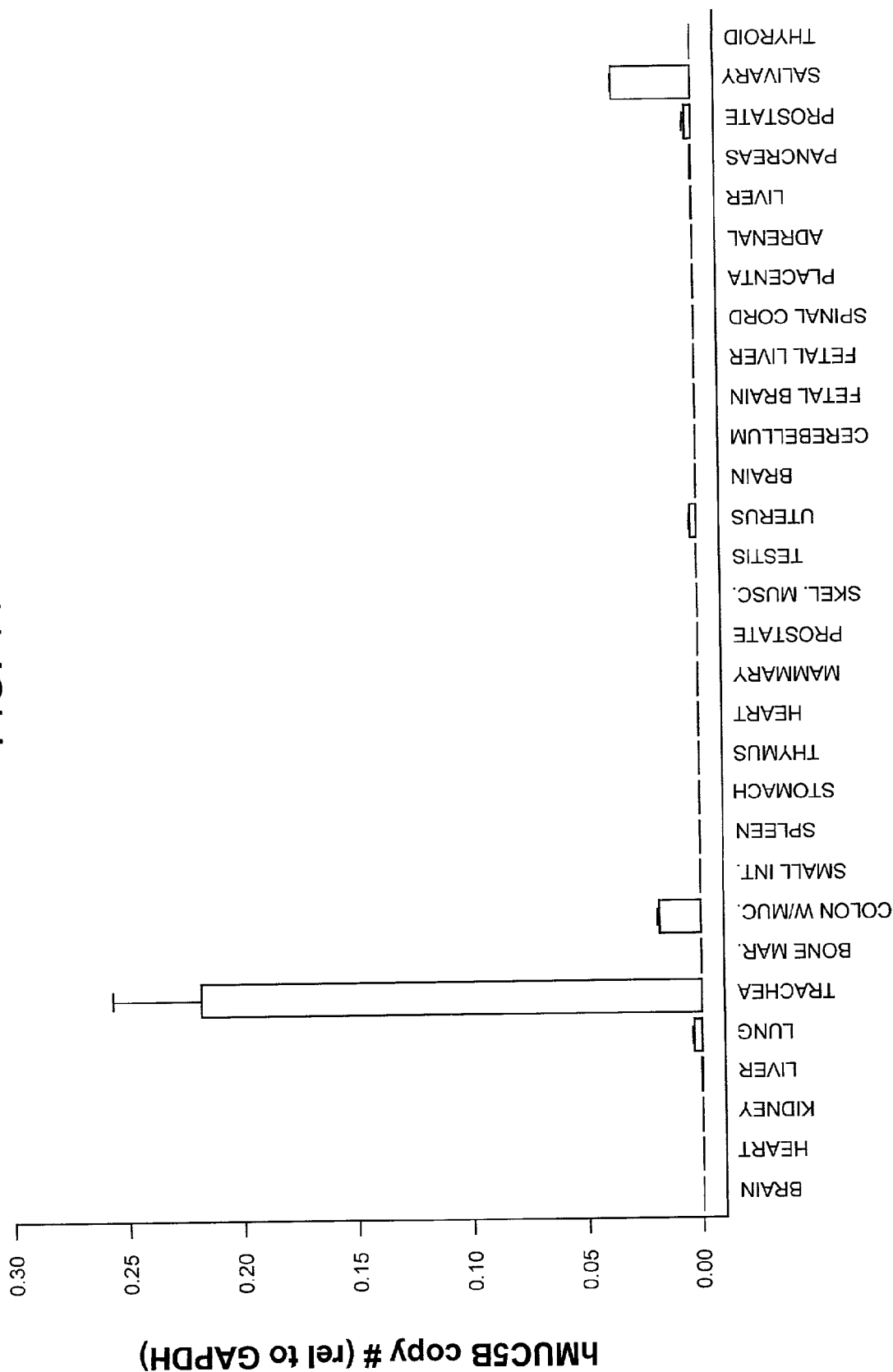
FIG. 11 provides an expression profile for hMUC5B in normal human tissues.
Figure 12:
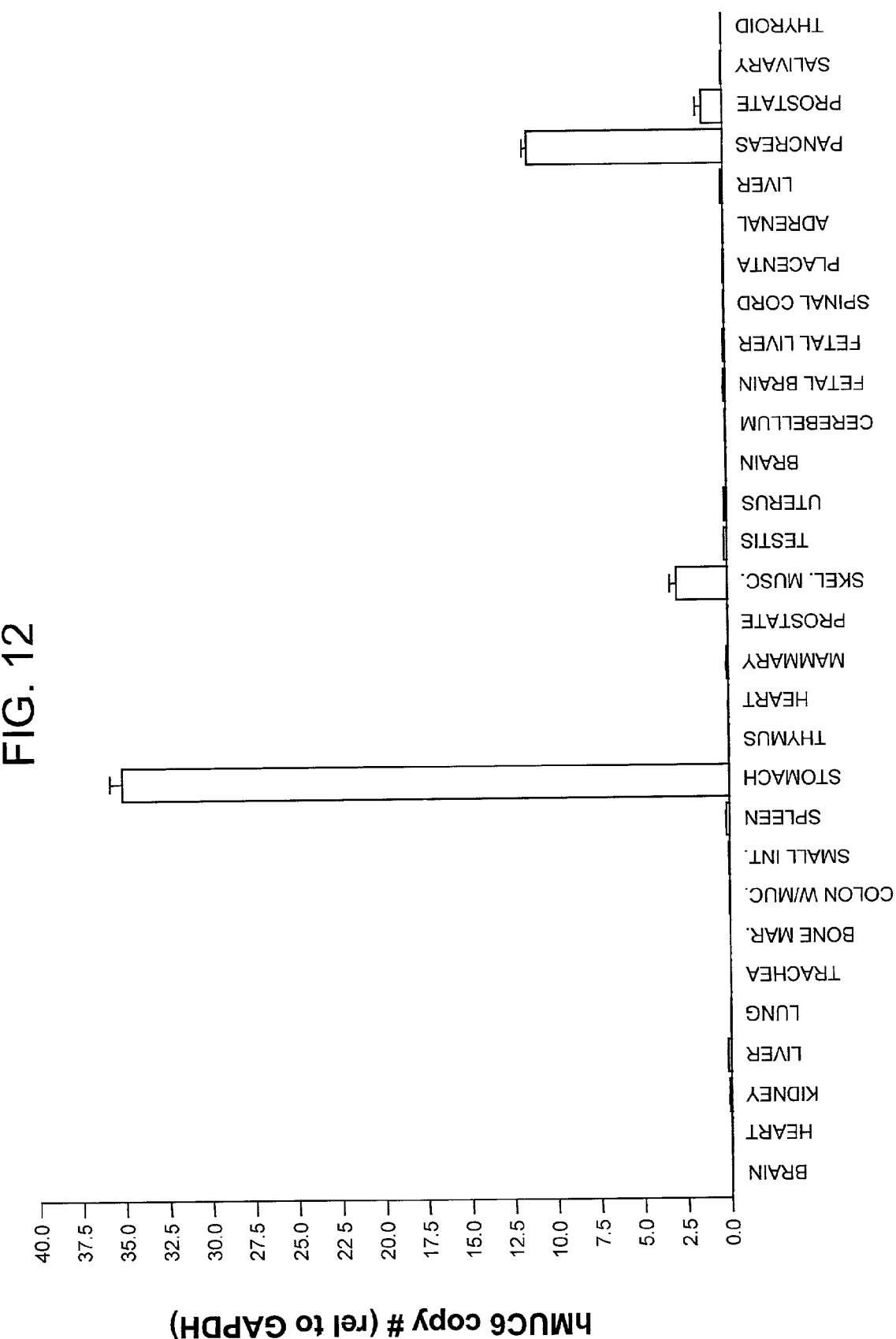
FIG. 12 provides an expression profile for hMUC6 in normal human tissues.

Our quantitative results indicate that there is a dramatic tissue specificity for mucin and CLCA expression. hMUC5AC and hMUC5B, in particular, are both localized to tracheal tissue, and to a lesser extent, salivary glands (hMUC5B) and stomach (hMUC5AC) (FIGS. 10 and 11). In contrast, hMUC6 is primarily a stomach mucin (FIG. 12), and hMUC2 is an intestinal (both large and small) mucin (FIG. 8). hMUC4 is also expressed in the lung and trachea, as well as in colon, skeletal muscle and prostate (FIG. 9). Our results indicate that hMUC5AC and hMUC5B are the mucins most closely associated with mucus secretion in the airways (and in particular, the trachea) of healthy humans.

Figure 5:
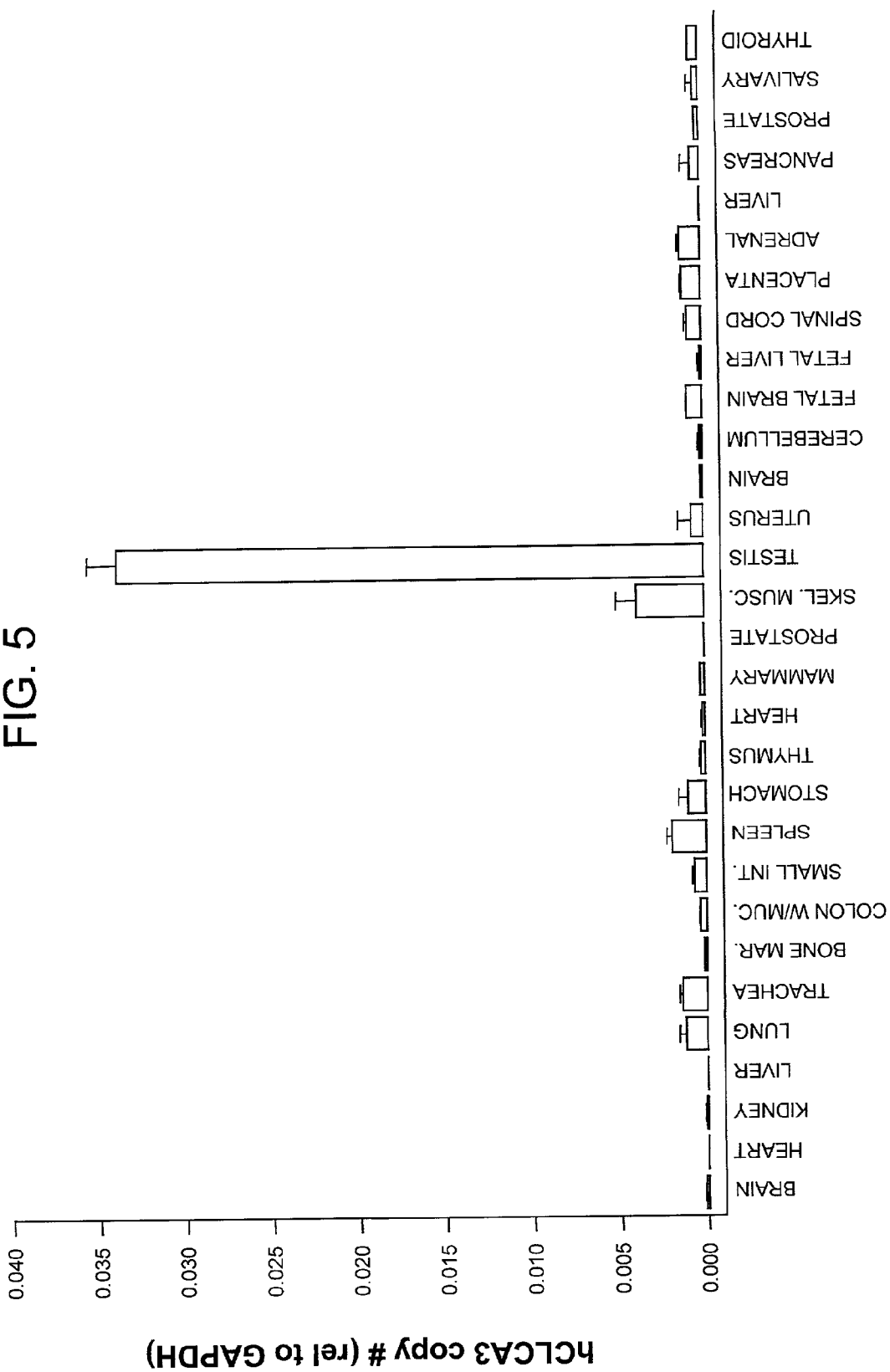
FIG. 5 provides an expression profile for hCLCA3 in normal human tissues.
Figure 6:
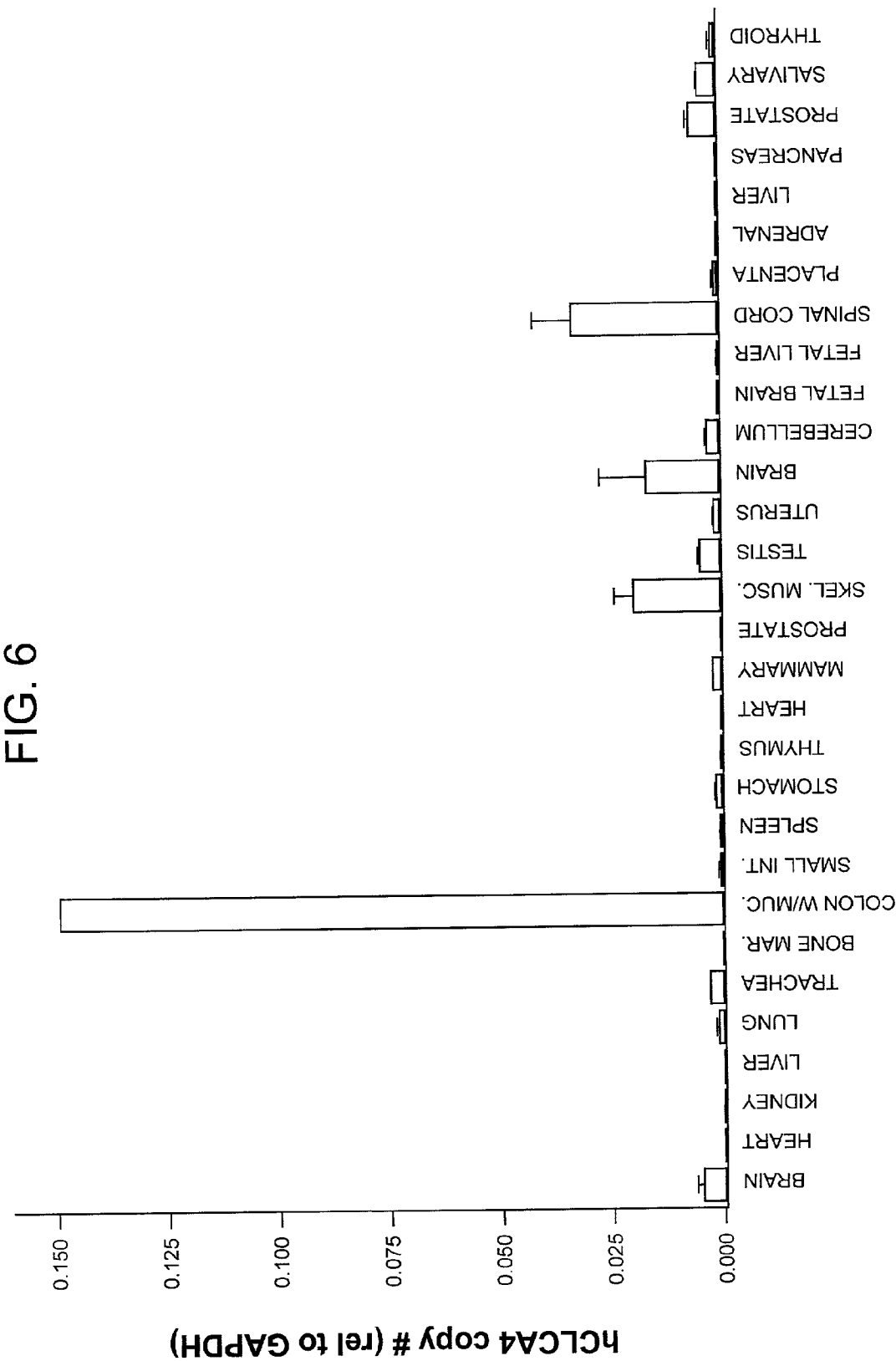
FIG. 6 provides an expression profile for hCLCA4 in normal human tissues.

Our results for CLCA expression in normal human tissues are also compelling. hCLCA1, contrary to findings reported in the prior art (see e.g., WO99/44620 and Nakanishi et al., Proc Natl Acad Sci USA 2001 Apr. 24;98(9):5175–80), is localized to the normal intestine, not the normal human airway (FIG. 3). hCLCA1 shows a similar expression pattern to hMUC2 in the intestine (FIG. 8), implying that this chloride channel regulates production of intestinal mucus (composed of hMUC2) in normal humans. In contrast, hCLCA4 is expressed predominantly in the colon (FIG. 6), implying a distinct role for this channel particularly in the large, but not small, intestine. These findings for hCLCA1 and hCLCA4 should be valuable in developing drugs to treat gastrointestinal diseases of mucus over- or under-production, such as inflammatory bowel disease. hCLCA3 is reported to be an unusual truncated and secreted calcium-activated chloride channel protein, and so is highly unlikely to be a functional ion channel. Not surprisingly, hCLCA3 is expressed only at low levels in many tissues, primarily in the testes (FIG. 5). Finally and most importantly, hCLCA2 is expressed in the normal human trachea and lung (FIG. 4), indicating that hCLCA2 has a critical role in airway mucus production—probably by regulating hMUC4, hMUC5AC and hMUC5B (the major mucins expressed in the airway). hCLCA2 is also expressed at high levels in skeletal muscle, mammary glands, testis, uterus, placenta, and prostate, suggesting a function for CLCA2 in these organs as well.

Figure 13:
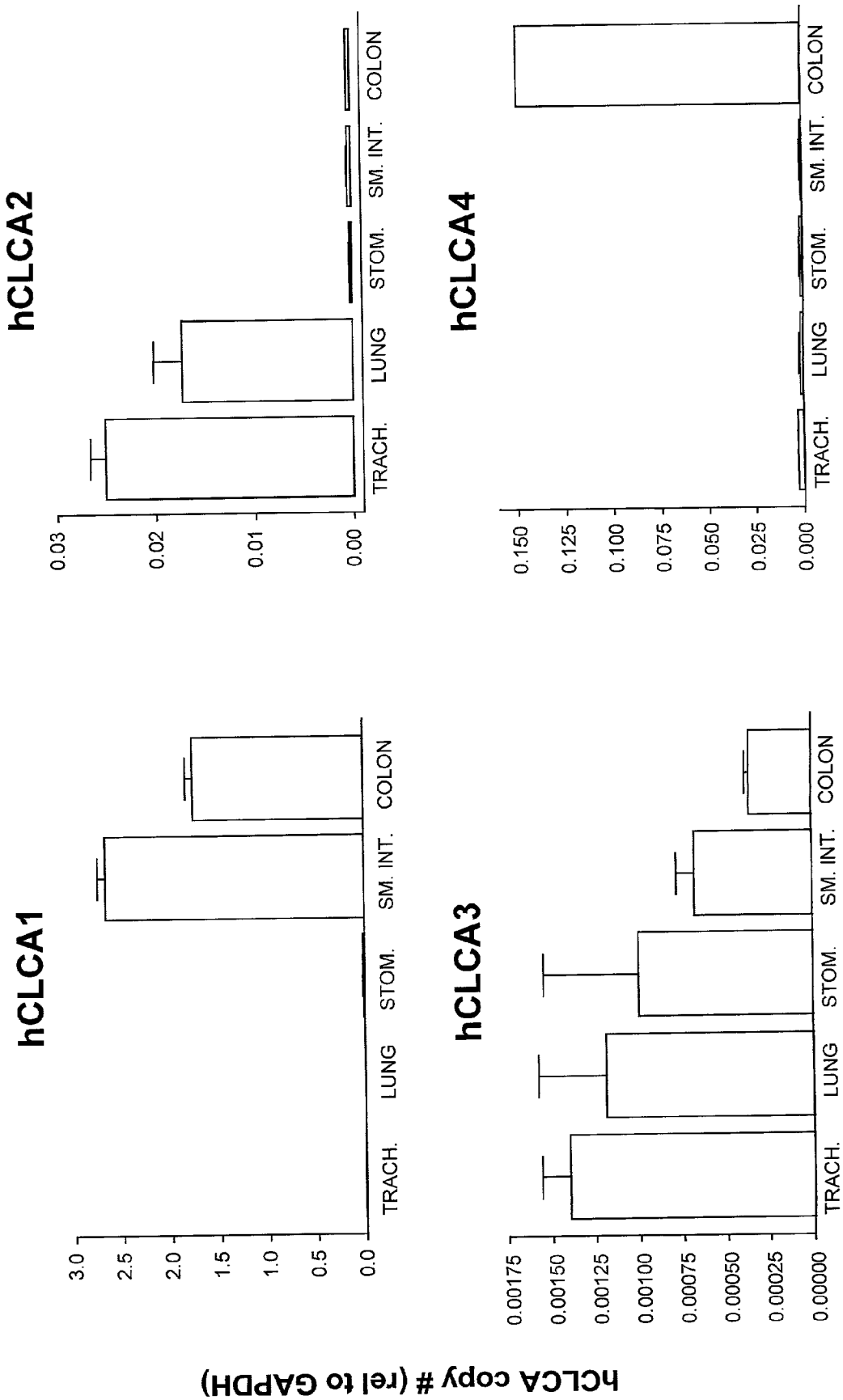
FIG. 13 provides the expression profile for hCLCA1, 2, 3 and 4 expression in selected normal mucosal tissues.
Figure 14:
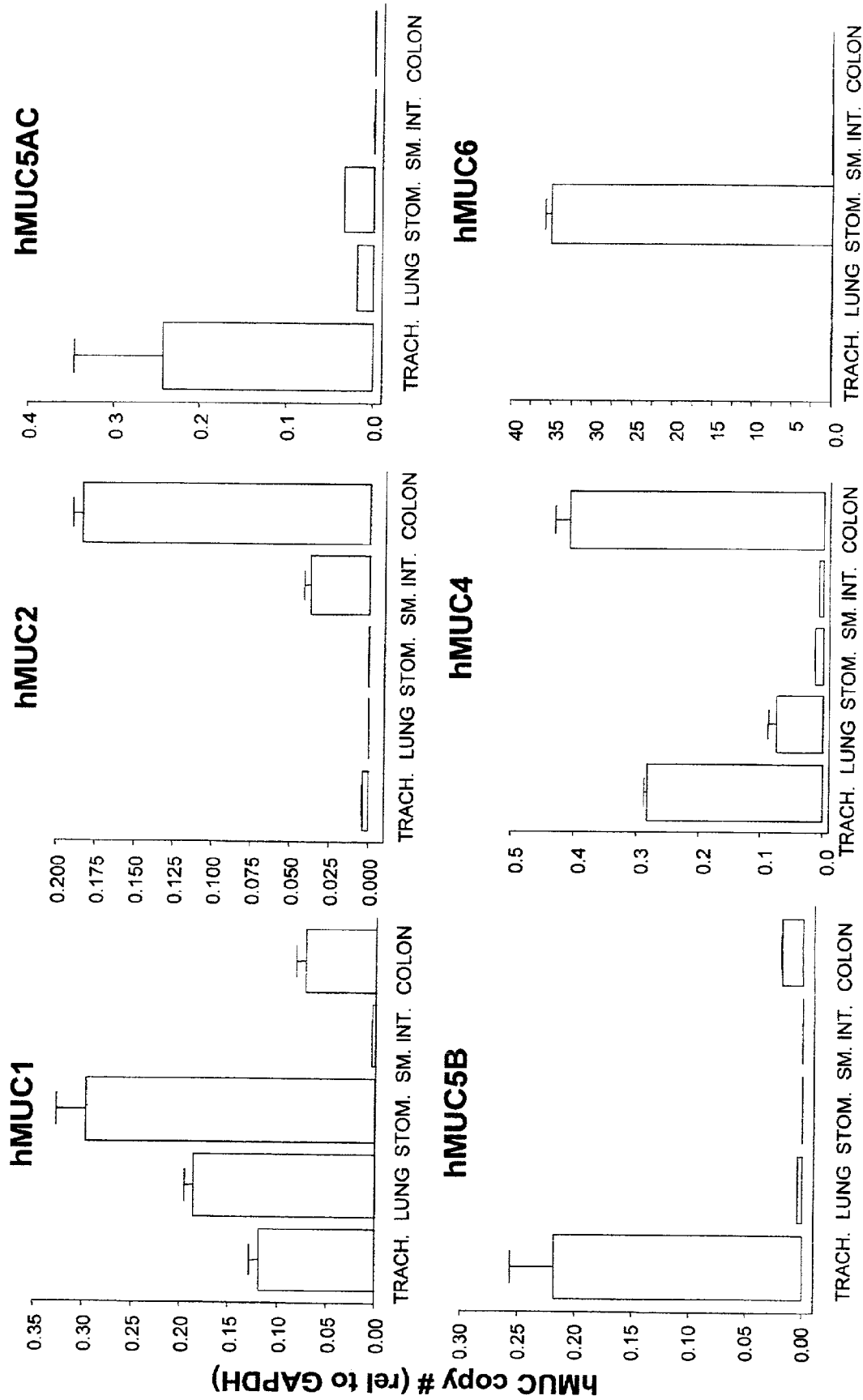
FIG. 14 provides the expression profile for hMUC1, 2, 3, 5AC, 5B, and 6 expression in selected normal mucosal tissues.

To highlight the striking differential expression patterns of human mucins and CLCAs in normal tissue (shown in FIG. 3–12), we extracted the data from mucosal tissues and replotted these in FIG. 13–14. These graphs clearly show that hCLCA1 is a chloride channel expressed primarily in the intestines, hCLCA4 is expressed only in the colon, while hCLCA3 is widely expressed but at very low levels. In contrast, hCLCA2 is expressed in the trachea and lung (FIG. 13). Of the gel-forming mucins, hMUC4, hMUC5AC, and hMUC5B are found in the trachea, with much lower levels in the lung (FIG. 14). The above results indicate that hCLCA2, but not hCLCA1 (contrary to the findings of the prior art cited above), has a role in the production of mucins hMUC4, hMUC5AC, and hMUC5B in the human airway.

EXAMPLE 2

Expression of Mucins in Human Hypersecreting Lung Diseases

Figure 25:
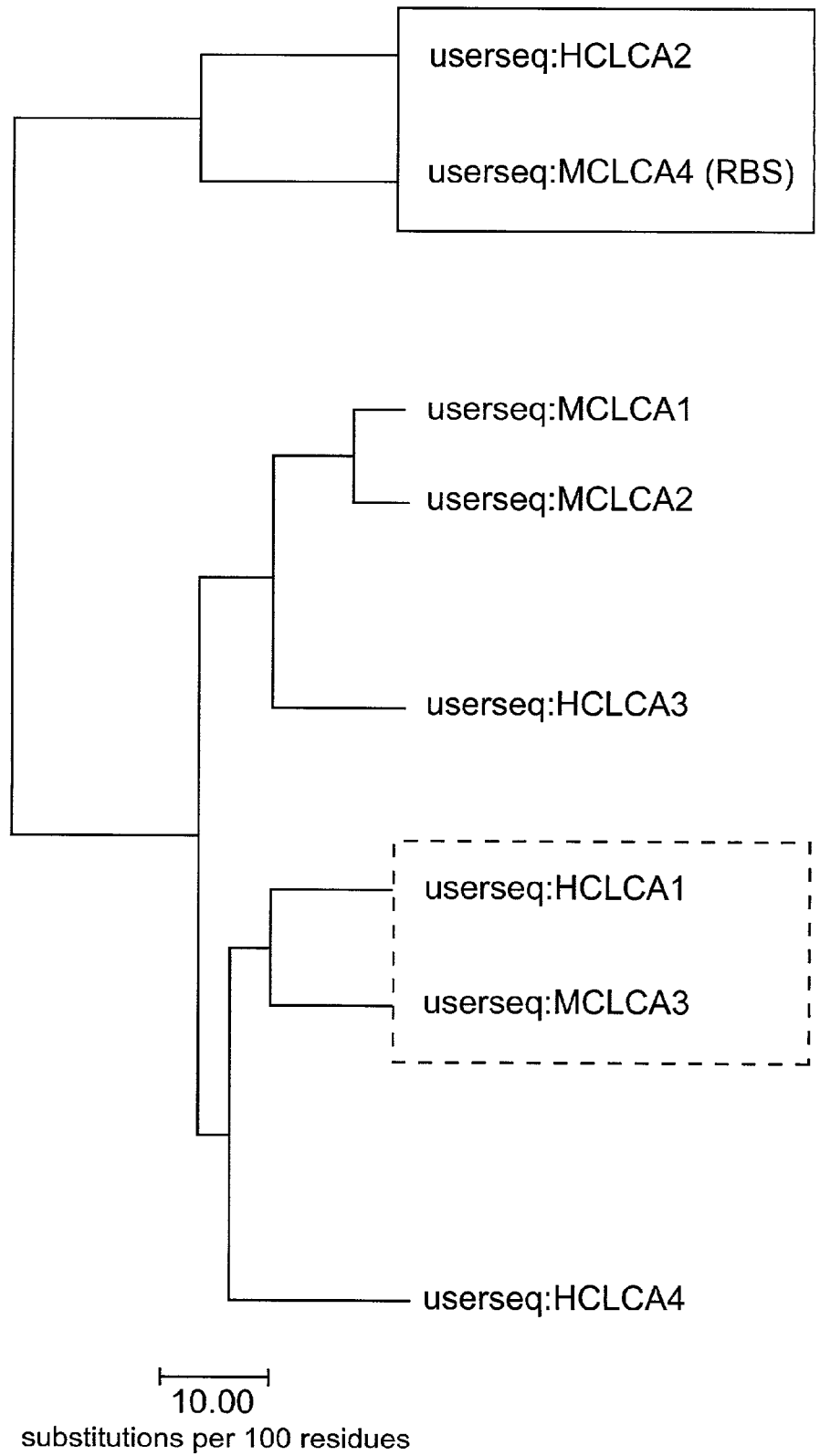
FIG. 25 provides a phylogenetic tree for human and mouse CLCAs.

Although we demonstrated that hCLCA1 is undetectable in the normal human lung (indicating that this gene is not involved in mucus secretion in the lung), the possibility remained that this chloride channel might be strongly induced in association with goblet cell hyperplasia, analogous to the mouse results reported in WO99/44620 and Nakanishi et al., Proc Natl Acad Sci USA 2001 Apr. 24; 98(9):5175–80. hCLCA1 is the closest known homolog to mCLCA3 (also known as mGob-5) (see FIG. 25). The above described initial evidence showed that there is no mCLCA3 detectable in normal mouse airway, yet the gene is strongly induced in hypersecreting mice, correlating with mMUC5AC, mucus secretion, and goblet cell hyperplasia. It is logical that human lung diseases of mucus hypersecretion are analogous to mouse models of hypersecretion; therefore, the first hypothesis was that we would detect high levels of hCLCA1 expression only in hypersecreting, not normal, human lungs.

After showing the strong association between chloride channel hCLCA2 and mucins hMUC5AC and hMUC5B in normal human airways, the next step was therefore to determine if expression of these mucin and CLCA genes was induced in patients with known hypersecretory diseases. We obtained bronchial biopsy samples from Dr. Paola Panina (Roche Milan), which came from well-characterized mucus hypersecreting patients. Information on these patients has already been published, making these biopsies ideal for this analysis. These tissues are further described in: Saetta et al., "Goblet cell hyperplasia and epithelial inflammation in peripheral airways of smokers with both symptoms of chronic bronchitis and chronic airflow limitation," Am J Respir Crit Care Med 2000 March; 161(3 Pt 1):1016–21 P.

Figure 15:
FIG. 15 provides a graphical representation of the induction of hMUC5AC in tissue biopsies from mucin hypersecreting individuals.
Figure 16:
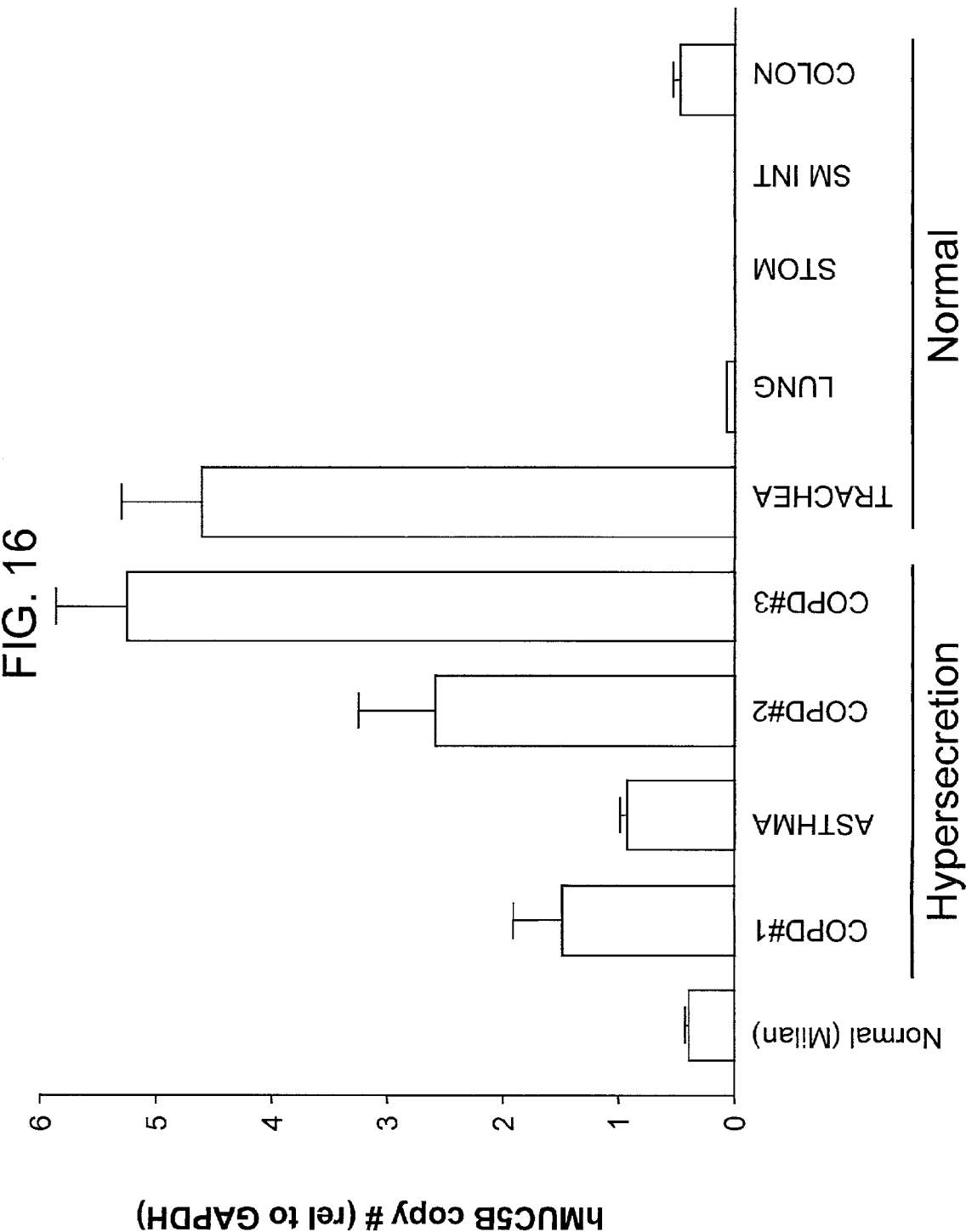
FIG. 16 provides a graphical representation of the induction of hMUC5B in tissue biopsies from mucin hypersecreting individuals.
Figure 17:
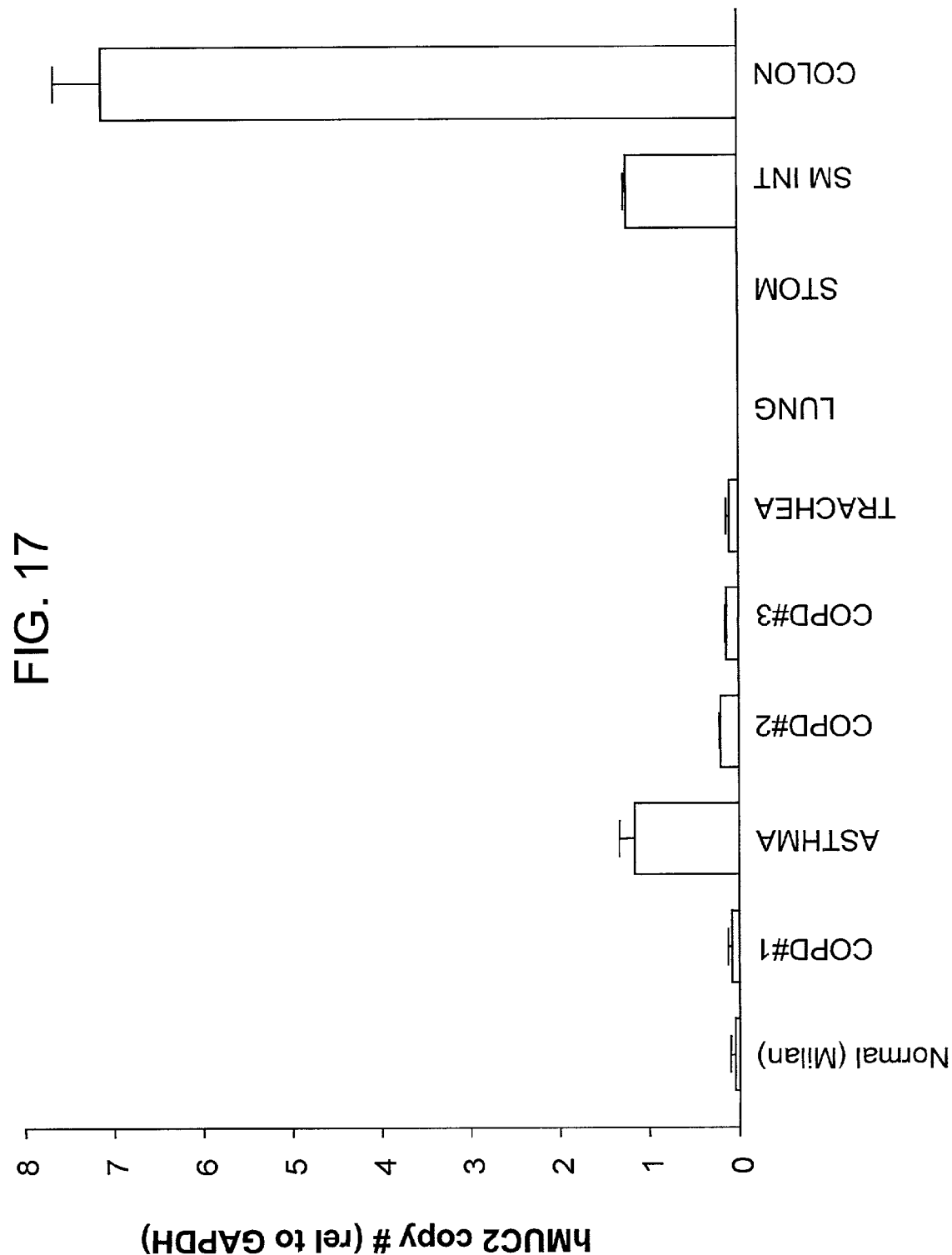
FIG. 17 provides a graphical representation of the induction of hMUC2 in tissue biopsies from mucin hypersecreting individuals.

We evaluated mRNA expression levels of hMUC2, hMUC5AC, and hMUC5B in one normal bronchial biopsy compared to bronchial biopsies from three patients with chronic bronchitis (and COPD) and one with asthma. Our results show that hMUC5AC is strongly induced over normal levels in all four patients (FIG. 15). Of the three gel-forming mucins (hMUC2, 5AC, 5B), hMUC5AC is expressed at the highest levels. hMUC5B is also induced in all four patients, though relative levels are about 10× lower than for hMUC5AC (FIG. 16). Finally, hMUC2 is induced primarily in the asthmatic patient, with relative levels approximately 10–50× lower than for hMUC5AC in the same samples (FIG. 17). Taken with the above data from normal individuals, the above results indicate that hMUC5AC and hMUC5B are found in the normal human airways, and are strongly induced in airways of patients with mucus hypersecretion. Although hMUC2 is normally found in the intestines, in one asthmatic patient its expression is also significantly induced in the airways.

Figure 18:
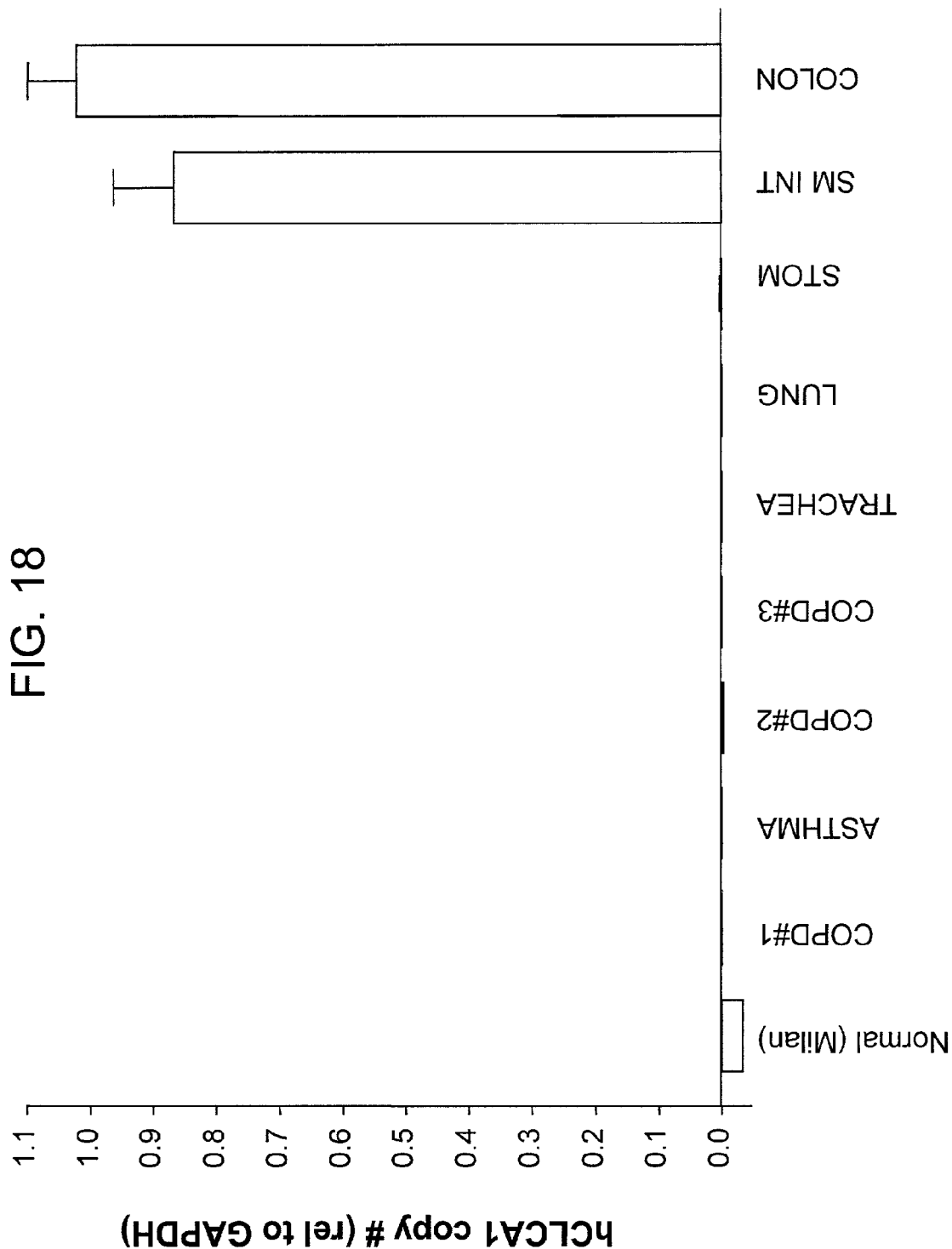
FIG. 18 provides a graphical representation of the induction of hCLCA1 expression in tissue biopsies from mucin hypersecreting individuals.

EXAMPLE 3 hCLCA2 is Induced in Airways of Patients with Mucus Hypersecretion; hCLCA1 Remains Undetectable We next evaluated hCLCA1 vs. hCLCA2 mRNA levels using the same highly selective and quantitative RT-PCR 'Taqman' assays on the Milan human COPD and asthma biopsies. Our results show that hCLCA1 expression is undetectable in bronchial biopsies of either a normal individual, or in patients with mucus hypersecretion (FIG. 18). In contrast with our findings, a poster abstract [Poster: B23] for the American Thoracic Society meeting (San Francisco, May 20–23, 2001), claims that 'ICACC' (presumably ICACC1 or hCLCA1, the gene described in the WO 99/44620 patent application), is induced in COPD. However, no data have been published by any group demonstrating hCLCA1's association with human disease. Our results disagree with these findings, possibly because we use quantitative RT-PCR, while the prior art research that finds hCLCA1 to be the CLCA involved in lung mucin secretion may use in situ hybridization (ISH) to measure gene expression in biopsied human airway epithelium. ISH is a much less selective technique than qRT-PCR, and it is likely that this approach cannot discriminate between expression of hCLCA1 and the other hCLCAs (hCLCA2, hCLCA3, hCLCA4). In contrast, we have shown that our qRT-PCR assays easily discriminate among the four human CLCAs. Therefore, when reviewing patents and published literature, if expression of specific genes in specific tissues is claimed (e.g., hCLCA1 expression in the lung), it is essential to determine if the detection method used cross-reacts with other hCLCAs. We have taken the best approach to this problem, measuring mRNA levels by quantitative RT-PCR (Taqman), the most advanced, sensitive, and selective technique currently possible.

Most importantly, we show that hCLCA2, not hCLCA1, is expressed in the normal lung, and is induced in the lungs of patients with diseases of mucus hypersecretion (see FIG. 19). hCLCA2 is expressed at very low levels in one normal bronchial biopsy (Milan), and several pooled normal trachea and lung samples (Clontech), but is strongly induced in all four patients with hypersecretory disease (Milan samples). These results show that expression of hCLCA2, but not hCLCA1, correlates with mucins hMUC5AC and hMUC5B (but not hMUC2) in the diseased human lung. Therefore, the ion channel activity of hCLCA2 (not hCLCA1, as claimed by others) is involved in goblet cell regulation and mucus production—the primary function of goblet cells in the airway.

Figure 20:
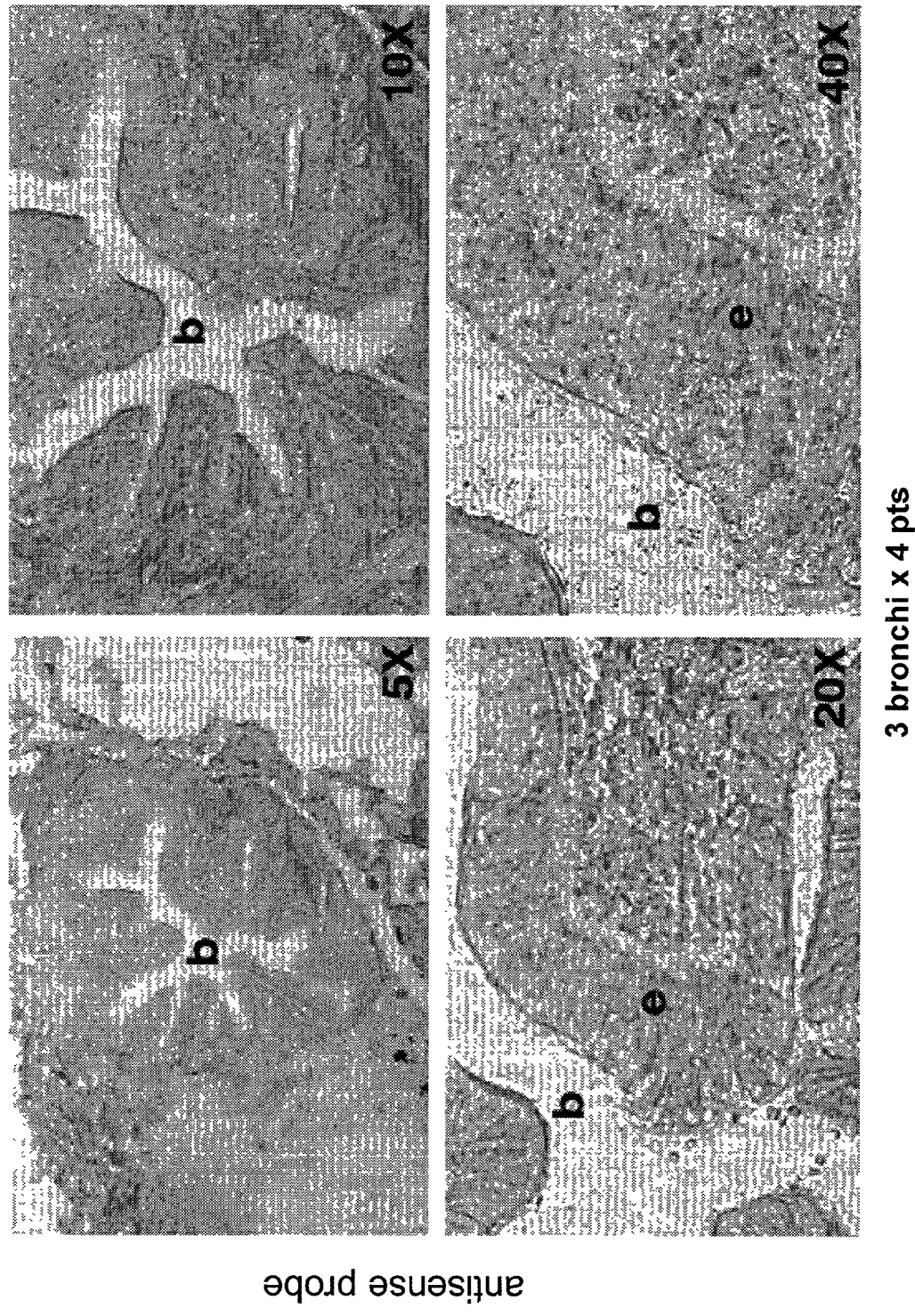
FIG. 20 provides an image of an in situ hybridization (ISH) assay for hCLCA1 expression in mucin hypersecreting lung tissue samples.
Figure 21:
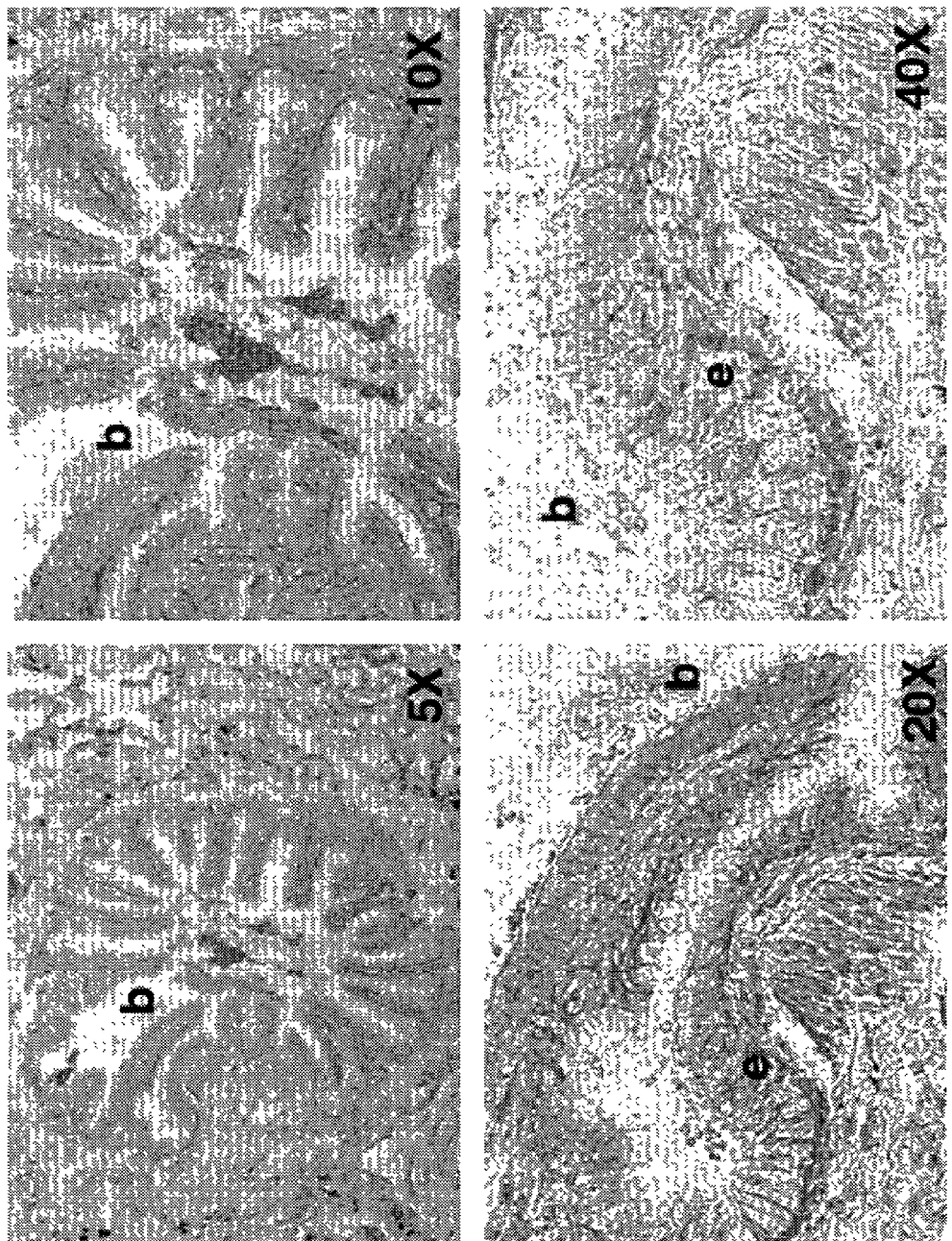
FIG. 21 provides an image of a control ISH for the assay shown in FIG. 20.

To confirm our inability to detect hCLCA1 in the human lung, we evaluated the presence of hCLCA1 mRNA in diseased lung using in situ hybridization (ISH; in collaboration with Dr. Paola Panina, Roche Milan) in addition to using Taqman assays for hCLCA1 vs. hCLCA2. For ISH, Dr. Panina analyzed at least three bronchi per patient in five different patients previously selected as mucus hypersecretors (same Saetta et al. reference given above). Goblet cells are visible in all airways (i.e., they contain mucins) but these goblet cells are negative for CLCA1 staining (FIG. 20). The control 'sense' probe also shows no background staining (FIG. 21). These results indicate that although these human hypersecretors have elevated levels of goblet cells and mucus, as expected, hCLCA1 remains undetectable on goblet cells. These results thus show that hCLCA1 is not involved in mucin production and mucus hypersecretion in human disease.

The above evidence generated by investigating human diseased lung (by both qRT-PCR and ISH) therefore shows that the mouse hypersecretion models are not predictive of hCLCA protein function in human disease. That is, the prior art researchers who have focused on the role of hCLCA1 in human disease have been mislead 1) by reliance on mouse models, and 2) by not using a sufficiently powerful technique to discriminate between expression of different hCLCAs in the human lung. The present data now demonstrate that hCLCA1 does not have the same functional role in human lung as does mCLCA3 in the hypersecreting mouse lung. Our qRT-PCR and ISH results for hCLCA1 and hCLCA2 refute both the claims of the prior art regarding hCLCA1 and its teaching that mCLCA3 is the mouse homolog of the human channel involved in mucin lung secretary disease conditions. In summary, the best CLCA sequence homolog between mouse and man does not appear to be the true CLCA functional homolog in the lung.

EXAMPLE 4

CLCAs and Mucins Expressed in Cell Culture Models of Human Lung Epithelium

Based on the compelling association between hCLCA2, hMUC5AC and hMUC5B in normal human tissues and diseased lung, we evaluated an in vitro assay for expression of chloride channels and mucin production in human lung epithelium. Our primary goal in developing this culture system has been to screen compounds in order to identify potential therapeutics for hypersecretory diseases. We also wanted to evaluate the functional relationship between CLCAs and MUCs in goblet cells in a controlled experimental system which mimics the human lung. Therefore, we isolated RNA from primary normal human tracheobronchial epithelial cells (NHTBEs) grown in a specialized cell culture. In this culture system, lung cells are induced to differentiate into ciliated and goblet cells, thereby reproducing, in vitro, the epithelial structure of a human airway.

Figure 22:
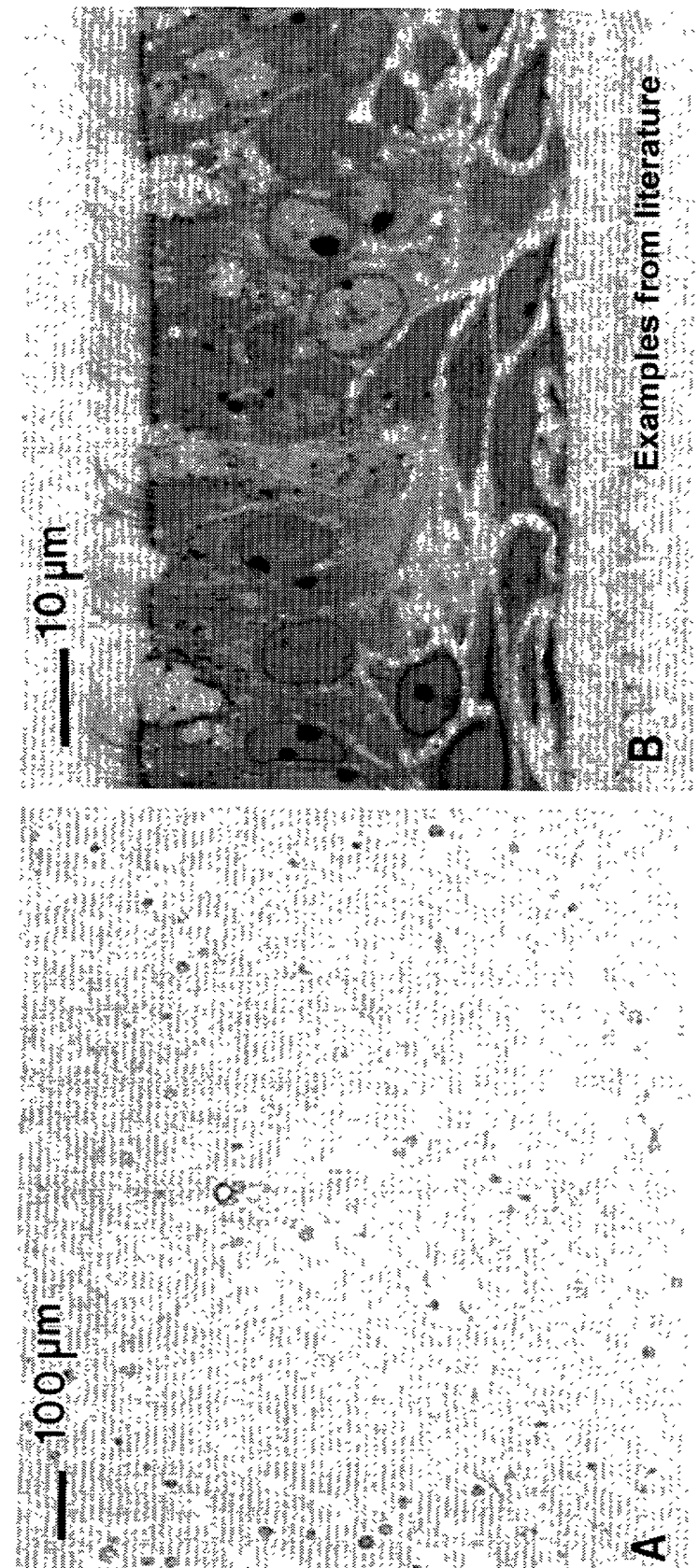
FIG. 22 provides an example of the lung epithelial layers generated in the ALI culture system.

For a description and protocol for the 'air-liquid interface' (ALI) differentiation system for NHTBEs, see e.g., Norford et al., Exp. Lung Res. (1998) 24(3) 355–366). Also see FIG. 22 for an example of the lung epithelial layers generated in this culture system.

Figure 19:
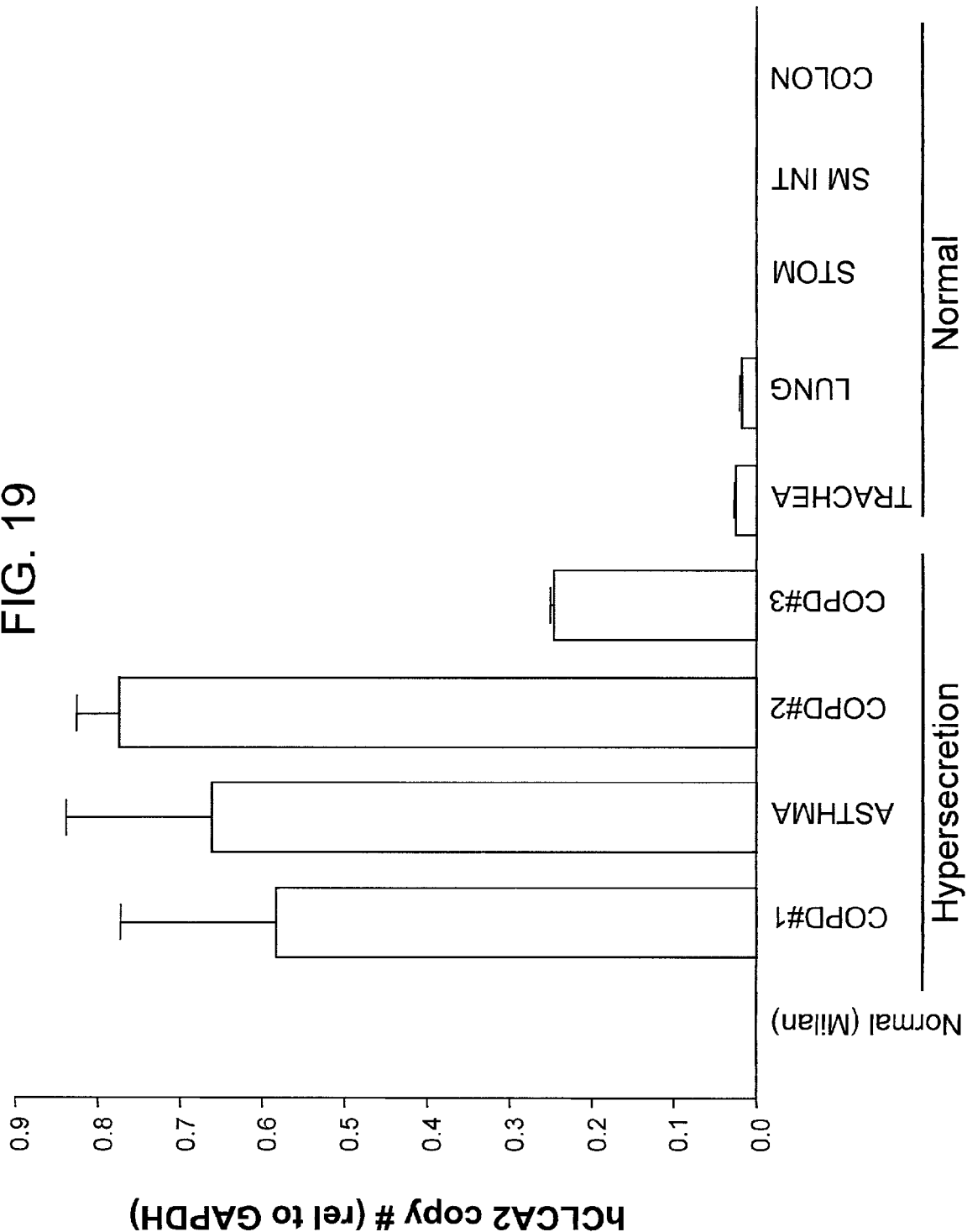
FIG. 19 provides a graphical comparison of the expression level of hCLCA2 in normal and mucin hypersecreting tissues.
Figure 23:
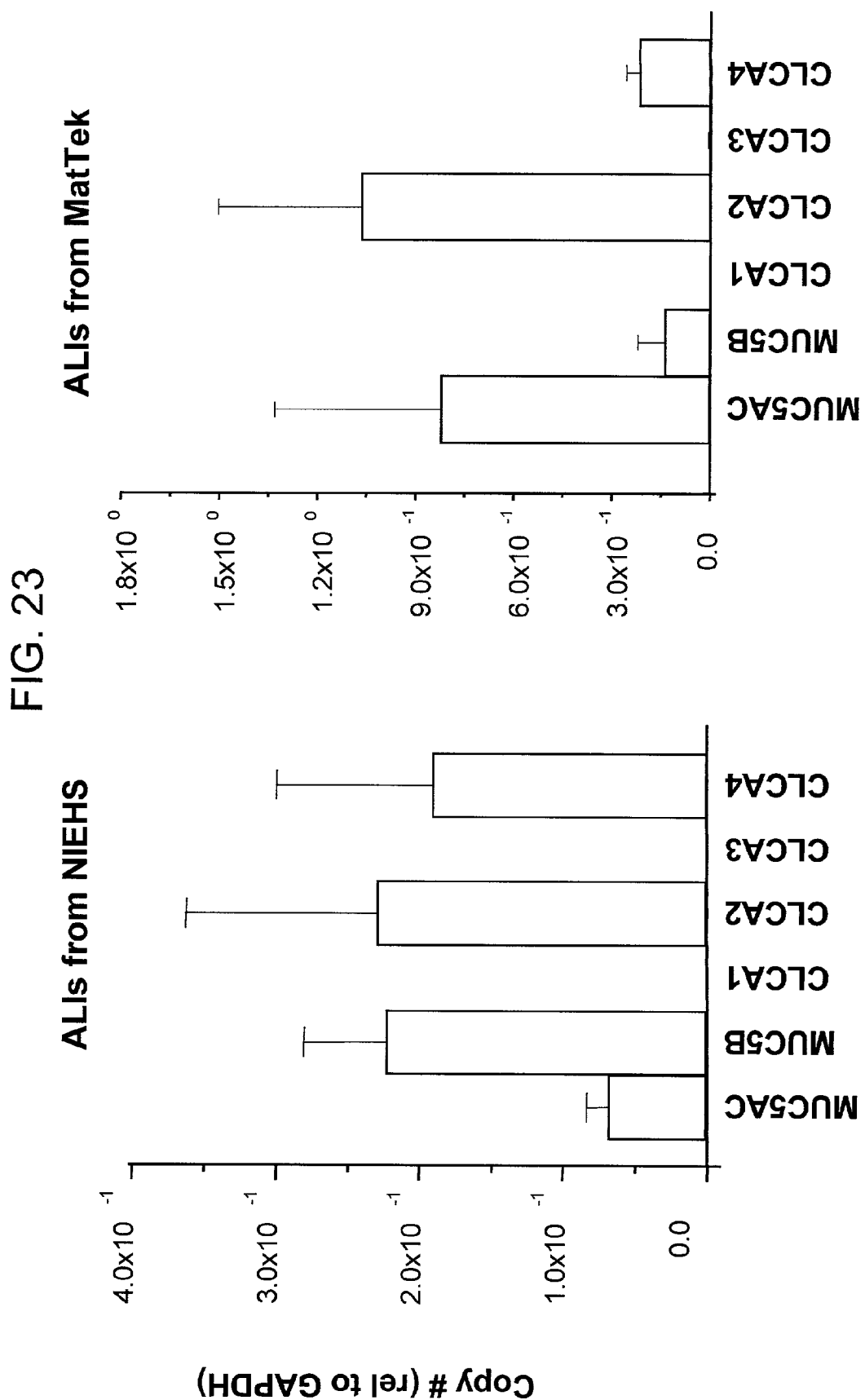
FIG. 23 provides a graphical representation of hCLCA1, 2, 3 and 4 vs. hMUC5AC and hMUC5B gene expression in differentiated human goblet cells in vitro (ALI culture).

We evaluated expression of two key secreted mucins (hMUC5AC and hMUC5B) compared to hCLCA1, hCLCA2, hCLCA3, and hCLCA4 in RNA from human airway ALI cultures obtained from two sources—from Dr. J S Koo at the NIEHS (as referenced above), and from MatTek, a commercial supplier (world wide web address is the www. before "mattek" and the ".com" after "mattek"). Differentiated goblet cells in both systems express hMUC5AC and hMUC5B (see FIG. 23). hCLCA1 and hCLCA3 are not expressed in the in vitro system (FIG. 23), in close agreement with results for these hCLCAs in normal and diseased human lung tissue (FIGS. 3, 5, 18). In contrast, hCLCA2, and to a lesser extent, hCLCA4, is expressed in both ALI culture systems in conjunction with hMUC5AC and hMUC5B. The absence of hCLCA1 expression in this defined human airway goblet cell culture system is further evidence that hCLCA1, contrary to the teaching of the prior art, is not relevant in the human airway. In contrast, hCLCA2 expression in the human in vitro system emphasizes the potential importance of this chloride channel and its association with hMUC5AC and hMUC5B expression both in vitro (FIG. 23) and in human hypersecretory airways disease (FIGS. 15,16, 19). Therefore, we next determined if a commonly used human mucus-producing lung cell line, NCI-H292, would also show a similar hCLCA and hMUC expression pattern.

Figure 24:
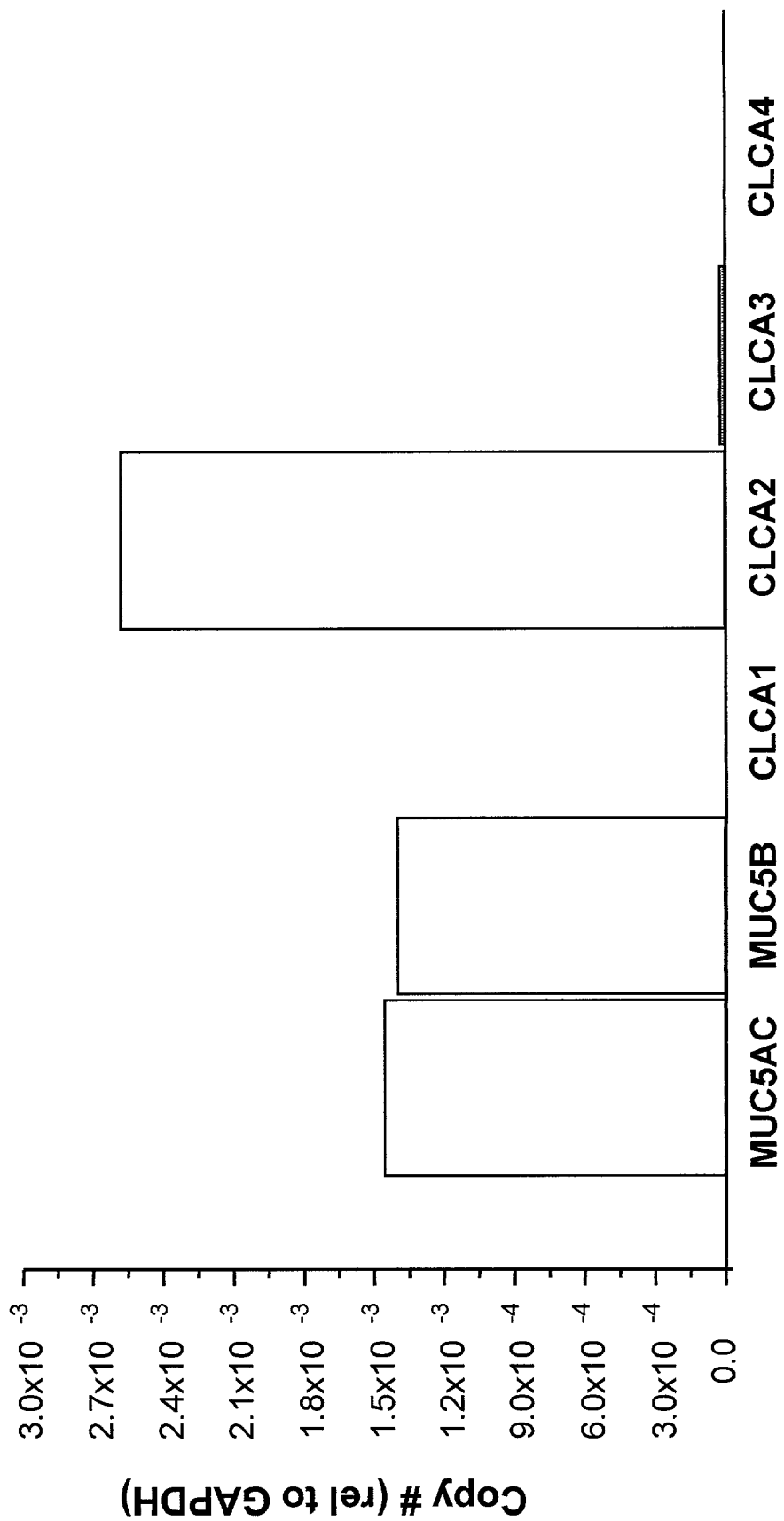
FIG. 24 provides a graphical representation of the expression of hMUC5AC, hMUC5B, & hCLCA1,2,3,4 in mucus-producing human mucoepidermoid lung cell line NCIH292.

For details of the human lung cell line NCI-H292, see Kim et al. Biochem Biophys Res Commun 2001 Jul. 21; 274(1):112–6. Our expression data for NCI-H292 cells demonstrate that these undifferentiated human lung cells, like ALI-cultured differentiated human goblet cells, express hMUC5AC, hMUC5B, and hCLCA2 (FIG. 24). NCI-H292 cells express hCLCA1, hCLCA3, or hCLCA4 at low or undetectable levels, suggesting that hCLCA2 is most tightly associated with mucin expression: 1) in undifferentiated cell lines, 2) in an in vitro goblet cell culture, and 3) in normal and hypersecreting human lungs. The human lung cell line NCI-H292 is therefore also suitable for screening of compounds modulating hCLCA2 function and controlling mucus hypersecretion.

EXAMPLE 5

Mouse vs. Human CLCA & MUC Expression, and Lung Physiology Inconsistencies: Discovery of a New Mouse Homolog (mCLCA4) of the Disease-Relevant Human CLCA2

Typically, mouse and human gene and protein homologs are expected to have similar tissue distributions and functional roles. This is currently the accepted hypothesis for mouse CLCA3 and human CLCA1 (See the above discussed prior art concerning CLCA1). The prior art hypothesis is that hCLCA1 must be relevant in human lung hypersecretory disease because its closest mouse homolog (mCLCA3) is proven relevant in mouse hypersecretory lung models. The above results demonstrate that this hypothesis is wrong. Although mCLCA3 is important in mouse models of lung hypersecretion, the data reported here show that hCLCA1 is not detectable in the human lung, whether in normal individuals or in patients with hypersecretory diseases (COPD or asthma). This finding was the first key result that led to our search for other CLCAs involved in human lung disease, in which we ultimately determined that hCLCA2 is associated with hypersecretion of hMUC5AC, hMUC5B, (as well as hMUC4) in human lung disease. Most importantly, our hCLCA1 results contrast with the teachings of the prior art that suggested (with no data shown) that hCLCA1 is induced in asthmatics and in COPD patients. In other words, the limited prior art and teaching in this area claiming a role for hCLCA1 in lung disease is incorrect.

A CLCA phylogenetic tree that was constructed from known mouse and human CLCA amino acid sequences (FIG. 25) shows that human CLCA2 is clearly distinct from other known CLCAs—an outlier in the group of related known (published or patented) ion channel genes.

Based on our interest in human CLCA2 as the calcium-activated chloride channel associated with lung disease, we searched the Incyte EST database to identify mouse homologs of human CLCA2. The mouse EST was identified and obtained as a public IMAGE clone, which we first identified in the Incyte ZooSeq mouse EST database. The public description for this 'EST sequence (GenBank accession no. AA726662) is 'Similar to SW:ECLC BOVIN P54281 EPITHELIAL CHLORIDE CHANNEL PROTEIN'.

We requested this public clone through Incyte and sequenced the full insert. The 2549 nt sequenced (see FIG. 1A) represents a novel gene not found in public databases. My alignments of the novel mCLCA4 to other human and mouse CLCAs (FIG. 1B for nucleotide, FIG. 1D for protein, FIG. 25 for phylogenetic tree) indicate that this gene is the closest mouse homolog to human CLCA2, and therefore probably a functional homolog in mouse tissues in which it is expressed (see FIGS. 26 and 27 containing expression data for mouse MUCs and CLCAs, respectively). The closest matches in public nucleotide sequence databases are all human CLCA2 (GenBank accession numbers AF043977, AF127980, AX054697, AB026833). The nucleotide sequence of mCLCA4 is an excellent match for hCLCA2 (77% identity using GCG GAP program, parameters: gap weight 50, length weight 3) (see FIG. 1B). Comparison with hCLCA2 nucleotide sequence suggests that our mCLCA4 sequence is likely not full-length, lacking approximately 1200 to 1500 nt at the 5' end of the open reading frame relative to hCLCA2 (a common problem with clones derived from EST libraries). More interestingly, there is an unusual 134 nt deletion in the mouse gene relative to the human (from nt 2129 to 2262 of hCLCA2 AF043977). This deletion leads to a premature stop codon in the mouse CLCA4, although after the stop codon there is an extended 669 nt ORF (from nt 835 to 1503) encoding, another 223 amino acids with strong similarity to human CLCA2. This extended ORF after the stop codon suggests that this particular mCLCA4 deletion is the result of a cloning artifact; another explanation is that the deletion is a recent mutation in mice that may have some functional effect on chloride channel activity. We will reclone mCLCA4 directly from mouse lung to investigate these two possibilities.

To compare putative protein sequences of mCLCA4 and hCLCA2, we next conceptually translated the mCLCA4 cDNA sequence by eliminating the stop codon to make one long open reading frame of exactly 500 amino acids (see FIG. 1C, below). In a GAP (GCG) alignment (FIG. 1D) of novel mCLCA4 to hCLCA2 proteins (943 aa of AF043977), the two sequences are 75.2% similar, 69.8% identical (gap weight=8, length weight=2). This relationship is only slightly weaker than the level of homology between mCLCA3 and hCLCA1 (80.6% similar, 76.2% identical), two proteins accepted in the literature as likely sequence and functional homologs between mouse and man. The mCLCA4-hCLCA2 identity is distributed evenly across the entire sequence, suggesting that mCLCA4 is highly likely to be the functional equivalent in mouse of the human calcium-activated chloride channel hCLCA2. Note that the unusual nucleotide deletion in the mouse sequence results in a 45 amino acid deletion relative to the human sequence. A next step is to determine if this is a true deletion, or resulted from an artifact in the one mCLCA4 clone sequenced.

Figure 27:
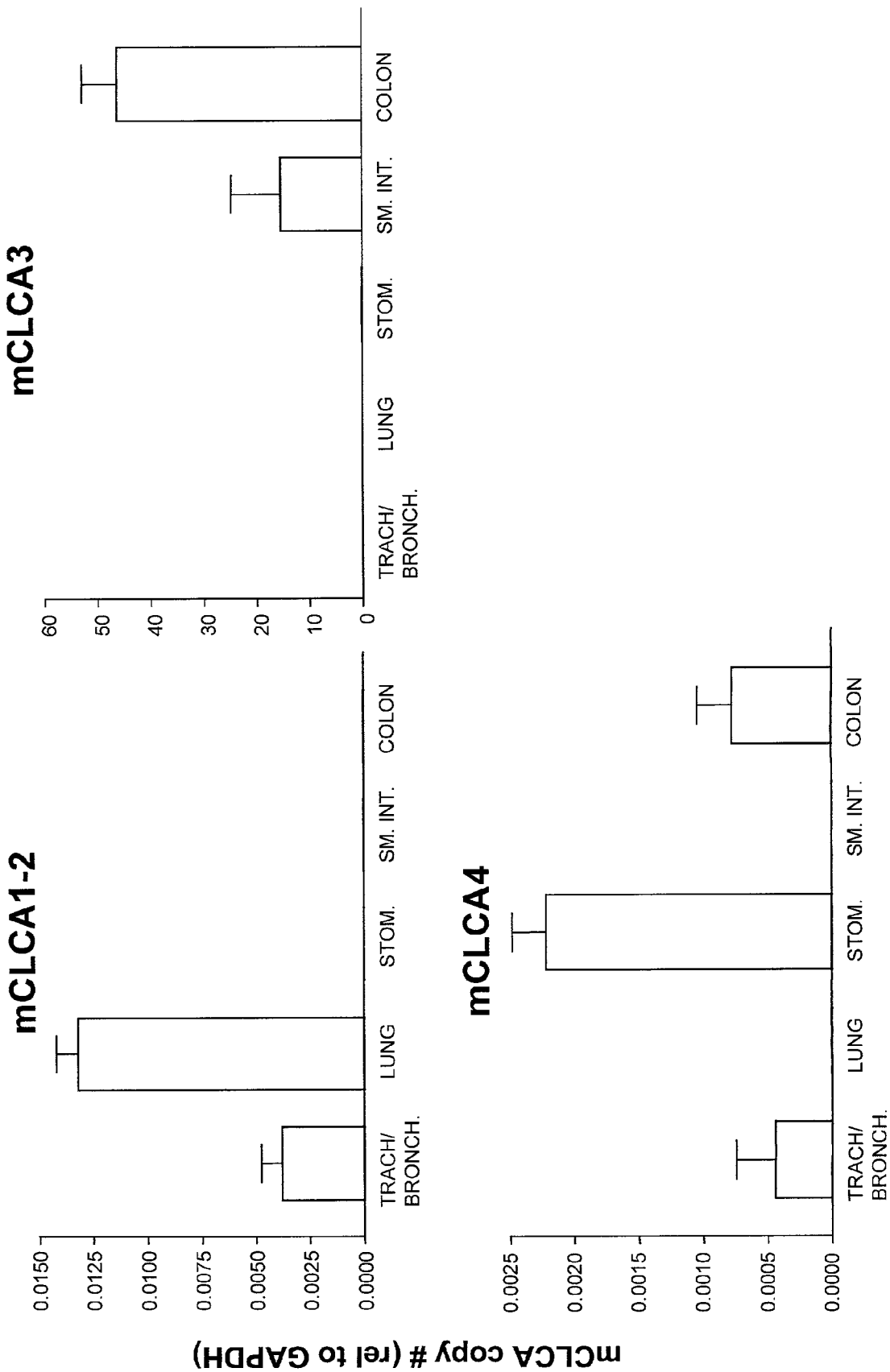
FIG. 27 provides a graphical representation of mCLCA 1–2, 3, and 4 gene expression in normal mouse mucosal tissues.

In order to investigate expression of this putative new chloride channel in various mouse tissues, we also developed a qRT-PCR Taqman assay for mCLCA4. We compared expression of mCLCA4 (best homolog of human CLCA2) to the previously known mCLCA3 (best homolog of human CLCA1) and mCLCA1/2 (best homologs of human CLCA3) (see FIG. 25 for evolutionary tree). Note that mCLCA1 and mCLCA2 are almost identical sequences reported by different academic labs, with 95% identity over 903 amino acids (GenBank accession numbers: mCLCA1, AF047838; mCLCA2, AF108501). In my opinion, mCLCA1 and mCLC2 represent the same gene with just a few sequence differences separating between the two. Because of this, our qRT-PCR assays may not reliably discriminate between the putative mCLCA1and mCLCA2 transcripts (see Table I for Taqman assay details). We also compared mCLCA1/2, mCLCA3, and mCLCA4 expression to mouse mucins mMUC1, mMUC2, and mMUC5AC (the mouse homolog of the important human MUC5B sequence has not yet been reported in the literature). Tissue RNA was prepared at Roche from mouse strain Balb/c. In the healthy mouse, as in the human, mMUC2 is an intestinal mucin (FIG. 26), not expressed in the lung or main airways (trachea and bronchi). Unlike in humans, mouse MUC5AC is primarily a stomach mucin, and was first cloned from the stomach. However, we and others have shown that mMUC5AC expression in the mouse lung increases dramatically in hypersecretion models (data not shown). This different tissue distribution of hMUC5AC and mMUC5AC is further evidence of the different lung physiologies of mice and humans. Humans normally have goblet cells in the trachea while mice do not, unless induced by an external stimulus to hypersecrete mucus. Mouse calcium-activated chloride channels also show a marked tissue specificity. mCLCA1–2 is expressed in the normal mouse airways and lungs (FIG. 27). mCLCA3 is expressed in the normal intestine but is not expressed in the normal mouse lung, in striking agreement with the mMUC5AC result. Finally, the novel chloride channel mCLCA4 is expressed in the tracheal-bronchial tissue, stomach, and colon, but at relatively low levels (FIG. 27). This confirms that the novel mCLCA4 that we identified is expressed in mouse mucosal tissues, and in particular that its mRNA is present in the normal mouse airway. This suggests that we can use mouse hypersecretion models to evaluate modulators of hCLCA2/mCLCA4 as potential drugs for human lung diseases, as well as to evaluate modulators of hCLCA1/mCLCA3 as potential drugs for human gastrointestinal diseases.

It is evident from the above results and discussion that the subject invention provides an effective manner for treating diseases associated with mucin secretion, particularly in the respiratory system. Specifically, the subject invention provides for important and effective new ways to treat disease conditions associated with mucin hyper- or hyposecretion in the respiratory system. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of diagnosing the presence of a mucin hypersecretion respiratory system associated disease condition in a host, said method comprising:
   determining Calcium-activated Chloride Channel 2 (CLCA2) mRNA expression levels in a lung or tracheal sample of said host; and
   relating said determined expression levels to the presence or absence of said disease condition, wherein an increase in said determined expression levels indicates a diagnosis of the presence of a mucin hypersecretion respiratory system associated disease, selected from the group consisting of chronic bronchitis, asthma, and chronic obstructive pulmonary disease (COPD).

2. The method according to claim 1, wherein said host is a human.

* * * * *

SEQUENCE LISTING

<160> NUMBER OF SEQ ID NOS: 4

<210> SEQ ID NO 1
<211> LENGTH: 2499
<212> TYPE: DNA
<213> ORGANISM: mouse

<400> SEQUENCE: 1

| | | | | | |
|---|---|---|---|---|---|
| gcacgagctt | tgaggtggtt | gaggagcgga | atggaagagc | tgacggctct | gtcctgatat | 60 |
| tagtgaccag | tggagcagat | gaacacattg | ccaactgcct | gctcacctcg | atgaacagtg | 120 |
| gatccaccat | tcactccatg | gccctgggtt | cctctgcagc | cagaaaagtg | ggggaattat | 180 |
| cacgtcttac | aggaggtcta | aagttcttca | ttccagataa | atttacttct | aatgaatga | 240 |
| ctgaagcttt | cgttcgaatc | tcttctggaa | caggagacat | tttccagcaa | agcttacagg | 300 |
| ttgagagcgt | gtgcgaaact | gtgcaacccc | agcaccagct | ggcggatact | atgactgtgg | 360 |
| atagcgccgt | gggcaatgac | acactttttc | tagtcacgtg | gcagactggt | ggcccccctg | 420 |
| agattgcatt | attggatcct | agcggaagaa | aatacaacac | tggtgacttt | atcatcaacc | 480 |
| tggcctttcg | gacagccagc | cttaagattc | agggacagc | taagcatggg | cactggactt | 540 |
| acacgctgaa | caacacccac | cattctcccc | aagctctgaa | agtgacagtg | gcctctcgtg | 600 |
| cctccagcct | ggccatgtcc | ccagccactc | tggaagcctt | tgtggaaaga | gacagcacct | 660 |
| attttcctca | gccagtgatc | atttatgcga | atgtgaggaa | aggtctgcat | cccattctca | 720 |
| atgccaccgt | ggtggcgaca | gtggaaccag | aggctggaga | tcccgttgta | ctgcaacttt | 780 |
| tggatggcgg | agcaggtgca | gatgttataa | gaaatgatgg | gatttactcc | agataatatt | 840 |
| caaatgaatg | ctcccaaaaa | cttgggccac | agacctgtga | aggagaggtg | gggcttcagt | 900 |
| cgagtgagct | cggagggctc | cttctccgtg | ctgggagtcc | cagacggccc | ccaccctgac | 960 |
| atgtttccac | cgtgcaaaat | tactgacctg | aagccatga | aagtggaaga | cgacgtcgtc | 1020 |
| ctctcttgga | cggcacctgg | ggaagacttc | gatcagggc | aaactacaag | ctatgaaata | 1080 |
| agaatgagca | gaagcctatg | gaacattcgg | gatgactttg | acaatgccat | cttggtgaat | 1140 |
| tcgtcagagc | tagttcctca | gcatgctggc | accaggagga | catttacatt | ctcacccaag | 1200 |
| cttgtcaccc | atgaacttga | tcatgaactt | gctgaagatg | cacaagaacc | ctacatagtg | 1260 |
| tatgtggccc | tgagagccat | ggatagaagc | tccctcaggt | cagctgtgtc | aaacattgcc | 1320 |
| ctggtatcaa | tgtctcttcc | tccaaactct | tctcctgtag | tgagcagaga | tgatctgatc | 1380 |
| ctgaaaggag | ttttaacaac | agtaggtttg | atagcaatcc | tttgccttat | tatggttgta | 1440 |
| gcacactgta | ttttaacag | gaaaagaga | ccatcaagaa | aagagaatga | gacaaaattt | 1500 |
| ctatgaacaa | gcaggcacag | tatcttcctt | cttaggtagg | atggacatga | cctttacatc | 1560 |
| cacaaaataa | aatgtgaaca | aaatcaaaat | agtctcgaca | tggggacttt | tacataatgc | 1620 |
| aaaaatgccc | tcccccccc | ccaaaaaaaa | cccaccaact | tttaactcat | tttgggaaag | 1680 |
| ggttagaaaa | cagtgtaagg | ttccagttat | ggaaaaataa | taaatatat | tgctcaaggt | 1740 |
| aatggcttga | aaggcaaagg | aagaacaaaa | tcaaatcgag | tcaagaaaag | cttgttttat | 1800 |
| tgaagttcag | gttgggggaa | gttctgggta | cagaaaagaa | tgttgggtct | tagttagaca | 1860 |
| gtgtaactat | ctgtatgatg | caaacatgtt | actttgatga | atttctcatc | tctgcttatc | 1920 |
| tgtgcagaga | aggacacatg | tttatactga | caaccaagct | gctttataga | agaggccata | 1980 |
| ctacagggtt | cttttatatct | tgtcctttgg | ttaaattcac | tgtggctcac | aagacaccac | 2040 |

-continued

```
taaagttcag ataggacttt tctcaccatg agaggagacc ttagaatgca attgttgtcc    2100
ttgtcccttg gatactgatc tgtagcagag gtcaccggag tttactgttt gtaagacgtt    2160
agtgccattg aagcagcttt ctaagttatt ggcttggaag tattgaatga aaatggttac    2220
ggctcccatg aggctttaca ggtaaaagac attatgctga ataattttta atatatacac    2280
catatagttt tattccatct caaataagaa gtcatggaaa caattagcaa attctgcccc    2340
ggtttaataa gtacatgcaa ttcttttctt catcaaggac acagaaaga cagcagagaa     2400 aatgtggaaa taaaaatcat ctaatgctac ttcttccttt taaaaaatgt tatttaataa    2460
tattatgtca tttctaaatt caagaactta aaggtttat                            2499
```

<210> SEQ ID NO 2
<211> LENGTH: 500
<212> TYPE: PRT
<213> ORGANISM: mouse

<400> SEQUENCE: 2

```
Thr Ser Phe Glu Val Val Glu Glu Arg Asn Gly Arg Ala Asp Gly Ser
  1               5                  10                  15

Val Leu Ile Leu Val Thr Ser Gly Ala Asp Glu His Ile Ala Asn Cys
             20                  25                  30

Leu Leu Thr Ser Met Asn Ser Gly Ser Thr Ile His Ser Met Ala Leu
         35                  40                  45

Gly Ser Ser Ala Ala Arg Lys Val Gly Glu Leu Ser Arg Leu Thr Gly
     50                  55                  60

Gly Leu Lys Phe Phe Ile Pro Asp Lys Phe Thr Ser Asn Gly Met Thr
 65                  70                  75                  80

Glu Ala Phe Val Arg Ile Ser Ser Gly Thr Gly Asp Ile Phe Gln Gln
                 85                  90                  95

Ser Leu Gln Val Glu Ser Val Cys Glu Thr Val Gln Pro Gln His Gln
            100                 105                 110

Leu Ala Asp Thr Met Thr Val Asp Ser Ala Val Gly Asn Asp Thr Leu
        115                 120                 125

Phe Leu Val Thr Trp Gln Thr Gly Gly Pro Glu Ile Ala Leu Leu
    130                 135                 140

Asp Pro Ser Gly Arg Lys Tyr Asn Thr Gly Asp Phe Ile Ile Asn Leu
145                 150                 155                 160

Ala Phe Arg Thr Ala Ser Leu Lys Ile Pro Gly Thr Ala Lys His Gly
                165                 170                 175

His Trp Thr Tyr Thr Leu Asn Asn Thr His His Ser Pro Gln Ala Leu
            180                 185                 190

Lys Val Thr Val Ala Ser Arg Ala Ser Ser Leu Ala Met Ser Pro Ala
        195                 200                 205

Thr Leu Glu Ala Phe Val Glu Arg Asp Ser Thr Tyr Phe Pro Gln Pro
    210                 215                 220

Val Ile Ile Tyr Ala Asn Val Arg Lys Gly Leu His Pro Ile Leu Asn
225                 230                 235                 240

Ala Thr Val Val Ala Thr Val Glu Pro Glu Ala Gly Asp Pro Val Val
                245                 250                 255

Leu Gln Leu Leu Asp Gly Gly Ala Gly Ala Asp Val Ile Arg Asn Asp
            260                 265                 270

Gly Ile Tyr Ser Arg Asn Ile Gln Met Asn Ala Pro Lys Asn Leu Gly
        275                 280                 285
```

```
His Arg Pro Val Lys Glu Arg Trp Gly Phe Ser Arg Val Ser Ser Gly
290                 295                 300
Gly Ser Phe Ser Val Leu Gly Val Pro Asp Gly Pro His Pro Asp Met
305                 310                 315                 320
Phe Pro Pro Cys Lys Ile Thr Asp Leu Glu Ala Met Lys Val Glu Asp
                325                 330                 335
Asp Val Val Leu Ser Trp Thr Ala Pro Gly Glu Asp Phe Asp Gln Gly
            340                 345                 350
Gln Thr Thr Ser Tyr Glu Ile Arg Met Ser Arg Ser Leu Trp Asn Ile
        355                 360                 365
Arg Asp Asp Phe Asp Asn Ala Ile Leu Val Asn Ser Ser Glu Leu Val
370                 375                 380
Pro Gln His Ala Gly Thr Arg Glu Thr Phe Thr Phe Ser Pro Lys Leu
385                 390                 395                 400
Val Thr His Glu Leu Asp His Glu Leu Ala Glu Asp Ala Gln Glu Pro
                405                 410                 415
Tyr Ile Val Tyr Val Ala Leu Arg Ala Met Asp Arg Ser Ser Leu Arg
            420                 425                 430
Ser Ala Val Ser Asn Ile Ala Leu Val Ser Met Ser Leu Pro Pro Asn
        435                 440                 445
Ser Ser Pro Val Val Ser Arg Asp Asp Leu Ile Leu Lys Gly Val Leu
450                 455                 460
Thr Thr Val Gly Leu Ile Ala Ile Leu Cys Leu Ile Met Val Val Ala
465                 470                 475                 480
His Cys Ile Phe Asn Arg Lys Lys Arg Pro Ser Arg Lys Glu Asn Glu
                485                 490                 495
Thr Lys Phe Leu
            500

<210> SEQ ID NO 3
<211> LENGTH: 1620
<212> TYPE: DNA
<213> ORGANISM: human

<400> SEQUENCE: 3
caccactgta tcagctaaaa cagacatcag catttgttca gggcttaaga aaggatttga      60
ggtggttgaa aaactgaatg gaaaagctta tggctctgtg atgatattag tgaccagcgg     120
agatgataag cttcttggca attgcttacc cactgtgctc agcagtggtt caacaattca     180
ctccattgcc ctgggttcat ctgcagcccc aaatctggag gaattatcac gtcttacagg     240
aggtttaaag ttcttgttc cagatatatc aaactccaat agcatgattg atgctttcag     300
tagaatttcc tctggaactg gagacatttt ccagcaacat attcagcttg aaagtacagg     360
tgaaaatgtc aaacctcacc atcaattgaa aaacacagtg actgtggata atactgtggg     420
caacgacact atgtttctag ttacgtggca ggccagtggt cctcctgaga ttatattatt     480
tgatcctgat ggacgaaaat actacacaaa taatttttatc accaatctaa cttttcggac     540
agctagtctt tggattccag gaacagctaa gcctgggcac tggacttaca ccctgaacaa     600
tacccatcat tctctgcaag ccctgaaagt gacagtgacc tctcgcgcct ccaactcagc     660
tgtgccccca gccactgtgg aagcctttgt ggaaagagac agcctccatt ttcctcatcc     720
tgtgatgatt tatgccaatg tgaaacaggg attttatccc attcttaatg ccactgtcac     780
tgccacagtt gagccagaga ctggagatcc tgttacgctg agactccttg atgatggagc     840
aggtgctgat gttataaaaa atgatggaat ttactcgagg tattttttct cctttgctgc     900
```

-continued

```
tacacagcaa acgtaatat tcagatgaat gctccaagga aatcagtagg cagaaatgag    960
gaggagcgaa agtggggctt tagccgagtc agctcaggag gctccttttc agtgctggga   1020
gttccagctg ccccccaccc tgatgtgttt ccaccatgca aaattattga cctggaagct   1080
gtaaaagtag aagaggaatt gaccctatct tggacagcac ctggagaaga ctttgatcag   1140
ggccaggcta caagctatga aataagaatg agtaaaagtc tacagaatat ccaagatgac   1200
tttaacaatg ctattttagt aaatacatca aagcgaaatc ctcagcaagc tggcatcagg   1260
gagatattta cgttctcacc ccagatttcc acgaatggac ctgaacatca gccaaatgga   1320
gaaacacatg aaagccacag aatttatgtt gcaatacgag caatggatag aactccttta   1380
cagtctgctg tatctaacat tgcccaggcg cctctgttta ttcccccaa ttctgatcct    1440
gtacctgcca gagattatct tatattgaaa ggagttttaa cagcaatggg tttgatagga   1500
atcatttgcc ttattatagt tgtgacacat catactttaa gcaggaaaaa gagagcagac   1560
aagaaagaga atggaacaaa attattataa ataaatatcc aaagtgtctt ccttctcaaa   1620
```

<210> SEQ ID NO 4
<211> LENGTH: 943
<212> TYPE: PRT
<213> ORGANISM: human

<400> SEQUENCE: 4

```
Met Thr Gln Arg Ser Ile Ala Gly Pro Ile Cys Asn Leu Lys Phe Val
 1               5                  10                  15

Thr Leu Leu Val Ala Leu Ser Ser Glu Leu Pro Phe Leu Gly Ala Gly
                20                  25                  30

Val Gln Leu Gln Asp Asn Gly Tyr Asn Gly Leu Leu Ile Ala Ile Asn
            35                  40                  45

Pro Gln Val Pro Glu Asn Gln Asn Leu Ile Ser Asn Ile Lys Glu Met
        50                  55                  60

Ile Thr Glu Ala Ser Phe Tyr Leu Phe Asn Ala Thr Lys Arg Arg Val
65                  70                  75                  80

Phe Phe Arg Asn Ile Lys Ile Leu Ile Pro Ala Thr Trp Lys Ala Asn
                85                  90                  95

Asn Asn Ser Lys Ile Lys Gln Glu Ser Tyr Glu Lys Ala Asn Val Ile
                100                 105                 110

Val Thr Asp Trp Tyr Gly Ala His Gly Asp Asp Pro Tyr Thr Leu Gln
            115                 120                 125

Tyr Arg Gly Cys Gly Lys Glu Gly Lys Tyr Ile His Phe Thr Pro Asn
        130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
                180                 185                 190

Val Thr Arg Cys Ser Ser Asp Ile Thr Gly Ile Phe Val Cys Glu Lys
            195                 200                 205

Gly Pro Cys Pro Gln Glu Asn Cys Ile Ile Ser Lys Leu Phe Lys Glu
        210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255
```

-continued

```
Thr His Asn Gln Glu Ala Pro Asn Leu Gln Asn Gln Met Cys Ser Leu
        260                 265                 270
Arg Ser Ala Trp Asp Val Ile Thr Asp Ser Ala Asp Phe His His Ser
        275                 280                 285
Phe Pro Met Asn Gly Thr Glu Leu Pro Pro Pro Thr Phe Ser Leu
        290                 295                 300
Val Gln Ala Gly Asp Lys Val Val Cys Leu Val Leu Asp Val Ser Ser
305                 310                 315                 320
Lys Met Ala Glu Ala Asp Arg Leu Leu Gln Leu Gln Ala Ala Glu
                325                 330                 335
Phe Tyr Leu Met Gln Ile Val Glu Ile His Thr Phe Val Gly Ile Ala
                340                 345                 350
Ser Phe Asp Ser Lys Gly Glu Ile Arg Ala Gln Leu His Gln Ile Asn
        355                 360                 365
Ser Asn Asp Asp Arg Lys Leu Leu Val Ser Tyr Leu Pro Thr Thr Val
    370                 375                 380
Ser Ala Lys Thr Asp Ile Ser Ile Cys Ser Gly Leu Lys Lys Gly Phe
385                 390                 395                 400
Glu Val Val Glu Lys Leu Asn Gly Lys Ala Tyr Gly Ser Val Met Ile
                405                 410                 415
Leu Val Thr Ser Gly Asp Asp Lys Leu Leu Gly Asn Cys Leu Pro Thr
                420                 425                 430
Val Leu Ser Ser Gly Ser Thr Ile His Ser Ile Ala Leu Gly Ser Ser
            435                 440                 445
Ala Ala Pro Asn Leu Glu Glu Leu Ser Arg Leu Thr Gly Gly Leu Lys
        450                 455                 460
Phe Phe Val Pro Asp Ile Ser Asn Ser Asn Ser Met Ile Asp Ala Phe
465                 470                 475                 480
Ser Arg Ile Ser Ser Gly Thr Gly Asp Ile Phe Gln Gln His Ile Gln
                485                 490                 495
Leu Glu Ser Thr Gly Glu Asn Val Lys Pro His His Gln Leu Lys Asn
                500                 505                 510
Thr Val Thr Val Asp Asn Thr Val Gly Asn Asp Thr Met Phe Leu Val
            515                 520                 525
Thr Trp Gln Ala Ser Gly Pro Pro Glu Ile Ile Leu Phe Asp Pro Asp
        530                 535                 540
Gly Arg Lys Tyr Tyr Thr Asn Asn Phe Ile Thr Asn Leu Thr Phe Arg
545                 550                 555                 560
Thr Ala Ser Leu Trp Ile Pro Gly Thr Ala Lys Pro Gly His Trp Thr
                565                 570                 575
Tyr Thr Leu Asn Asn Thr His His Ser Leu Gln Ala Leu Lys Val Thr
                580                 585                 590
Val Thr Ser Arg Ala Ser Asn Ser Ala Val Pro Pro Ala Thr Val Glu
            595                 600                 605
Ala Phe Val Glu Arg Asp Ser Leu His Phe Pro His Pro Val Met Ile
        610                 615                 620
Tyr Ala Asn Val Lys Gln Gly Phe Tyr Pro Ile Leu Asn Ala Thr Val
625                 630                 635                 640
Thr Ala Thr Val Glu Pro Glu Thr Gly Asp Pro Val Thr Leu Arg Leu
                645                 650                 655
Leu Asp Asp Gly Ala Gly Ala Asp Val Ile Lys Asn Asp Gly Ile Tyr
                660                 665                 670
```

-continued

```
Ser Arg Tyr Phe Phe Ser Phe Ala Ala Asn Gly Arg Tyr Ser Leu Lys
        675                 680                 685

Val His Val Asn His Ser Pro Ser Ile Ser Thr Pro Ala His Ser Ile
        690                 695                 700

Pro Gly Ser His Ala Met Tyr Val Pro Gly Tyr Thr Ala Asn Gly Asn
705                 710                 715                 720

Ile Gln Met Asn Ala Pro Arg Lys Ser Val Gly Arg Asn Glu Glu Glu
                725                 730                 735

Arg Lys Trp Gly Phe Ser Arg Val Ser Ser Gly Gly Ser Phe Ser Val
                740                 745                 750

Leu Gly Val Pro Ala Gly Pro His Pro Asp Val Phe Pro Pro Cys Lys
        755                 760                 765

Ile Ile Asp Leu Glu Ala Val Lys Val Glu Glu Glu Leu Thr Leu Ser
        770                 775                 780

Trp Thr Ala Pro Gly Glu Asp Phe Asp Gln Gly Gln Ala Thr Ser Tyr
785                 790                 795                 800

Glu Ile Arg Met Ser Lys Ser Leu Gln Asn Ile Gln Asp Asp Phe Asn
                805                 810                 815

Asn Ala Ile Leu Val Asn Thr Ser Lys Arg Asn Pro Gln Gln Ala Gly
                820                 825                 830

Ile Arg Glu Ile Phe Thr Phe Ser Pro Gln Ile Ser Thr Asn Gly Pro
                835                 840                 845

Glu His Gln Pro Asn Gly Glu Thr His Glu Ser His Arg Ile Tyr Val
        850                 855                 860

Ala Ile Arg Ala Met Asp Arg Asn Ser Leu Gln Ser Ala Val Ser Asn
865                 870                 875                 880

Ile Ala Gln Ala Pro Leu Phe Ile Pro Pro Asn Ser Asp Pro Val Pro
                885                 890                 895

Ala Arg Asp Tyr Leu Ile Leu Lys Gly Val Leu Thr Ala Met Gly Leu
                900                 905                 910

Ile Gly Ile Ile Cys Leu Ile Ile Val Val Thr His His Thr Leu Ser
        915                 920                 925

Arg Lys Lys Arg Ala Asp Lys Lys Glu Asn Gly Thr Lys Leu Leu
        930                 935                 940
```